United States Patent [19]

Patel

[11] Patent Number: 5,217,958

[45] Date of Patent: Jun. 8, 1993

[54] 1,2-HYDROXY PHOSPHONATES AND DERIVATIVES THEREOF

[75] Inventor: Dinesh V. Patel, Somerset, N.J.

[73] Assignee: E. R. Squibb & Sons, Inc., Princeton, N.J.

[21] Appl. No.: 509,398

[22] Filed: Apr. 12, 1990

Related U.S. Application Data

[63] Continuation-in-part of Ser. No. 317,257, Feb. 28, 1989, abandoned, which is a continuation-in-part of Ser. No. 163,593, Mar. 3, 1988, abandoned.

[51] Int. Cl.$^5$ .................. A61K 37/02; C07K 5/06
[52] U.S. Cl. ................................. 514/19; 530/331; 514/18; 544/118; 544/119; 544/122; 544/133; 544/137; 544/157
[58] Field of Search ............. 514/19, 18; 530/331; 544/111, 119, 122, 133, 137, 157

[56] References Cited

FOREIGN PATENT DOCUMENTS

| | | |
|---|---|---|
| 5288186 | 1/1986 | Australia . |
| 0103867 | 9/1983 | European Pat. Off. . |
| 0104041 | 3/1984 | European Pat. Off. . |
| 0190891 | 8/1986 | European Pat. Off. . |
| 0249445 | 6/1987 | European Pat. Off. . |
| 0266950 | 10/1987 | European Pat. Off. . |
| 3825242 | 2/1989 | Fed. Rep. of Germany . |
| 201036 | 9/1984 | Japan . |
| WO90/09172 | 2/1989 | PCT Int'l Appl. . |

OTHER PUBLICATIONS

*Chemical Abstracts*, vol. 98, p. 646 (72259n) (1983).
*Organometallics*, vol. 90, p. 527 (72285c) (1979).
Powers et al., "Inhibition of Human Leukoctye Elastase, Porcine Pancreatic Elastase and Cathepsin G by Peptide Ketones", Proceedings from 9th American Peptide Symposium, Jun. 23-28, 1985, Univ. of Toronto, Canada.

*Primary Examiner*—Lester L. Lee
*Attorney, Agent, or Firm*—Theodore R. Furman, Jr.

[57] ABSTRACT

Compounds of the formula

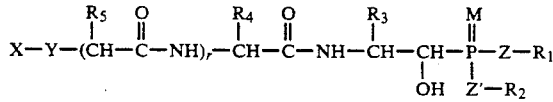

are disclosed. These compounds are inhibitors of renin and therefore useful as cardiovascular agents.

6 Claims, No Drawings

1,2-HYDROXY PHOSPHONATES AND DERIVATIVES THEREOF

This is a continuation-in-part of U.S. Ser. No. 317,257 filed Feb. 28, 1989 and now abandoned, which is a continuation-in-part of U.S. Ser. No. 163,593 filed Mar. 3, 1988 and now abandoned.

BACKGROUND OF THE INVENTION

Jones et al. in WO 84/03044 disclose renin inhibiting tetra-, penta-, or hexapeptide analogues of the formula $$X-D-E-A-B-Z-W$$

where X and W are terminal groups; D, E, B and Z, of which any one or, except with reduced analogues, two may be absent, are aromatic, lipophilic or (in the case of E) aromatic, lipophilic, or basic amino acid or amino acid analogue residues, and A is an analogue of a lipophilic or aromatic dipeptide residue wherein the peptide link is replaced by one to four-atom carbon or carbonnitrogen link which as such or in hydrated form is an unhydrolyzable tetrahedral analogue of the transition state of the peptide bond as given above. In particular, A is defined as

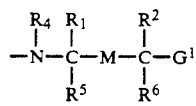

wherein M can be —CH—OH.

Szelke et al. in European Patent Application 104,041 disclose renin inhibitory polypeptides including the partial sequence $$X-A-B-Z-W-\text{ and}$$

$$X-\text{Phe}-\text{His}-A-B-Z-W$$

wherein A is and G is

X is hydrogen, protecting group, or an amino residue, B is a lipophilic amino acyl residue, and Z plus w are an amino alcohol residue or Z is aminoacyl and W is hydroxy, ester, amide, etc.

Matsueda et al. in U.S. Pat. No. 4,548,926 disclose renin inhibiting peptides of the formula

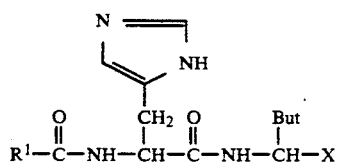

wherein But represents an isobutyl or sec-butyl group and X includes a group of the formula —CH($R^2$)—Y.

Gordon et al. in U.S. Pat. No. 4,514,391 disclose hydroxy substituted peptide compounds of the formula

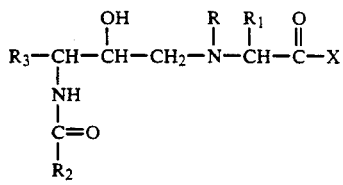

which possess angiotensin converting enzyme or enkephalinase inhibition activity.

A copending application, U.S. Ser. No. 003,446 entitled "N-HETEROCYCLIC ALCOHOL RENIN INHIBITORS", filed Jan. 15, 1987, discloses compounds of the formula

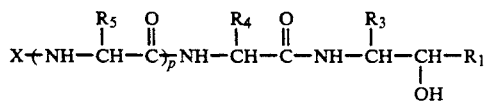

wherein $R_1$ can be various N-heterocyclic moieties.

SUMMARY OF THE INVENTION

In accordance with the present invention novel compounds which are inhibitors of renin, and therefore useful as cardiovascular agents, are disclosed. These compounds have the formula

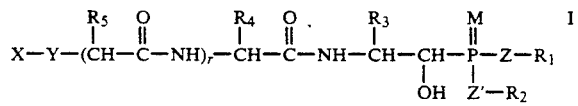

including pharmaceutically acceptable salts thereof, wherein M is oxygen or sulfur and wherein Y can be —$CH_2$—, —NH— or —O—, provided that:
when Y is

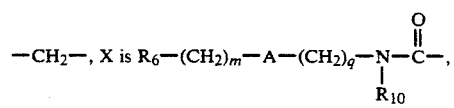

—$CH_2$—, X is $R_6$—$(CH_2)_m$—A—$(CH_2)_q$—N(—$R_{10}$)—C(=O)—, $R_6$—$(CH_2)_m$—A—$(CH_2)_q$—C(=O)—, $R_6$—$(CH_2)_m$—A—$(CH_2)_q$—O—C(=O)—, $R_6$—$(CH_2)_m$—A—$(CH_2)_q$—S—,
$R_6$—$(CH_2)_m$—A—$(CH_2)_q$—SO—,
$R_6(CH_2)_m$—A—$(CH_2)_q$—$SO_2$, $R_6$—$(CH_2)_m$—A—$(CH_2)_q$—N($R_{10}$)—$SO_2$—, $R_6$—$(CH_2)_m$—A—$(CH_2)_q$—C(=O)—S—,

-continued

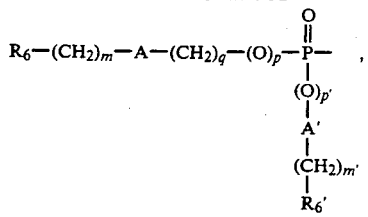

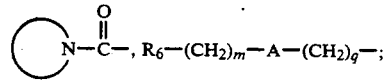

when Y is —NH—, X is hydrogen,

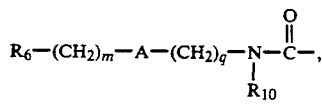

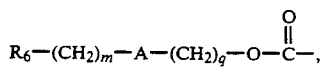

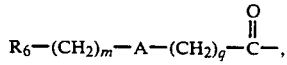

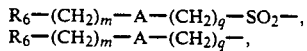

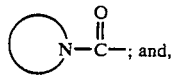; and, when Y is —O—,

X is 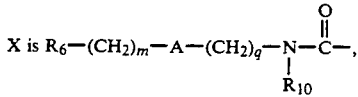

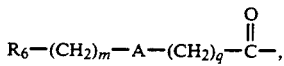

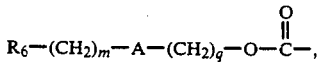

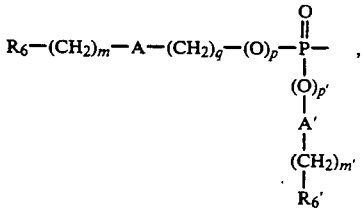

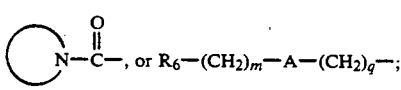

and, further wherein
$R_1$, $R_1'$, $R_2$, $R_2'$, $R_6'$, $R_6''$, $R_6'''$, $R_{12}$, $R_{13}$ and $R_{14}$ are independently selected from hydrogen, alkyl, arylalkyl, aryl, heteroaryl, and cycloalkyl;

Z and Z' are independently selected from a single bond,

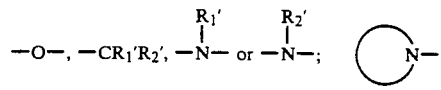 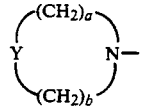

represents a heterocyclic ring of the formula

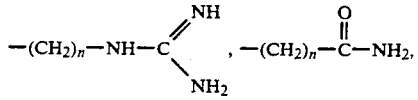

wherein Y is —$CH_2$, O, S, or N—$R_9$, a is an integer from 1 to 4, and b is an integer from 1 to 4 provided that the sum of a plus b is an integer from 2 to 5 and such heterocyclic rings wherein one carbon atom has a lower alkyl substituent;

$R_3$ and $R_5$ are independently selected from hydrogen, lower alkyl, halo substituted lower alkyl, —$(CH_2)_n$—aryl, —$(CH_2)_n$—heterocyclo, —$(CH_2)_n$—OH, —$(CH_2)_n$—O—lower alkyl, —$(CH_2)_n$—$NH_2$, —$(CH_2)_n$—SH, —$(CH_2)_n$—S—lower alkyl, —$(CH_2)_n$—O—$(CH_2)_g$—OH, —$(CH_2)_n$—O—$(CH_2)_g$—$NH_2$, —$(CH_2)_n$—S—$(CH_2)_g$—OH,

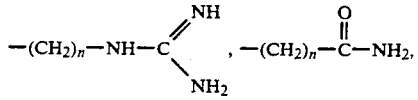

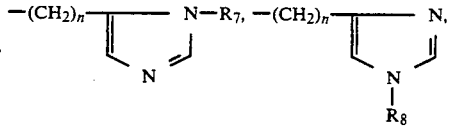

and —$(CH_2)_n$—cycloalkyl;

$R_4$ is selected from hydrogen, lower alkyl, halo substituted lower alkyl, —$(CH_2)_n$—aryl, —$(CH_2)_n$—heterocyclo, —$(CH_2)_n$—OH, —$(CH_2)_n$—O—lower alkyl, —$(CH_2)_n$—$NH_2$, —$(CH_2)_n$—SH, —$(CH_2)_n$—S—lower alkyl, —$CH_2)_n$—O—$(CH_2)_g$—OH, —$(CH_2)_n$—O—$(CH_2)_g$—$NH_2$, —$(CH_2)_n$—S—$(CH_2)_g$—OH,

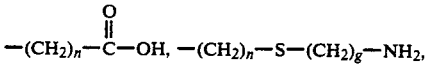

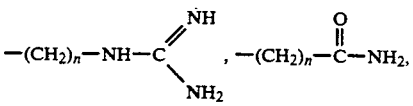

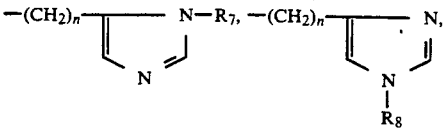

-continued

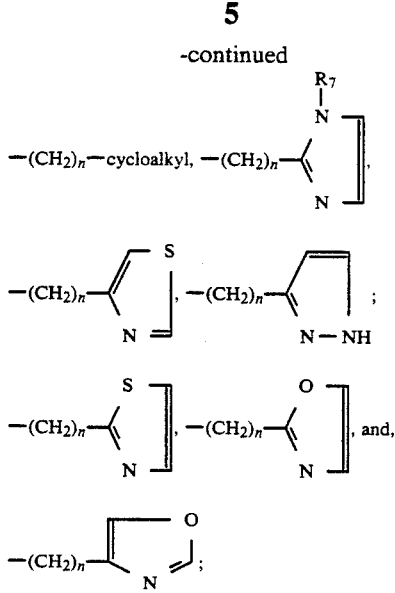

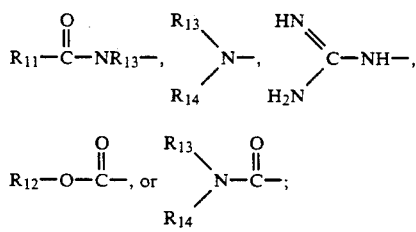

$R_6$ is hydrogen, alkyl, aryl, arylalkyl, heteroaryl, cycloalkyl,

m, m', m" and m'" are zero or an integer from 1 to 5;
n is an integer from 1 to 5;
p and p' are zero or 1;
g is an integer from 2 to 5;
r is one, except that r can be zero or one in the case when Y is —NH— and $R_6$ is hydrogen, alkyl, aryl, arylalkyl, heteroaryl or cycloalkyl;
q is zero or an integer from 1 to 7;
$R_7$ is

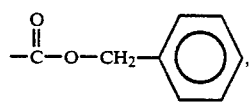

$R_8$ is 2,4-dinitrophenyl,

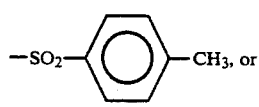

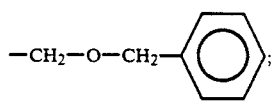

$R_9$ is hydrogen, lower alkyl, —$(CH_2)_n$ or —$(CH_2)_n$—cycloalkyl;
$R_{10}$ is —A'—$(CH_2)_{m'}$—$R_6'$;
$R_{11}$ is alkyl, alkoxy, arylalkyl or arylalkoxy;
A and A' are independently a single bond or

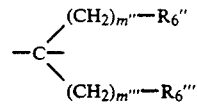

The present invention optionally includes ester, ether, ketal or acetal derivatives of the alcohols of formula I.

Exemplary 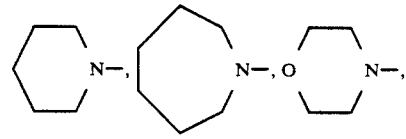 groups include

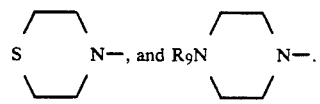

DETAILED DESCRIPTION OF THE INVENTION

This invention in its broadest aspects relates to the compounds of formula I above, to compositions and the method of using such compounds as antihypertensive agents.

The term lower alkyl used in defining various symbols refers to straight or branched chain radicals having up to seven carbons. Similarly, the terms lower alkoxy and lower alkylthio refer to such lower alkyl groups attached to an oxygen or sulfur. The preferred lower alkyl groups are straight or branched chain of 1 to 5 carbons.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkythio of 1 to 4 carbons, lower alkoxy of 1 to 4 carbons, halogen, hydroxy, amino, —NH—alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred hetero groups include 2-thiazolyl, 2- and 4-imidazolyl, 2- and 3-thienyl, 2- and 3-furyl, 2-, 3- and 4-pyridyl. The term hetero also includes bicyclic rings wherein the five or six membered ring containing O, S and N atoms as defined above is fused to a benzene ring. The preferred bicyclic ring is benzimidazolyl.

The term heteroaryl refers to fully unsaturated rings of 5 or 6 atoms containing one or two O and S atoms and/or one to four N atoms provided that the total number of hetero atoms in the ring is 4 or less. The hetero ring is attached by way of an available carbon atom. Preferred hetero groups include 2-thiazolyl, 2- and 4-imidazolyl, 2- and 3-thienyl, 2- and 3-furyl, 2-, 3- and 4-pyridyl. The term hetero also includes bicyclic rings wherein the five or six membered ring containing O, S and N atoms as defined above is fused to a benzene ring. The preferred bicyclic ring is benzimidazolyl.

Compounds of formula I for which Y may be —CH$_2$—, —NH— or —O—, and r equals one can be prepared by coupling an acid of formula

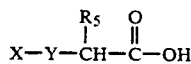

to an amine of formula

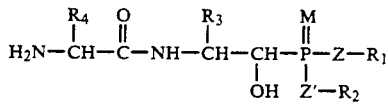

in a solvent, such as dimethylformamide, using a coupling agent, such as dicyclohexylcarbodiimide, in the presence of hydroxybenzotriazole. The amine of formula III is prepared by reacting the protected amino acid of formula

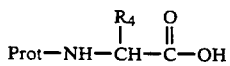

(wherein Prot is an amine protecting group such as t-butoxycarbonyl or benzyloxycarbonyl) with the amine

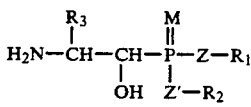

in the presence of a coupling agent, such as dicyclohexylcarbodiimide, and thereafter removing the protecting group by known means. Compounds of formula V are novel intermediates and, as such are considered as part of this invention.

Alternatively, compounds of formula I for which Y may be —CH$_2$—, —NH— or —O—, and r equals one can be prepared by coupling an acid of formula II to an amino acid ester of formula

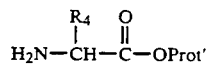

(wherein Prot' is an oxygen protecting group such as benzyl, methyl, etc.) to provide a compound of the formula

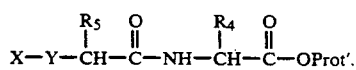

After removing the protecting group (Prot'), for example by employing hydrogenolysis using hydrogen and palladium catalyst when Prot' equals benzyl or by saponification using aqueous sodium hydroxide when Prot' equals methyl, the resulting acid is coupled to an amine of formula V using dicyclohexylcarbodiimide and hydroxybenzotriazole to provide compounds of formula I.

Compounds of formula

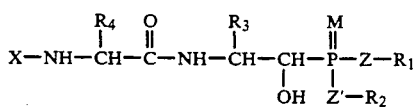

which are examples of formula I in which r=0, Y=—NH— and R$_6$ is other than

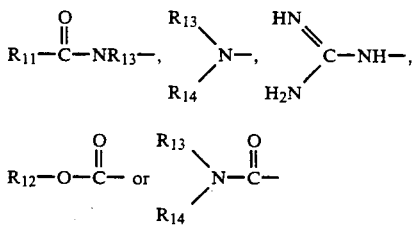

can be prepared by coupling acids of the formula

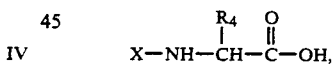

wherein Y=—NH— and R$_6$ is restricted as above, to amines of formula III in a solvent, such as dimethylformamide, using dicyclohexylcarbodiimide and hydroxybenzotriazole. The acids of formula IIa can be prepared in a manner similar to that described for the preparation of compound II when Y is —NH—, but substituting R$_4$ for R$_5$.

In all of the above procedures, suitable consideration should be employed with regard to the use of protecting groups for potentailly reactive functional groups, and in such cases a final step(s) would be carried out involving the removal of such required protecting groups.

Amines of formula V are prepared from compounds of formula

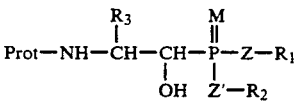

by removing the protecting group, Prot, by hydrogenolysis using hydrogen and palladium catalyst in a solvent, such as methanol, when Prot is benzyloxycarbonyl or by treatment with anhydrous hydrogen chloride in dioxane when Prot is t-butyloxycarbonyl.

Compounds of formula IX can be prepared by the condensation of a compound of the formula $$\text{Prot}-\text{NH}-\overset{R_3}{\underset{|}{\text{CH}}}-\overset{O}{\underset{\|}{\text{CH}}} \qquad \text{X}$$

(the preparation of which has been described by Fehrentz et al. in *Synthesis*; p. 676, (1983)). with the phosphonyl of the formula $$\text{H}-\overset{M}{\underset{\|}{\underset{|}{\text{P}}}}-\text{Z}-\text{R}_1 \qquad \text{XI}$$
$$\text{Z}'-\text{R}_2$$

using an appropriate base, such as potassium fluoride, sodium alkoxide or n-butyl lithium, in a solvent, such as dichloromethane, tetrahydrofuran or dimethylformamide.

To prepare the compounds of formula XI wherein Z is a single bond, Z' is oxygen and M is oxygen, a compound of the formula $$R_1-\text{Halo} \qquad \text{XII}$$

(wherein Halo is Cl, Br or I)
can be treated with magnesium in a solvent, such as diethyl ether or tetrahydrofuran, to provide the Grignard reagent of the formula $$R_1-\text{Mg}-\text{Halo} \qquad \text{XIII}$$

Treatment of compound XIII with dimethylchlorophosphite followed by acidic workup provides the phosphinate of the formula $$R_1-\overset{O}{\underset{\|}{\underset{|}{\text{P}}}}-\text{H.} \qquad \text{XIV}$$
$$\text{OCH}_3$$

Alternatively, reaction of one equivalent of compound XIII with phosphorous trichloride at lower temperatures (e.g. −78° C.) gives the alkyl dichlorophosphine $$R_1-P\overset{\diagup\text{Cl}}{\diagdown\text{Cl}} \qquad \text{XV}$$

which, upon treatment with a base, such as triethylamine, and methanol provides the compound of formula XIV.

Alkaline hydrolysis of the methyl ester XIV using sodium hydroxide or potassium hydroxide followed by coupling with an alcohol of the formula $$R_2-\text{OH} \qquad \text{XVI}$$

using dicyclohexylcarbodiimide and N-N-dimethylaminopyridine in a solvent, such as dichloromethane, tetrahydrofuran or dimethylformamide, affords the phosphonyl compound of formula XI wherein Z is a single bond, Z' is oxygen and M is oxygen. Reaction of compound XI as described above with the aldehyde of formula X provides the corresponding compounds of formula IX.

To prepare the compounds of formula XI where Z and Z' are both single bonds and M is oxygen, a halide of the formula $$R_2-\text{Halo} \qquad \text{XVII}$$

can be converted to the Grignard reagent $$R_2-\text{Mg}-\text{Halo} \qquad \text{XVIII}$$

using the methodology described above for the preparation of compound XIII. Reaction of compound XVIII with the phosphinate of formula XIV provides the desired formula XI intermediates.

To prepare the compounds of formula XI wherein Z, Z' and M are each oxygen, one equivalent of a compound of the formula $$R_1-\text{OH} \qquad \text{XIX}$$

is reacted with phosphorous trichloride in the presence of a tertiary base, such as triethylamine, to provide a compound of the formula $$R_1-\text{O}-P\overset{\diagup\text{Cl}}{\diagdown\text{Cl}} \qquad \text{XX}$$

Aqueous hydrolysis of compound XX provides a compound of the formula $$R_1-\text{O}-\overset{O}{\underset{\|}{\underset{|}{\text{P}}}}-\text{H.} \qquad \text{XXI}$$
$$\text{OH}$$

Coupling of compound XXI with an alcohol of formula XVI using dicyclohexylcarbodiimide and N,N-dimethylaminopyridine in a solvent, such as dichloromethane, tetrahydrofuran or dimethylformamide, provides the compounds of formula XI wherein Z, Z' and M are each oxygen.

For compounds of formula XI where Z, Z' and M are each oxygen and $R_1 = R_2$, two equivalents of a compound of formula XIX can be reacted with phosphorous trichloride in the presence of triethylamine followed by the aqueous hydrolysis of the resulting monochlorophosphite.

To prepare the compounds of formula XI wherein Z is oxygen, Z' is $$\overset{R_1'}{\underset{|}{-\text{N}-}}$$

and M is oxygen, the dichlorophosphite of formula XX is reacted with one equivalent of an amine of the formula $$\overset{R_1'}{\underset{|}{\text{H}-\text{N}-\text{R}_1}} \qquad \text{XXII}$$

in the presence of a tertiary base, such as triethylamine, and in a solvent, such as dichloromethane, tetrahydrofuran or dimethylformamide, followed by aqueous hydrolysis.

To prepare the compounds of formula IX where Z is

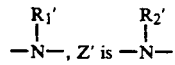, Z' is 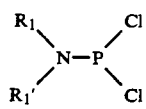

and M is oxygen, one equivalent of a compound of formula XXII is reacted with phosphorous trichloride in the presence of a tertiary base, such as triethylamine, to provide a compound of the formula

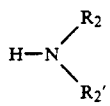

which can be treated with one equivalent of a compound of the formula

 XXIIIa in the presence of triethylamine and the resulting product hydrolyzed to provide the desired formula X compounds.

Each of the above-described species of compound XI can be reacted with the aldehyde of formula X as described above to provide the corresponding compounds of formula IX where M is oxygen.

To prepare the compounds of formula IX wherein M is sulfur, the compounds of formula IX where M is oxygen (prepared as described above) are treated with phosphorous pentasulfide at elevated temperatures.

Alternatively, the phosphonyl compounds of formula XI where M is oxygen can be treated with phosphorous pentasulfide as above to provide the corresponding compounds of formula XI where M is sulfur which can then be reacted with the aldehyde of formula X to provide compounds of formula IX wherein M is sulfur.

Amines of formula V where Z and M are oxygen and Z' is oxygen, a single bond or

can also be prepared by treatment of the corresponding compound IX where Z and Z' are oxygen and R₁ is methyl with 2,2-dimethoxypropane in the presence of an acid such as p-toluene sulfonic acid to give a compound of the formula

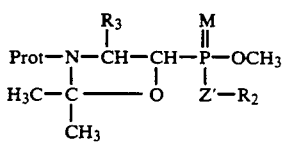 E followed by demethylation with sodium iodide or trimethyl amine to give a compound of the formula

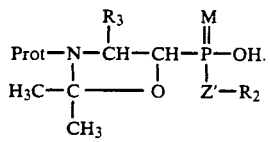 F

Esterification of the acid F with a compound of formula XII in the presence of suitable base, such as sodium or potassium carbonate, provides a compound of the formula

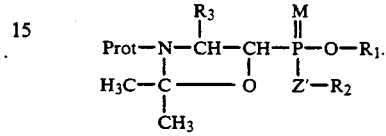 G

Deprotection of compound G under standard conditions provides the amine of formula V where Z and M are oxygen and Z' is oxygen, a single bond or

Treatment of compound F, or its sodium salt, with thionyl chloride or oxalyl chloride will give the chloridate of the formula

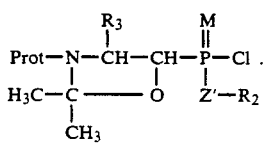 H

Reaction of the chloridate H with an amine of the formula XXII followed by appropriate deprotection provides an amine of formula V where Z is

Treatment of a compound of formula H with compound XIII followed by appropriate deprotection provides the amines of formula V where Z is a single bond.

The following subsections describe the synthesis of compounds of formula I wherein R₆ is hydrogen, alkyl, aryl, heteroaryl, cycloalkyl or in the case wherein X is

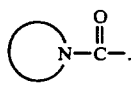

To make the compounds of formula I wherein Y is —CH₂— and X is

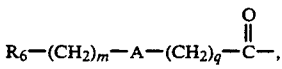

a compound of the formula

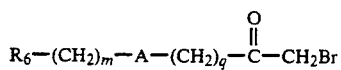 XXIV (the preparation of which has been described, for example, in *Tetrahedron Letters*, 26, 5611–5615, 1970) is coupled with a diethyl malonate derivative having the formula

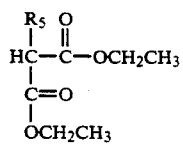 XXV in a solvent, e.g. tetrahydrofuran, and in the presence of a base, e.g. sodium hydride, to provide a compound of the formula

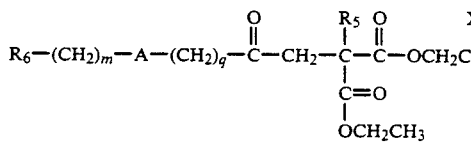 XXVI

Compound XXVI in a solvent, e.g. aqueous ethanol, is treated in a strong base, such as sodium hydroxide, and thereafter with hydrochloric acid and heat to provide the compounds of formula II where Y is —$CH_2$— and X is

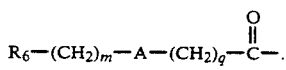

Reaction with compound III, as above, provides the corresponding compounds of formula I.

To make the compounds of formula I where Y is —$CH_2$— and X is

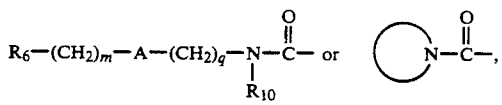

and $R_5$ is —$(CH_2)_n$—aryl and n=1, a compound of the formula

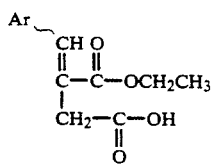 XXVII (the preparation of which has been described in *J. Amer. Chem. Soc.*, 90, 3495, (1968)), is hydrogenated in the presence of a palladium on carbon catalyst to provide a compound having the formula

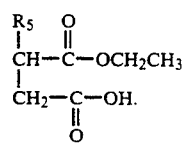 XXVIII

Compound XXVIII is reacted with a compound of the formula

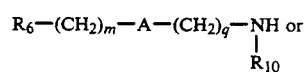 XXIX

 XXX in the presence of a catalyst, such as hydroxybenzotriazole, and dicyclohexylcarbodiimide to provide the ethyl ester of the formula

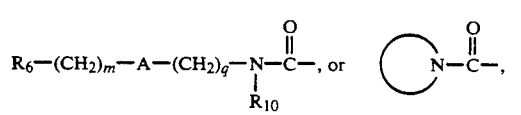 XXXI

XXXII

Compound XXXI or XXXII, in a solvent such as aqueous ethanol, is treated with a strong base, e.g. sodium hydroxide to provide the compounds of formula II wherein Y is —$CH_2$— and X is

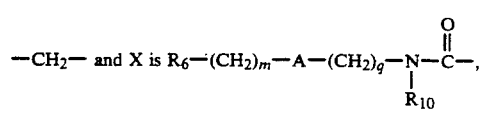

and $R_5$ is —$(CH_2)_n$—aryl and n=1. Reaction with compound III, as above, provides the corresponding compounds of formula I.

Alternatively, to make the compounds of formula I where Y is

—$CH_2$— and X is $R_6-(CH_2)_m-A-(CH_2)_q-N-\overset{O}{\underset{|}{C}}-$,
  $R_{10}$

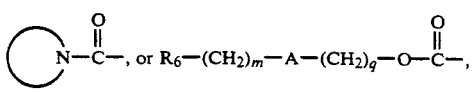

and $R_5$ is —$(CH_2)_n$—aryl and n=1 to 5, a dialkylmalonate of the formula

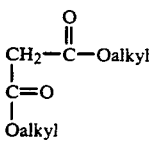 XXXIII in a solvent, such as tetrahydrofuran, is treated with sodium hydride and thereafter reacted with a compound of the formula

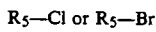 XXXIV to provide a compound having the formula

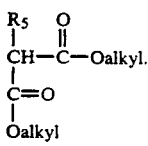 XXXV

Compound XXXV, in a solvent such as aqueous ethanol, is treated with a strong base, e.g. sodium hydroxide, and thereafter with hydrochloric acid to provide

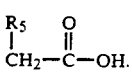 XXXVI

Compound XXXVI is treated with benzyl alcohol and 4-dimethylamino pyridine in a solvent, e.g. methylene chloride, in the presence of dicyclohexylcarbodiimide to provide the ester of the formula

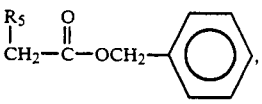 XXXVII which is treated with diisopropylamine and n-butyl lithium in a solvent such as tetrahydrofuran, and thereafter reacted with t-butyl bromoacetate to provide

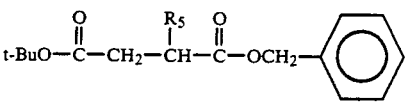 XXXVIII

Compound XXXVIII, in a solvent, such as methylene chloride, is treated with a strong acid, e.g. trifluoroacetic acid, to provide a compound of the formula

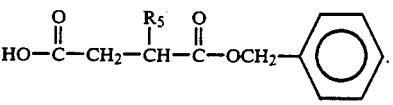 XXXIX

Compound XXXIX, in a solvent, such as tetrahydrofuran, is coupled with

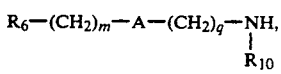, 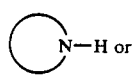 or

-continued
$R_6-(CH_2)_m-A-(CH_2)_q-OH$ in the presence of a catalyst, such as hydroxybenzotriazole or dimethylaminopyridine, and dicyclohexylcarbodiimide to provide the compounds of formula II where Y is —CH$_2$— and X is

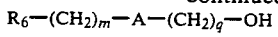
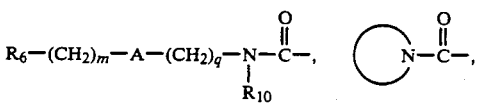

or

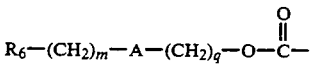

and R$_5$ is —(CH$_2$)$_n$—aryl and n=1 to 5. Reaction with compound III, as above, provides the corresponding compounds of formula I.

To make the compounds of formula I where Y is —CH$_2$— and X is R$_6$—(CH$_2$)$_m$—A—(CH$_2$)$_q$—S—, a compound of the formula

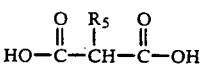 XL is reacted with dimethylamine in the presence of formaldehyde to provide a compound of the formula

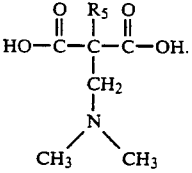 XLI

Compound XLI is heated to provide the acrylic acid of the formula

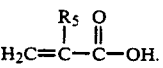 XLII

Compound XLII, in a solvent, such as piperidine, is reacted with a compound of the formula
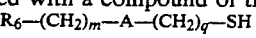 XLIII to provide

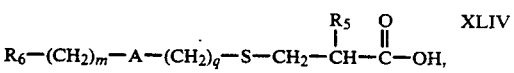 XLIV that is, the compounds of formula II wherein Y is —CH$_2$— and X is R$_6$—(CH$_2$)$_m$—A—(CH$_2$)$_q$—S—. Reaction with compound III, as above, provides the corresponding compounds of formula I.

Alternatively, a compound of the formula XLII may be esterified by reaction with ethanol in the presence of dicyclohexylcarbodiimide and a catalyst such as dimethylaminopyridine to give a compound of the formula

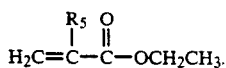 XLIIa

Compound XLIIa, in a solvent such as ethanol is then reacted with a compound of the formula XLIII in the presence of a base such as sodium ethoxide to give a compound of the formula

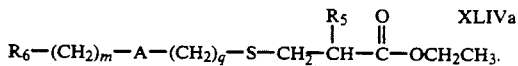 XLIVa

Compound XLIVa is treated with sodium hydroxide to give compound XLIV.

When X is $R_6-(CH_2)_m-A-(CH_2)_q-SO-$, compound XLIII in a solvent, e.g. methanol, is treated with hydrogen peroxide. When X is $R_6-(CH_2)_m-A-(CH_2)_q-SO_2-$, compound XLIII. in a solvent such as methanol, is treated with potassium monopersulfate. The resulting species of formula II can be reacted with compound III, as above, to provide the compounds of formula I wherein Y is —CH$_2$— and X is $R_6-(CH_2)_m-A-(CH_2)_q-SO-$ and $R_6-(CH_2)_m-A-(CH_2)_q-SO_2-$, respectively.

To make the compounds of formula I where Y is —CH$_2$— and X is

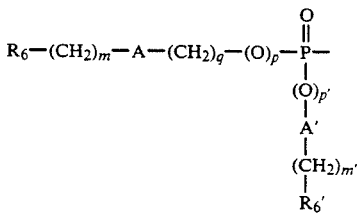

and p and p' are 1, a compound of the formula

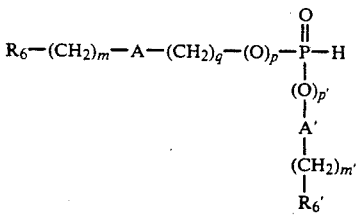 XLV is reacted with the acrylic acid of formula XLII in dichloromethane and in the presence of bis(trimethylsilyl)acetamide to provide the compound of formula II where Y is —CH$_2$— and X is

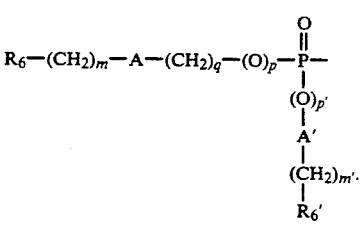

Reaction with compound III, as above, provides the corresponding compounds of formula I.

To make compounds of the formula I where Y is —CH$_2$— and X is

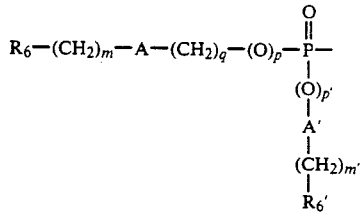

and p is one and p' is zero, a compound of the formula

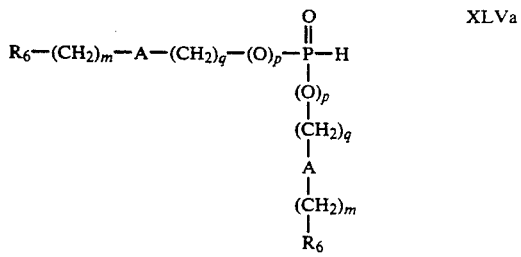 XLVa wherein p is one is reacted with a compound of the formula $R_6'-(CH_2)_{m'}-A'-MgBr$    XLVI The resulting species is then reacted with the acrylic acid of the formula XLII to provide the compound of the formula II where Y is —CH$_2$— and X is

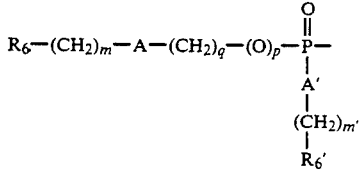

and where p is one. Reaction with compound III, as above, provides the corresponding compounds of formula I.

To make compounds of the formula I where Y is —CH$_2$— and X is

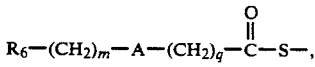

a compound of the formula

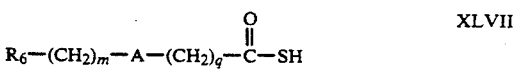 XLVII is reacted with an acrylic acid of formula XLII to give a compound of the formula

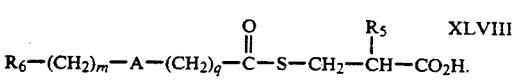 XLVIII

Reaction of compound XLVIII with compound III, as described above for compounds of formula II, provides the corresponding compounds of formula I.

To make compounds of the formula I where Y is —CH$_2$— and X=HS, a compound of the formula I where

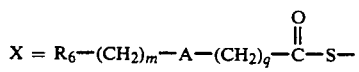

is treated with ammonium hydroxide solution.

To make compounds of the formula I where Y is —CH$_2$— and

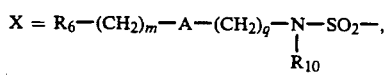

a compound of formula XLVIII is treated with ammonium hydroxide solution to give a compound of the formula

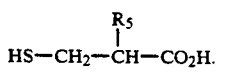 XLIX

The compound of formula XLIX is esterified, for example, by treatment with ethanol and dicyclohexylcarbodiimide in the presence of a catalyst, such as dimethylaminopyridine, to give a compound of formula

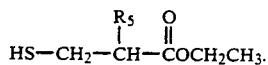 L

The compound L is treated with chlorine gas in a solvent, such as aqueous acetic acid, to give the compound

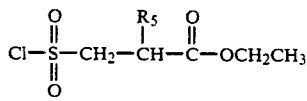 LI which is reacted with the amine of formula XXIX to give a compound of the formula

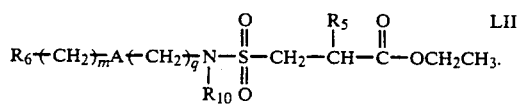 LII

Compound LII is saponified with a strong base, such as sodium hydroxide, to give a compound of the formula

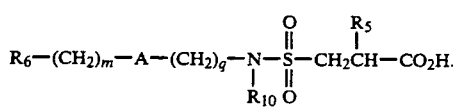 LIII

Reaction of compound LIII with compound III, as above, provides the corresponding compounds of formula I.

To prepare compounds of formula I wherein Y is —NH— and X is

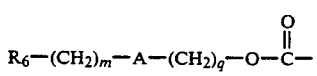

wherein r equals one, a compound of the formula

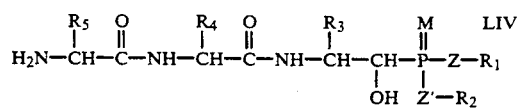 LIV is prepared by coupling a protected amino acid of the formula

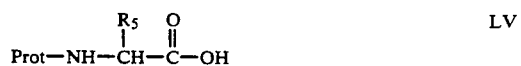 LV with the amine of formula III, and the protecting group (Prot) removed by suitable treatment, such as with hydrogen and palladium catalyst when Prot is benzyloxycarbonyl or with anhydrous hydrogen chloride in dioxane. The amine of formula LIV is treated with either an alkylchoroformate of the formula

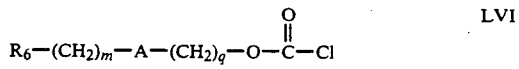 LVI or a p-nitrophenylchloroformate of formula

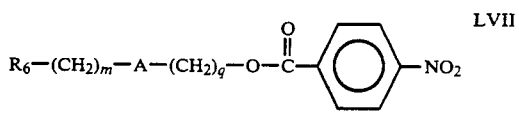 LVII to provide the corresponding compounds of formula I.

Alternatively, the protected amino acid of formula LV can be deprotected as described above, and the resulting amino acid acylated with the reagent of formula LVI in a mixed solvent system, such as tetrahydrofuran-water, using a base, such as aqueous sodium hydroxide, to maintain pH equal to approximately 8.5 to provide, after acidification and work-up, an acid of the formula

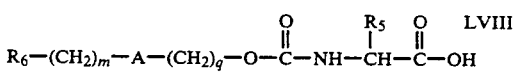 LVIII which can be converted to the corresponding compounds of formula I as described above for compounds of formula II.

To prepare compounds of formula I wherein Y is —NH— and X is

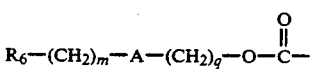

wherein r equals zero, the acid of formula LVIII is coupled to the amine of formula III to provide the corresponding compounds of formula I.

Alternatively, an amino acid of the formula

 LIX can be acylated with the reagent of formula LVI in a mixed solvent system, such as tetrahydrofuran-water, using a base, such as aqueous sodium hydroxide, to maintain pH equal to approximately 8.5 to provide, after acidification and workup, an acid of the formula

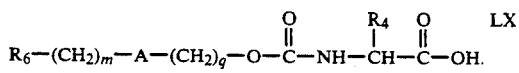

Compound LX can be coupled to an amine of formula V using dicyclohexylcarbodiimide and hydroxybenzotriazole in a solvent such as dimethylformamide to provide the corresponding compounds of formula I.

To prepare compounds of formula I wherein Y is —NH— and X is

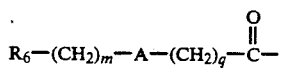

wherein r equals one, the amine of formula LIV is coupled with an acid of formula

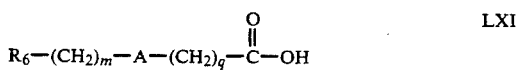

to provide the corresponding compounds of formula I.

To prepare compounds of formula I wherein Y is —NH— and X is

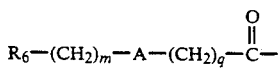

wherein r equals zero, the acid of formula LXI is coupled to the amine of formula III to provide the corresponding compounds of formula I.

To prepare compounds of formula I wherein Y is —NH— and X is $R_6-(CH_2)_m-A-(CH_2)_q-SO_2-$ wherein r equals one, the amine of formula LIV is coupled with a compound of the formula

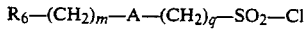

to provide the corresponding compounds of formula I.

To prepare compounds of formula I wherein Y is —NH— and X is

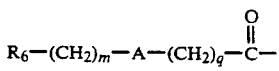

wherein r equals zero, the compound of formula LXII is coupled to the amine of formula III to provide the corresponding compounds of formula I.

To prepare compounds of formula I wherein Y is —NH— and X is

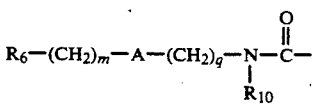

wherein r equals one, an amino acid ester hydrochloride salt of formula

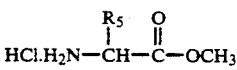

is treated with p-nitrophenyl chloroformate and diisopropylethylamine in a solvent, such as dichloromethane, to provide the compound of formula

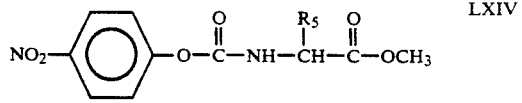

which is treated with the amine of formula XXIX to provide an ester of the formula

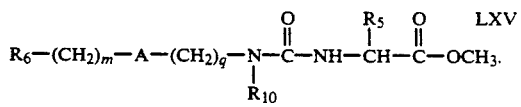

The ester of formula LXV is saponified with aqueous sodium hydroxide to provide an acid of the formula

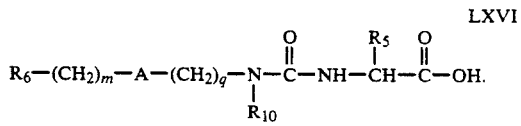

The acid of formula LXVI is coupled to an amine of formula III to provide the corresponding compounds of formula I.

To prepare compounds of formula I wherein Y is —NH— and X is

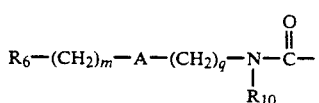

wherein r equals zero, an amino acid ester hydrochloride salt of the formula

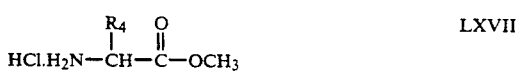

is treated with p-nitrophenyl chloroformate and diisopropylethylamine in a solvent, such as dichloromethane, to provide the compound of formula

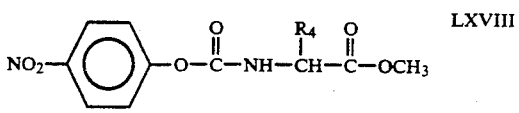

which is treated with the amine of formula XXIX to provide an ester of formula

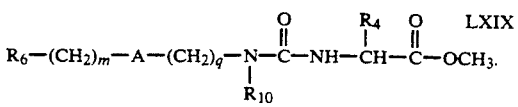

The ester of formula LXIX is saponified with aqueous sodium hydroxide to provide an acid of the formula

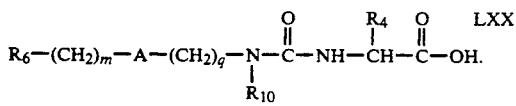
LXX

The acid of formula LXX is coupled to an amine of formula V to provide the corresponding compounds of formula I.

To prepare compounds of formula I wherein Y is —NH— and X equals

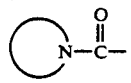

the amine of formula XXIX is substituted by an amine of the formula

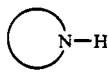
LXXI and the methodology described above for converting compounds LXIV and LXVIII to compounds of formula I is employed.

To prepare compounds of formula I wherein Y is —NH— and X is $R_6—(CH_2)_m—A—(CH_2)_q—$ wherein r equals one, an aldehyde of the formula $$R_6—(CH_2)_m—A—(CH_2)_{q-1}—\overset{O}{\overset{\|}{C}}H$$
LXXII when q is equal to 1 or greater can be reacted with either the amine of formula LIV or the amine of formula III in a reductive alkylation reaction, using either hydrogen in the presence of palladium catalyst in a solvent, such as methanol or sodium cyanoborohydride buffered at pH 8, in a solvent, such as aqueous ethanol, to provide the corresponding compounds of formula I. When q is equal to zero, that is the point of attachment of X to Y (NH) is branched alkyl, then a ketone of appropriate structure is used such that the products of the same reductive alkylation reaction provide the corresponding compounds of formula I.

To make the compounds of formula I wherein Y is —O— and X is

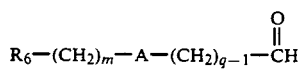

a compound of the formula

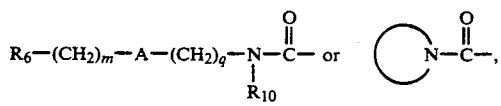
LXXIII in sulfuric acid, is treated with sodium nitrite in water to provide a compound having the formula

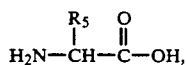
LXXIV

Compound LXXIV, in an organic solvent, such as dimethylformamide, and in the presence of a base, such as sodium bicarbonate, is treated with a compound of the formula

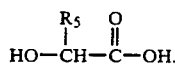
LXXV to provide a compound of the formula

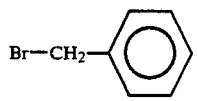
LXXVI

Compound LXXVI, in N-methyl morpholine and methylene chloride, is thereafter reacted with

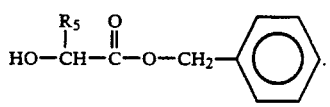
LXXVII that is, p-nitrophenyl chloroformate, in a solvent, such as methylene chloride, to yield a compound of the formula

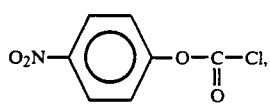
LXXVIII

Compound LXXVIII, in a solvent, such as toluene, can be reacted with a compound of the formula

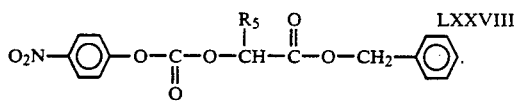
LXXIXa

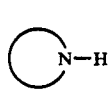
LXXIXb to provide an intermediate of the formula

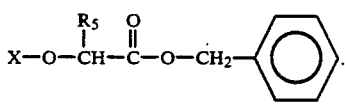
LXXX

Reduction of compound LXXX, for example by hydrogenation in ethyl acetate in the presence of a palladium/carbon catalyst, provides the compounds of formula II. Reaction with an amine of formula III (or a protected form thereof), as described above, provides the compounds of formula I wherein Y is —O— and X is

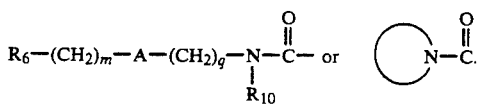

To prepare the compounds of formula I wherein Y is —O— and X is

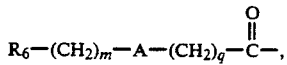

an intermediate of formula LXXVI in a solvent, such as methylene chloride, is reacted with a carboxylic acid of formula LXI. This is carried out in the presence of dimethylaminopyridine and dicyclohexylcarbodiimide and provides a compound of formula LXXX where Y is —O— and X is

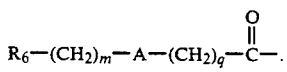

This so-formed intermediate is treated with a base, such as sodium hydroxide, to provide a corresponding compound of formula II and reacted with the amine of formula III, as above, to provide the compounds of formula I wherein Y is —O— and X is

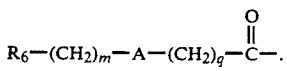

To prepare the compounds of formula I wherein Y is —O— and X is

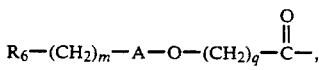

a compound of the formula $R_6-(CH_2)_m-A-(CH_2)_q-OH$    LXXXI in a solvent, such as methylene chloride, is reacted with an excess of phosgene to give a compound of the formula

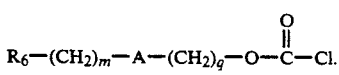    LXXXII

Compound LXXXII in a solvent, such as methylene chloride, is reacted with an intermediate of formula LXXVI, preferably in the presence of a base, e.g. triethylamine. The product can be reduced and coupled with an intermediate of formula III, as above, to provide the corresponding compounds of formula I where Y is —O— and X is

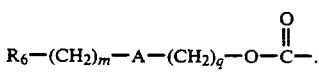

To prepare the compounds of formula I wherein Y is —O— and X is $R_6-(CH_2)_m-A-(CH_2)_q-$, a compound of the formula $R_6-(CH_2)_m-A-(CH_2)_q-Br$    LXXXIII is reacted with the compound of formula LXXVI in a solvent, such as tetrahydrofuran, and in the presence of a base, such as sodium hydride, to provide

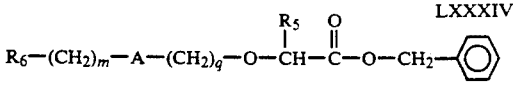    LXXXIV which can be reduced to give a compound having the formula

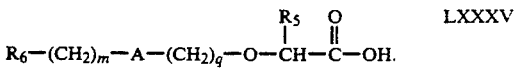    LXXXV

Coupling of compound LXXXV with compounds of formula III, as described above, provides the products of formula I.

To prepare the compounds of formula I wherein Y is —O— and X is

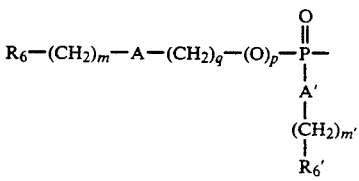

and p is zero, a compound of the formula $R_6'-(CH_2)_{m'}-A'-Br$    LXXXVI is reacted with dimethylchorophosphite to provide a compound of the formula

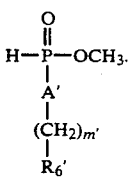    LXXXVII

Compound LXXXVII is reacted with a compound of the formula $R_6-(CH_2)_m-A-(CH_2)_q-MgBr$    LXXXVIII in a solvent, such as tetrahydrofuran, to provide

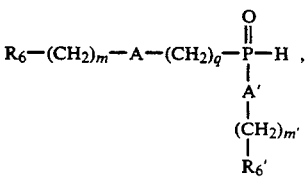    LXXXIX which can be treated with phosphorous pentachloride to provide a compound of the formula

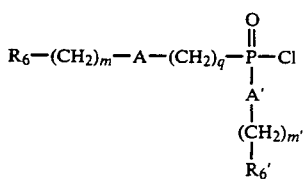 XC which is reacted with a compound of formula LXXV in a solvent, such as dichloromethane, and in the presence of triethylamine to provide

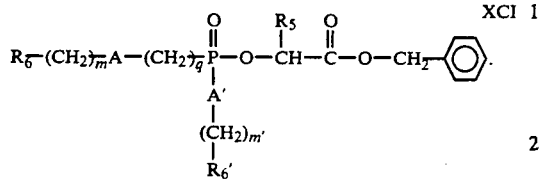 XCI

Compound XCI is reduced or saponified to the corresponding carboxylic acid of formula II which can thereafter be coupled to compounds of formula III, as above, to provide the compounds of formula I wherein Y is —O— and X is

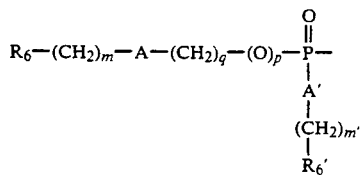

and p is zero.

To prepare the compounds of formula I as directly above, but wherein p is one, methanol is reacted with phosphorous trichloride in the presence of a base, such as triethylamine, and the resulting product is treated with aqueous sodium hydroxide to provide

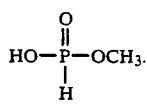 XCII

Reaction of compound XCII with a compound of formula LXXXI in a solvent, such as dichloromethane, and in the presence of dicyclohexylcarbodiimide and dimethylaminopyridine provides a compound of the formula

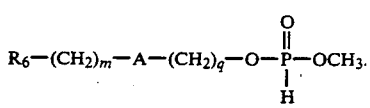 XCIII

Compound XCIII is reacted with a compound of the formula

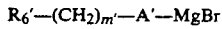 XCIV in a solvent, such as tetrahydrofuran, to give

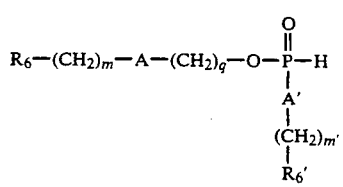 XCV which can be treated with thionyl chloride to provide a compound of the formula

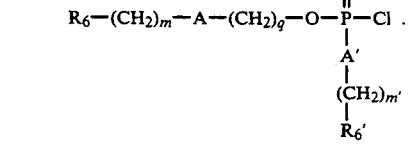 XCVI

Reaction of compound XCVI with LXXVI in a solvent, such as dichloromethane, and in the presence of dicyclohexylcarbodiimide and dimethylaminopyridine provides the ester

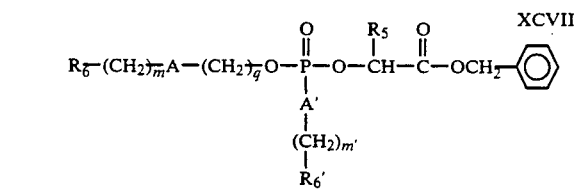 XCVII which can be reduced or saponified as described above for compound XCI to provide the corresponding carboxylic acids of formula II. Coupling of these so-formed acids of formula II with the amines of formula III, as above, provides the products of formula I wherein Y is —O—, X is $$R_6-(CH_2)_m-A-(CH_2)_q-(O)_p-\overset{\overset{O}{\|}}{\underset{\underset{R_6'}{\underset{|}{(CH_2)_{m'}}}}{\underset{|}{P}}}-$$

and p is one.

The following subsections describe the syntheses of formula I wherein $R_6$ is $$R_{11}-\overset{O}{\overset{\|}{C}}-NR_{13}-,\quad \underset{R_{14}}{\overset{R_{13}}{\underset{|}{N}}}-\quad \text{and}\quad \underset{H_2N}{\overset{HN}{\diagdown}}C-NH-.$$

To make compounds of formula I wherein Y is $$-CH_2-, \text{X is } R_6-(CH_2)_m-A-(CH_2)_q-\overset{O}{\overset{\|}{C}}-$$

for which $R_6$ is

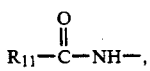

a compound of the formula

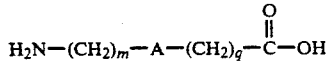  XCVIII is first treated with an acid chloride of the formula

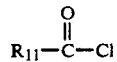  XCIX in the presence of a base, such as sodium hydroxide, in a solvent mixture such as water and tetrahydrofuran to give an acid of the formula

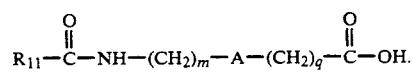  C

The acid of formula C is treated with isobutylchloroformate in the presence of a base, such as triethylamine, in a solvent, such as tetrahydrofuran, to form an intermediate mixed anhydride which is directly treated with diazomethane to form an intermediate diazoketone of the formula

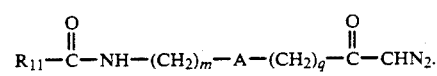  CI

The diazoketone CI is reacted with anhydrous hydrogen chloride to form a chloromethyl ketone of the formula

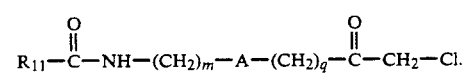  CII

The compound of formula CII is coupled with a diethylmalonate derivative having the formula

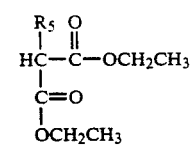  CIII in a solvent, e.g. tetrahydrofuran, and in the presence of a base, e.g. sodium hydride, to provide a compound of the formula

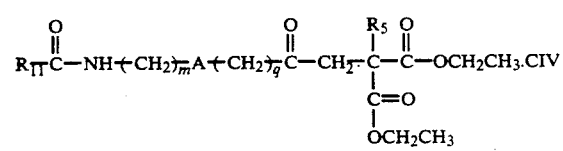  CIV

Compound CIV in a solvent, e.g. aqueous ethanol, is treated in a strong base, such as sodium hydroxide, and thereafter with hydrochloric acid and heat to provide the compounds of formula II where Y is —CH$_2$— and X is

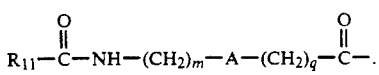

Reaction with compound III, as above, provides the corresponding compounds of formula I.

To make compounds of formula I wherein Y is —CH$_2$—, X is

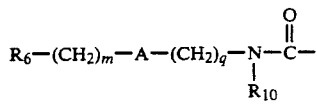

for which R$_6$ is

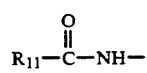

and R$_5$ is —(CH$_2$)$_n$—aryl and n=1, a compound of the formula

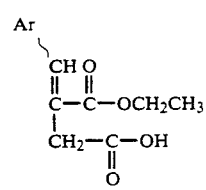  CV (the preparation of which has been described in *J. Amer. Chem. Soc.*, 90, 3495, (1968)), is hydrogenated in the presence of a palladium on carbon catalyst to provide a compound having the formula

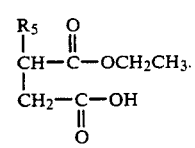  CVI

Compound CVI is reacted with a compound of the formula

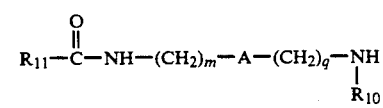  CVII in the presence of a catalyst, such as hydroxybenzotriazole, and dicyclohexylcarbodiimide to provide the ethyl ester of the formula

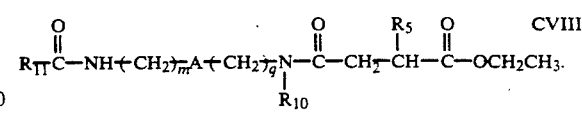  CVIII

To prepare an amine of formula CVII, an alcohol of the formula

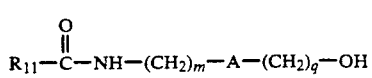  CIX is treated with p-toluenesulfonyl chloride in the presence of a base such as pyridine to form a tosylate of the formula

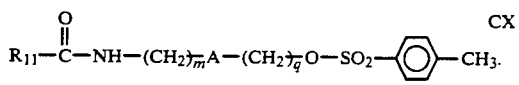   CX

The compound of formula CX is alkylated with an amine of the formula

   CXI to provide the amine of formula CVII.

Compound CVIII, in a solvent such as aqueous ethanol, is treated with a strong base, e.g. sodium hydroxide to provide the compounds of formula II wherein Y is —CH$_2$— and X is

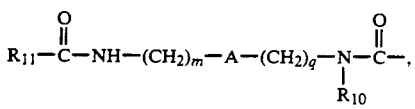

and R$_5$ is —(CH$_2$)$_n$—aryl and n=1. Reaction with compound III, as above, provides the corresponding compounds of formula I.

Alternatively, to make the compounds of formula I where Y is —CH$_2$— and X is

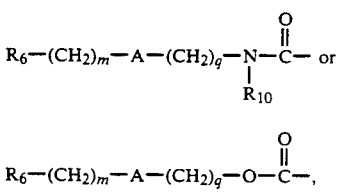

for which R$_6$ is

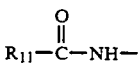

and R$_5$ is —(CH$_2$)$_n$—aryl and n=1 to 5, a dialkylmalonate of the formula

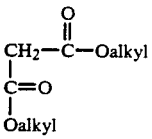   CXII in a solvent, such as tetrahydrofuran, is treated with sodium hydride and thereafter reacted with a compound of the formula R$_5$—Cl or R$_5$—Br   CXIII to provide a compound having the formula

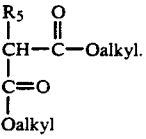   CXIV

Compound CXIV, in a solvent such as aqueous ethanol, is treated with a strong base, e.g. sodium hydroxide, and thereafter with hydrochloric acid to provide

   CXV

Compound CXV is treated with benzyl alcohol and 4-dimethylamino pyridine in a solvent, e.g. methylene chloride, in the presence of dicyclohexylcarbodiimide to provide the ester of the formula

   CXVI which is treated with diisopropylamine and n-butyl lithium in a solvent such as tetrahydrofuran, and thereafter reacted with t-butyl bromoacetate to provide

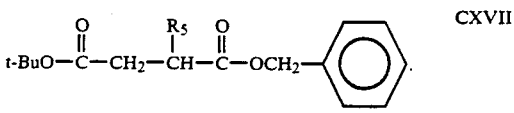   CXVII

Compound CXVII, in a solvent, such as methylene chloride, is treated with a strong acid, e.g. trifluoroacetic acid, to provide a compound of the formula

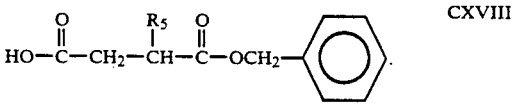   CXVIII

Compound CXVIII, in a solvent, such as tetrahydrofuran, is coupled with the amine of formula CVII or the alcohol of formula CIX in the presence of a catalyst, such as hydroxybenzotriazole or dimethylaminopyridine, and dicyclohexylcarbodiimide to provide the compounds of formula II where Y is —CH$_2$— and X is

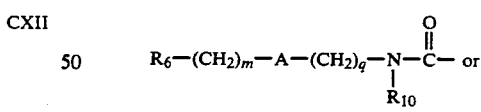

for which R$_6$ is

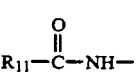

and R$_5$ is —(CH$_2$)$_n$—aryl and n=1 to 5. Reaction with compound III as above, provides the corresponding compounds of formula I.

To make the compounds of formula I where Y is —CH$_2$— and X is R$_6$—(CH$_2$)$_m$—(CH$_2$)$_q$—A—S— and where R$_6$ is

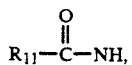

a compound of the formula

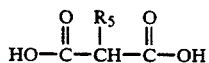   CXIX is reacted with dimethylamine in the presence of formaldehyde to provide a compound of the formula

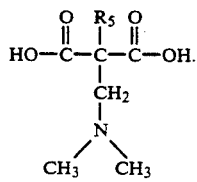   CXX

Compound CXX is heated to provide the acrylic acid of the formula

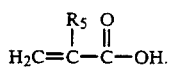   CXXI

Compound CXXI, in a solvent such as piperidine, is reacted with a compound of the formula

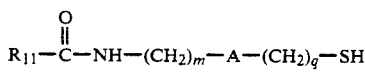   CXXII to provide

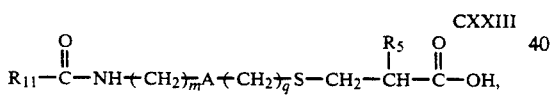   CXXIII that is, the compounds of formula II wherein Y is —$CH_2$— and X is $R_6$—$(CH_2)_m$—A—$(CH_2)_q$—S— and $R_6$ is

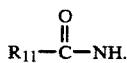

Reaction with compound III, as above, provides the corresponding compounds of formula I.

In the above reaction, compound CXXII is prepared by treating the tosylate of formula CX with mercaptoacetic acid to provide the thioester of formula

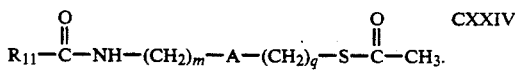   CXXIV

The thioester of formula CXXIV is hydrolyzed with aqueous ammonium hydroxide to yield the desired compound of formula CXXII.

Alternatively, a compound of the formula CXXI may be esterified by reaction with ethanol in the presence of dicyclohexylcarbodiimide and a catalyst such as dimethylaminopyridine to give a compound of the formula

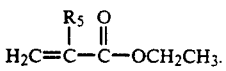   CXXIa

Compound CXXIa, in a solvent such as ethanol is then reacted with a compound of the formula CXXII in the presence of a base such as sodium ethoxide to give a compound of the formula

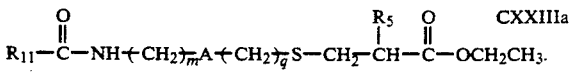   CXXIIIa

Compound CXXIIIa is treated with sodium hydroxide to give compound CXXIII. Compound CXXIII can thereafter be converted to the corresponding compounds of formula I as described above.

When X is $R_6$—$(CH_2)_m$—A—$(CH_2)_q$—SO—, compound CXXIII in a solvent, e.g. methanol, is treated with hydrogen peroxide. When X is $R_6$—$(CH_2)_m$—A—$(CH_2)_q$—$SO_2$—, compound CXXIII, in a solvent such as methanol, is treated with potassium monopersulfate. The resulting species of formula II can be reacted with compound III, as above, to provide the compounds of formula I wherein Y is —$CH_2$— and X is $R_6$—$(CH_2)_m$—A—$(CH_2)_q$—SO— and $R_6$—$(CH_2)_m$—A—$(CH_2)_q$—$SO_2$—, respectively.

To make compounds of formula I where Y is —$CH_2$— and X is

—$CH_2$— and

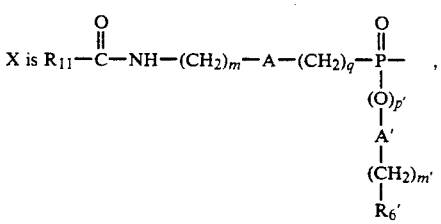

a compound of the formula

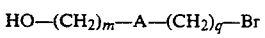   CXXV is treated with t-butyldimethylsilylchloride and imidazole in a solvent, such as dichloromethane, to provide the protected alcohol of the formula

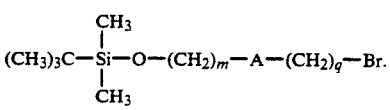   CXXVI

The compound of formula CXXVI is converted to its corresponding Grignard reagent by reaction with magnesium in a solvent, such as diethyl ether or tetrahydrofuran, followed by treatment with dimethylchlorophosphite to provide

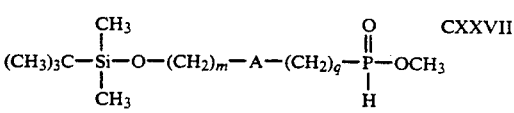   CXXVII

The compound of formula CXXVII is hydrolyzed with aqueous sodium hydroxide, then coupled to an alcohol of formula

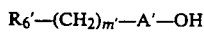

to give the compound of formula

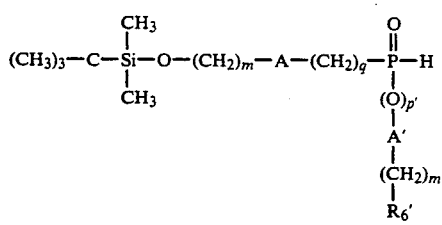

which is reacted with the acrylic acid of formula CXXI in dichloromethane in the presence of bis(trimethylsilyl)trifluoroacetamide to provide a compound of formula

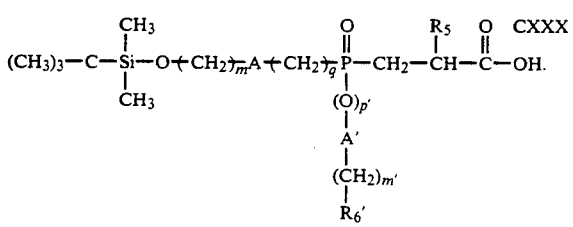

The compound of formula CXXX is esterified with t-butanol using dicyclohexylcarbodiimide and dimethylaminopyridine in dichloromethane to provide the ester of the formula

CXXXI

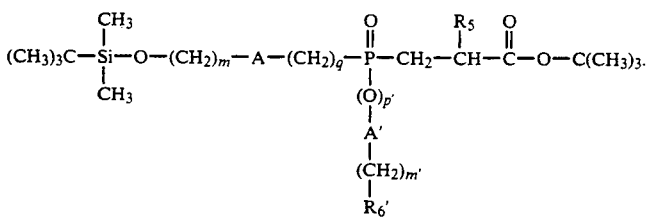

The compound of formula CXXXI is treated with aqueous hydrofluoric acid and acetonitrile to provide the corresponding alcohol which is converted to the tosylate of the formula

CXXXII

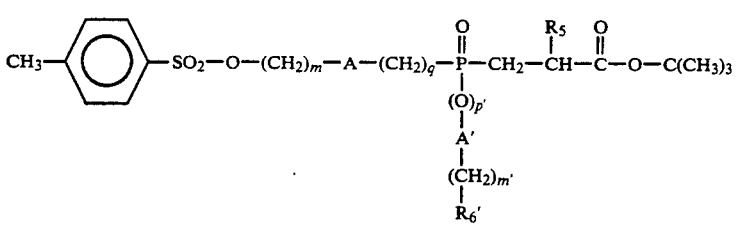

by treatment with p-toluenesulfonyl chloride and pyridine. The tosylate of formula CXXXII is treated with methanolic ammonia to provide an amine of the formula

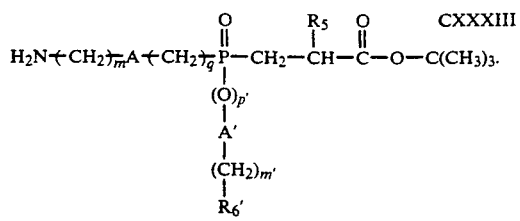

The amine of formula CXXXIII is acylated using an acid chloride of the formula

CXXXIV $$R_{11}-\overset{O}{\underset{\|}{C}}-Cl$$

in the presence of a base, such as triethylamine, in a solvent, such as dichloromethane, to give an ester of the formula

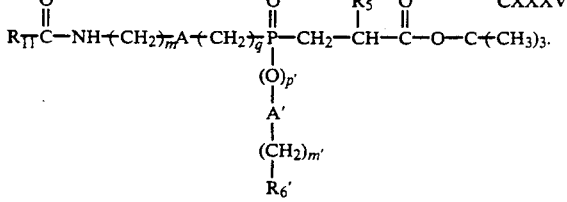

The ester of formula CXXXV is hydrolyzed with anhydrous hydrochloric acid in dioxane to produce the acid of the formula

CXXXVI

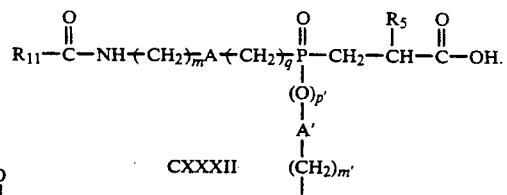

The acid of formula CXXXVI is coupled to compound III using a reagent, such as dicyclohexylcarbodiimide, in the presence of hydroxybenzotriazole in a solvent, such as dimethylformamide, to provide the corresponding compound of formula I.

To make compounds of formula I where Y is

—CH$_2$— and

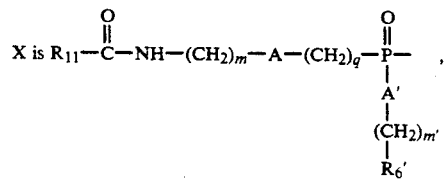

the compound of the formula CXXVII is treated with a Grignard reagent of the formula

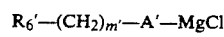      CXXXVII to provide the compound of formula

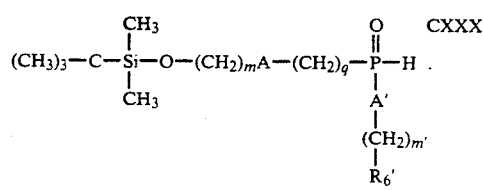

The compound of formula CXXXVIII is converted to the corresponding compound of formula I in the manner described above for the compound of formula CXXIX.

To make compounds of formula I where Y is

—CH$_2$— and

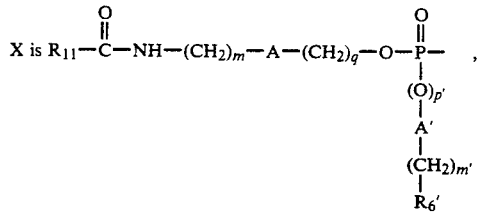

the alcohol of formula CIX is reacted with phosphorus trichloride in the presence of a base, such as triethylamine, to provide, after hydrolytic workup, the compound of the formula

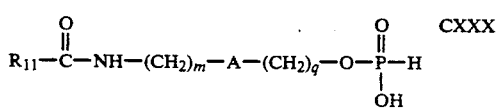

which is coupled to an alcohol of formula CXXVIII using dicylcohexylcarbodiimide and dimethylaminopyridine to provide the compound of the formula

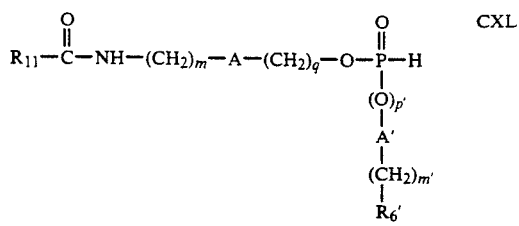

which is reacted with the acrylic acid of formula CXXI in dichloromethane in the presence of bis(trimethylsilyl)trifluoroacetamide to provide an acid of the formula

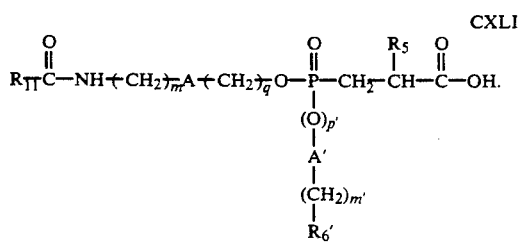

The acid of formula CXLI is converted to the corresponding compound of formula I in the manner described above for the compounds of formula II.

To make compounds of formula I where Y is

—CH$_2$— and

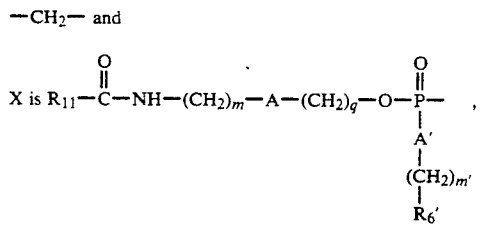

The Grignard reagent of formula CXXXVII is reacted with dimethyl chlorophosphite in a solvent, such as diethyl ether, followed by treatment with acid to form a compound of the formula

The compound of formula CXLII is hydrolyzed with aqueous sodium hydroxide, then coupled to an alcohol of formula CIX using dicyclohexylcarbodiimide and dimethylaminopyridine to provide the compound of the formula

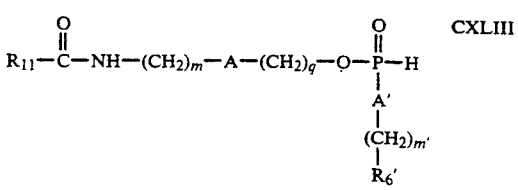

which is converted to the corresponding compound of formula I in the manner described above for the compound of formula CXL.

To make a compound of formula I wherein Y is —$CH_2$—, X is $$R_6-(CH_2)_m-A-(CH_2)_q-\underset{R_{10}}{N}-SO_2-$$

for which $R_6$ is $$R_{11}-\overset{O}{\underset{\|}{C}}-NH-,$$

a compound of the formula $$CH_3-\overset{O}{\underset{\|}{C}}-S-CH_2-\underset{R_5}{\overset{|}{CH}}-\overset{O}{\underset{\|}{C}}-OC_2H_5 \qquad \text{CXLIV}$$

is prepared by treating the ester of formula CXXIa with mercaptoacetic acid. The compound of formula CXLIV is then treated with aqueous sodium hydroxide solution to give a compound of the formula $$HS-CH_2-\underset{R_5}{\overset{|}{CH}}-CO_2H. \qquad \text{CXLV}$$

The compound of formula CXLV is esterified, for example, by treatment with ethanol and dicyclohexylcarbodiimide in the presence of a catalyst, such as dimethylaminopyridine, to give a compound of formula $$HS-CH_2-\underset{R_5}{\overset{|}{CH}}-\overset{O}{\underset{\|}{C}}OCH_2CH_3. \qquad \text{CXLVI}$$

The compound CXLVI is treated with chlorine gas in a solvent such as aqueous acetic acid, to give the compound $$Cl-\overset{O}{\underset{\underset{O}{\|}}{\overset{\|}{S}}}-CH_2-\underset{R_5}{\overset{|}{CH}}-\overset{O}{\underset{\|}{C}}-OCH_2CH_3 \qquad \text{CXLVII}$$

which is reacted with the amine of formula CVII to give a compound of the formula $$R_{11}\overset{O}{\underset{\|}{C}}-NH(CH_2)_{\overline{m}}A(CH_2)_{\overline{q}}\underset{\underset{R_{10}}{|}}{N}-\overset{O}{\underset{\underset{O}{\|}}{\overset{\|}{S}}}-CH_2-\underset{R_5}{\overset{|}{CH}}-\overset{O}{\underset{\|}{C}}-OCH_2CH_3. \qquad \text{CXLVIII}$$

Compound CXLVIII is saponified with a strong base, such as sodium hydroxide, to give a compound of the formula $$R_{11}\overset{O}{\underset{\|}{C}}-NH(CH_2)_{\overline{m}}A(CH_2)_{\overline{q}}\underset{\underset{R_{10}}{|}}{N}-\overset{O}{\underset{\underset{O}{\|}}{\overset{\|}{S}}}-CH_2\underset{R_5}{\overset{|}{CH}}-CO_2H. \qquad \text{CXLIX}$$

Reaction of compound CXLIX with compound III, as above, provides the corresponding compounds of formula I.

To make a compound of formula I wherein Y is —$CH_2$—, X is $R_6-(CH_2)_m-A-(CH_2)_q$— for which $R_6$ is $$R_{11}-\overset{O}{\underset{\|}{C}}-NH-,$$

a ketone of formula CIV, wherein X is $R_6-(CH_2)_m-A-(CH_2)_{q-1}-$, is treated with ethanedithiol in the presence of an acid, such as boron trifluoride etherate complex, to provide the thioketal of formula $$R_{11}\overset{O}{\underset{\|}{C}}-NH(CH_2)_{\overline{m}}A(CH_2)_q-\underset{\underset{S\;\;\;\;\;S}{\underset{|\;\;\;\;\;|}{\underline{\qquad\qquad}}}}{C}-CH_2-\underset{R_5}{\overset{|}{CH}}-\overset{O}{\underset{\|}{C}}-OCH_2CH_3 \qquad \text{CL}$$

which is desulfurized by treatment with activated Raney nickel to provide the compound of formula $$R_{11}\overset{O}{\underset{\|}{C}}-NH(CH_2)_{\overline{m}}A(CH_2)_{\overline{q}}CH_2-\underset{R_5}{\overset{|}{CH}}-\overset{O}{\underset{\|}{C}}-OCH_2CH_3. \qquad \text{CLI}$$

Compound CLI in a solvent, e.g. aqueous ethanol, is treated with a strong base, such as sodium hydroxide, and thereafter with hydrochloric acid and heat to provide the compounds of formula II where Y is —$CH_2$— and X is $R_6-(CH_2)_m-A-(CH_2)_q$— for which $R_6$ is $$R_{11}-\overset{O}{\underset{\|}{C}}-NH.$$

Reaction with compound III, as above, provides the corresponding compounds of formula I.

To prepare compounds of formula I in which Y is —NH—, the amine of formula III is coupled to a protected amino acid of the formula $$\text{Prot}-NH-\underset{R_5}{\overset{|}{CH}}-\overset{O}{\underset{\|}{C}}-OH, \qquad \text{CLII}$$

for which Prot can be either t-butoxycarbonyl or benzyloxycarbonyl, using dicyclohexylcarbodiimide in the presence of hydroxybenzotriazole in a solvent, such as dimethylformamide, to afford a compound of the formula $$Z-NH-\underset{R_5}{\overset{|}{CH}}-\overset{O}{\underset{\|}{C}}-NH-\underset{R_4}{\overset{|}{CH}}-\overset{O}{\underset{\|}{C}}-NH-\underset{R_3}{\overset{|}{CH}}-\underset{\underset{OH\;\;Z'-R_2}{|\;\;\;\;\;\;|}}{CH}-\overset{M}{\underset{\|}{P}}-Z-R_1. \qquad \text{CLIII}$$

The protecting group Prot, is removed from the compound of formula CLIII by hydrogenolysis using palladium hydroxide on carbon in the presence of hydrogen gas in a solvent, such as methanol, when Prot is benzyloxycarbonyl, or by treatment with anhydrous hydrogen chloride in dioxane when Prot is t-butoxycarbonyl, to provide the amine (or corresponding HCl salt thereof) of the formula $$\text{H}_2\text{N}-\underset{\underset{R_5}{|}}{\text{CH}}-\overset{\overset{O}{\|}}{\text{C}}-\text{NH}-\underset{\underset{R_4}{|}}{\text{CH}}-\overset{\overset{O}{\|}}{\text{C}}-\text{NH}-\underset{\underset{R_3}{|}}{\text{CH}}-\underset{\underset{OH}{|}}{\text{CH}}-\overset{\overset{M}{\|}}{\underset{\underset{Z'-R_2}{|}}{\text{P}}}-Z-R_1 \quad \text{CLIV}$$

To make a compound of formula I wherein Y is —NH—, X is $$R_6-(CH_2)_m-A-(CH_2)_q-\overset{\overset{O}{\|}}{C}-$$

for which $R_6$ is $$R_{11}-\overset{\overset{O}{\|}}{C}-NH-,$$

the acid of formula C is coupled to the amine of formula CLIV to provide the corresponding compound of formula I.

To make a compound of formula I wherein Y is —NH—, X is $$R_6-(CH_2)_m-A-(CH_2)_q-O-\overset{\overset{O}{\|}}{C}-$$

for which $R_6$ is $$R_{11}-\overset{\overset{O}{\|}}{C}-NH-,$$

the amine of formula CLIV is treated with p-nitrophenylchloroformate to form the p-nitrophenyl carbamate of formula $$\text{NO}_2-\!\!\bigcirc\!\!-O-\overset{\overset{O}{\|}}{C}-NH-\underset{\underset{R_5}{|}}{\text{CH}}-\overset{\overset{O}{\|}}{C}-NH-\underset{\underset{R_4}{|}}{\text{CH}}-\overset{\overset{O}{\|}}{C}-NH-\underset{\underset{R_3}{|}}{\text{CH}}-\underset{\underset{OH}{|}}{\text{CH}}-\overset{\overset{M}{\|}}{\underset{\underset{Z'-R_2}{|}}{\text{P}}}-Z-R_1 \quad \text{CLV}$$

which is next reacted with the alcohol of formula CIX in the presence of a base, such as n-methylmorpholine, and a catalyst, such as dimethylaminopyridine, in a solvent, such as dimethylformamide, to provide the corresponding compound of formula I.

To make a compound of formula I wherein Y is —NH—, X is $$R_6-(CH_2)_m-A-(CH_2)_q-\underset{\underset{R_{10}}{|}}{N}-\overset{\overset{O}{\|}}{C}-$$

for which $R_6$ is $$R_{11}-\overset{\overset{O}{\|}}{C}-NH,$$

the compound of formula CLV is treated with the amine of formula CVII to form the corresponding compound of formula I.

To make a compound of formula I wherein Y is —NH—, X is $R_6$—$(CH_2)_m$—A—$(CH_2)_q$— for which $R_6$ is $$R_{11}-\overset{\overset{O}{\|}}{C}-NH-,$$

the alcohol of formula CIX wherein X is $$R_{11}-\overset{\overset{O}{\|}}{C}-NH-(CH_2)_m-A-(CH_2)_{q-1}-$$

is oxidized to an aldehyde of the formula $$R_{11}-\overset{\overset{O}{\|}}{C}-NH-(CH_2)_m-A-(CH_2)_{q-1}-\overset{\overset{O}{\|}}{CH} \quad \text{CLVI}$$

which is subsequently coupled to the amine of formula CLIV by reductive alkylation performed by reacting the aldehyde and amine together in a solvent such as methanol in the presence of hydrogen gas and palladium hydroxide on carbon catalyst, or by mixing the amine and aldehyde in a solvent such as pH 8 buffered aqueous ethanol and adding the reagent, sodium cyanoborohydride, to form the corresponding compound of formula I.

To make a compound of formula I wherein Y is —NH—, X is $R_6$—$(CH_2)_m$—A—$(CH_2)_q$—$SO_2$— for which $R_6$ is $$R_{11}-\overset{\overset{O}{\|}}{C}-NH-,$$

the compound of formula CXXII is treated with chlorine gas in a solvent such as aqueous acetic acid to give the compound of formula $$R_{11}-\overset{\overset{O}{\|}}{C}-NH-(CH_2)_m-A-(CH_2)_q-SO_2-Cl \quad \text{CLVII}$$

which is reacted with the amine of formula CLIV in the presence of a base, such as diisopropylethylamine, in a solvent, such as dimethylformamide, to provide the corresponding compound of formula I.

The compounds of formula I wherein Y is —O— are prepared by coupling an amine of formula III with the compound of the formula $$X-O-\underset{\underset{R_5}{|}}{CH}-\overset{\overset{O}{\|}}{C}-OH \quad \text{CLVIII}$$

in a solvent, e.g. dimethylformamide, and in the presence of one or more coupling agents, e.g. dicyclohexylcarbodiimide and/or hydroxybenzotriazole hydrate.

To make the compounds of formula I wherein Y is —O— and X is

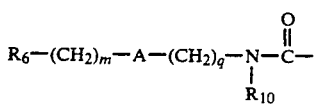

and R₆ is

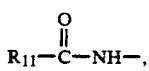

a compound of the formula

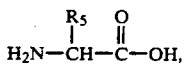     CLIX in sulfuric acid, is treated with sodium nitrite in water to provide a compound having the formula

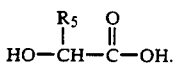     CLX

Compound CLX, in an organic solvent, such as dimethylformamide, and in the presence of a base, such as sodium bicarbonate, is treated with a compound of the formula Br—Prot′     CLXI (wherein Prot′ is an oxygen protecting group such as benzyl) to provide a compound of the formula

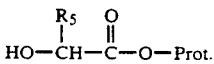     CLXII

Compound CLXII, in N-methyl morpholine and methylene chloride, is thereafter reacted with an aryl chloroformate, e.g.

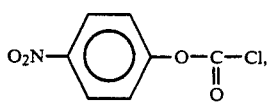     CLXIII in a solvent, such as methylene chloride, to yield a compound of the formula

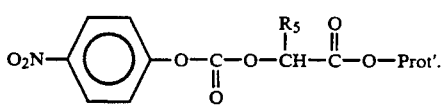     CLXIV

Compound CLXIV, in a solvent, such as toluene, can be reacted with a compound of formula CVII to provide an intermediate of the formula

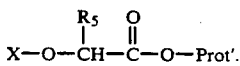     CLXV

Reduction of compound CLXV, for example by hydrogenation in ethyl acetate in the presence of a palladium/carbon catalyst, provides the compounds of formula CLVIII. Reaction with an amine of formula III (or a protected form thereof), as described above, provides the compounds of formula I wherein Y is —O— and X is

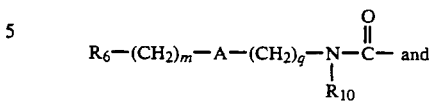

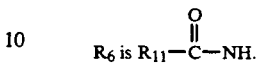

To prepare the compounds of formula I wherein Y is —O— and X is

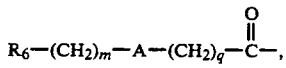

an intermediate of formula CLXII in a solvent, such as methylene chloride, is reacted with a carboxylic acid of formula C. This is carried out in the presence of dimethylaminopyridine and dicyclohexylcarbodiimide and provides a compound of formula CLXV where Y is —O— and X is

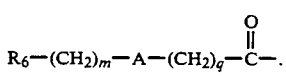

This so-formed intermediate is thereafter reduced to provide a corresponding compound of formula CLVIII and reacted with the amine of formula III, as above, to provide the compounds of formula I wherein Y is —O— and X is

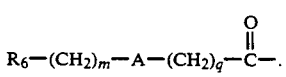

To prepare the compounds of formula I wherein Y is —O— and X is

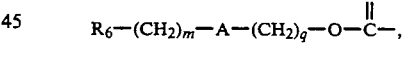

a compound of formula CLXII is treated with p-nitrophenylchloroformate to form the p-nitrophenyl carbamate of formula

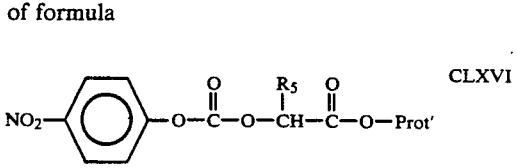     CLXVI which is next reacted with the alcohol of formula CIX in the presence of a base, such as n-methylmorpholine, and a catalyst, such as dimethylaminopyridine, in a solvent, such as dimethylformamide, to provide the compound of the formula

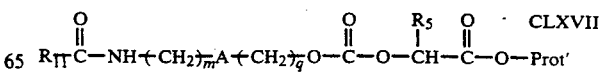     CLXVII which is reduced to provide the corresponding compound of formula CLVIII which is coupled with an amine of formula III, as described above, to provide the compounds of formula I wherein Y is —O— and X is

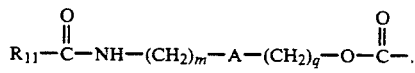

To prepare the compounds of formula I wherein Y is —O— and X is $R_6$—$(CH_2)_m$—A—$(CH_2)_q$—, the intermediate of formula CLXII is treated with the tosylate of formula CX to provide the compound of the formula

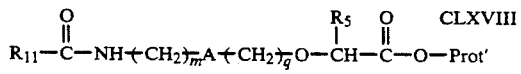

which is converted to the corresponding compound of formula I in the manner described above for compound CLXVII.

To make compounds of formula I where Y is —O— and X is

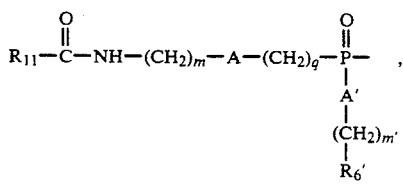

the compound of formula CXXVII is reacted with the Grignard reagent of the formula CXXXVII to provide a compound of formula

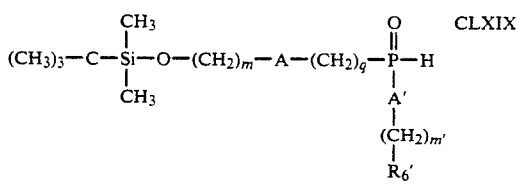

which is treated with phosphorous pentachloride in a solvent, such as methylene chloride, to provide the phosphinyl chloride of the formula

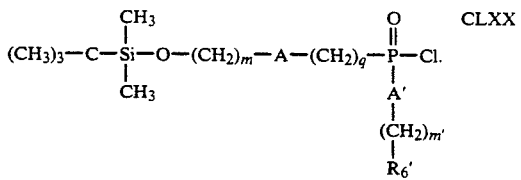

The compound of formula CLXX is then coupled to the alcohol of formula CLXII in a solvent, such as dichloromethane, using triethylamine and dimethylaminopyridine to give a compound of the formula

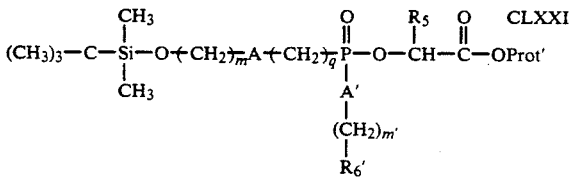

which is reduced or saponified to the corresponding acid of the formula

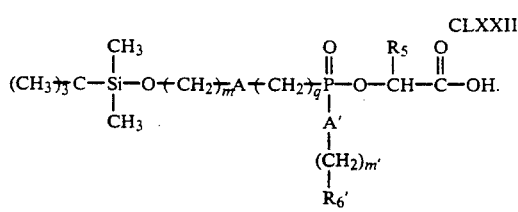

The acid of formula CLXXII can be converted to an acid of the formula

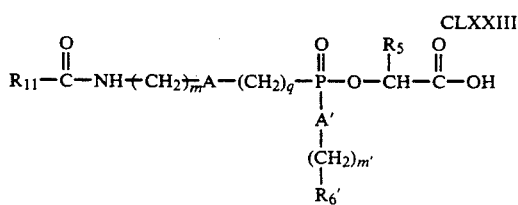

following the procedures described above for the conversion of the acids of formula CXXX to acids of formula CXXXVI. The acid of formula CLXXIII can be converted to the corresponding compounds of formula I in the manner described above for compounds of formula CXXXVI.

To make compounds of formula I where Y is —O— and X is

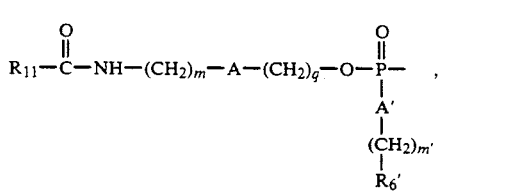

methanol is reacted with phosphorus trichloride in the presence of a base, such as triethylamine, followed by hydrolytic workup to provide the compound of the formula

The compound of formula CLXXIV is reacted with the alcohol of formula CIX in a solvent, such as dichloromethane, and in the presence of dicyclohexylcarbodiimide and dimethylaminopyridine to give an ester of the formula

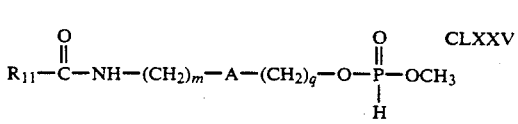

which is reacted with a Grignard reagent of formula CXXXVII to provide a compound of the formula

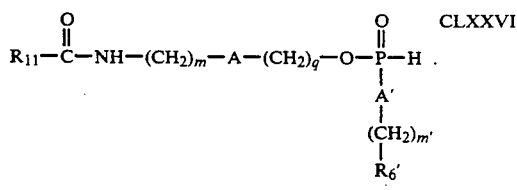

The compound of formula CLXXVI is treated with thionylchloride to produce the phosphonyl chloride of the formula

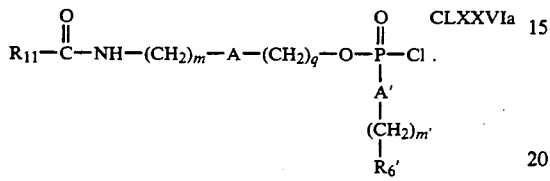

The compound of formula CLXXVIa is coupled to the alcohol of formula CLXII in a solvent, such as methylene chloride in the presence of triethylamine and dimethylaminopyridine, to provide a compound of the formula

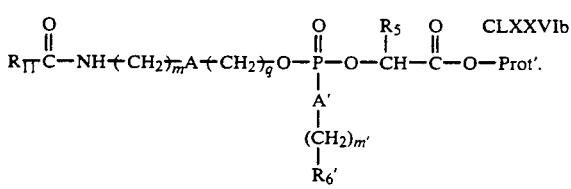

After removal of the protecting group, Prot', by the deprotection means described above, the compound of formula CLXXVIb is converted to the corresponding compounds of formula I in the manner described previously for compounds of formula CXLI.

To make compounds of formula I where Y is —O— and X is

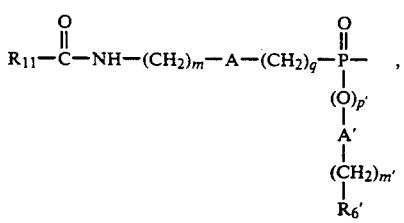

the compound of formula CLXXIV is reacted with an alcohol of the formula

HO—A'—(CH$_2$)$_{m'}$—R$_6$'  CLXXVII in a solvent, such as dichloromethane, and in the presence of dicyclohexylcarbodiimide and dimethylaminopyridine to provide

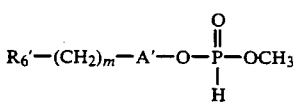

which is reacted with a Grignard reagent of the formula

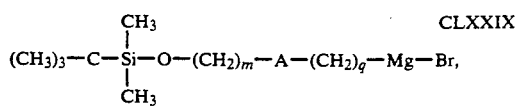

prepared from the compound of formula CXXVI as described above, to give the compound of the formula

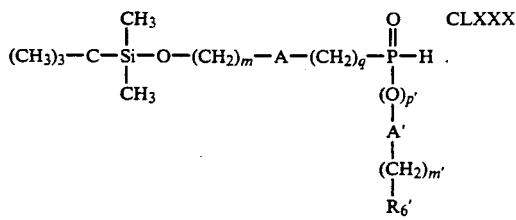

The compound of formula CLXXX is converted to the corresponding compounds of formula I in the manner as described above for compounds of formula CLXIX.

To prepare compounds of formula I with R$_6$ equal to NH$_2$, the compounds of formula I with R$_6$ as

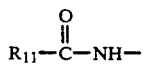

are synthesized with R$_{11}$ equal to t-butoxy or benzyloxy so that in a final step the group

is replaced by H. When R$_{11}$ is equal to t-butoxy, the compound of formula I is treated with anhydrous acid, such as hydrogen chloride dissolved in dioxane, to provide the hydrochloride salt form of the compound of formula I with R$_6$ equal to NH$_2$. When R$_{11}$ is equal to benzyloxy, the compound of formula I is treated with hydrogen in the presence of palladium hydroxide on carbon catalyst to provide the compound of formula I with R$_6$ equal to NH$_2$.

To prepare compounds of formula I with R$_6$ equal to NR$_{13}$R$_{14}$, the compounds of formula I with R$_6$ equal to NH$_2$ are treated with an aldehyde at pH 7-8 in the presence of sodium cyanoborohydride to produce the product from reductive alkylation of formula I in which R$_6$ is —NHR$_{13}$. To obtain a second substituent on nitrogen, the preceding product is subjected to the same conditions as above with the appropriate aldehyde to yield a compound of formula I wherein R$_6$ is —NR$_{14}$R$_{13}$.

To prepare the compounds of formula I where R$_6$ is

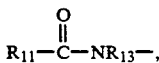

the final compounds of formula I in which R$_6$ is R$_{13}$—NH— (prepared as described above) are acylated with an acid chloride of formula XCIX by standard means known in the art, for example, reaction in a solvent, such as dimethylformamide, in the presence of triethylamine.

To prepare compounds of formula I with $R_6$ equal to NH—C(=NH)—NH$_2$, the compounds of formula I with $R_6$ equal to NH$_2$ are guanylated in a final step with a reagent such as O-methylisourea sulfate.

The following subsections describe the syntheses of compounds of formula I wherein $R_6$ is

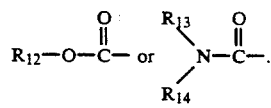

To make a compound of formula I wherein Y is —CH$_2$— and X is $R_6$—(CH$_2$)$_m$—A—(CH$_2$)$_q$—CO— and where $R_6$ is

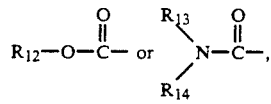

a compound of the formula

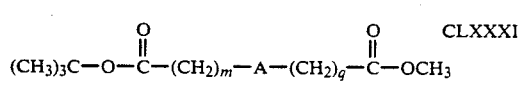

is prepared by treating a monoacid, monoester of the formula

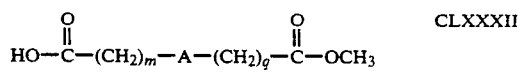

with t-butanol in the presence of dicyclohexylcarbodiimide and dimethylaminopyridine in a solvent, such as dichloromethane. The resulting diester of formula CLXXXI is then saponified by treatment first with sodium hydroxide in aqueous methanol followed by acidification to provide a compound of the formula

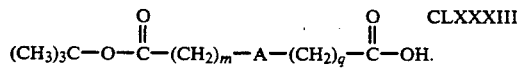

The acid of formula CLXXXIII is treated with isobutylchloroformate in the presence of a base, such as triethylamine, in a solvent, such as tetrahydrofuran, to form an intermediate mixed anhydride which is directly treated with diazomethane to form an intermediate diazoketone of the formula

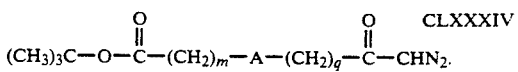

The diazoketone of formula CLXXXIV is reacted with anhydrous hydrogen chloride in a solvent, such as diethyl ether, to form a chloromethyl ketone of the formula

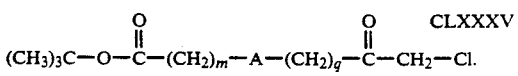

The compound of formula CLXXXV is coupled with a diethylmalonate derivative of formula CIII in a solvent, such as tetrahydrofuran, and in the presence of a base, such as sodium hydride, to provide a compound of the formula

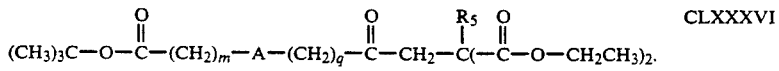

The compound of formula CLXXXVI is then treated with sodium hydroxide in aqueous ethanol, then acidified and heated to decarboxylate to form an acid of the formula

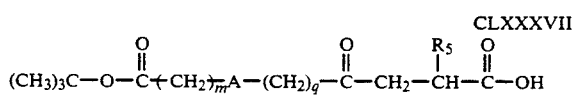

which is coupled to the amine of formula III to provide the compound of the formula

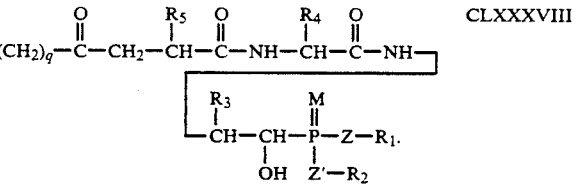

When the above compound of formula CLXXXVIII is treated with anhydrous acid, such as trifluoroacetic acid, the corresponding compound of formula I wherein $R_6$ is

is prepared.

Treatment of the compound of formula I wherein $R_6$ is

with an alcohol of the formula

in the presence of dicyclohexylcarbodiimide and dimethylaminopyridine in a solvent, such as dichloromethane, provides the corresponding compounds of formula I with R₆ is

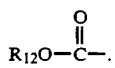

Treatment of the compound of formula I wherein R₆ is

with an amine of the formula

in the presence of dicyclohexylcarbodiimide and hydroxybenzotriazole in a solvent, such as dimethylformamide, provides the corresponding compounds of formula I wherein R₆ is

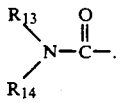

To make a compound of formula I wherein Y is —CH₂—, X is

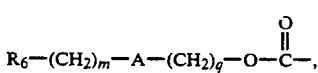

an alcohol of the formula

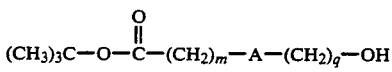

is coupled to an acid of formula CXVIII using dicyclohexylcarbodiimide and dimethylaminopyridine, followed by reduction with hydrogen in the presence of palladium catalyst to remove the benzyl ester group providing an acid of the formula

which is coupled an amine of formula III in the manner as described above for the compound CLXXXVII to provide the compound of formula

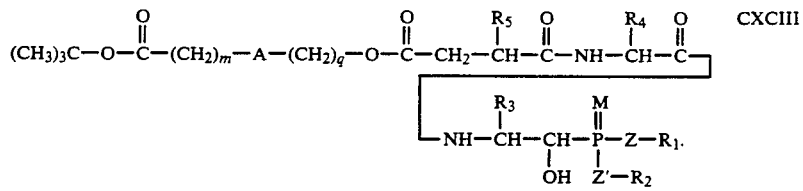

The compound of formula CXCIII is treated as described above for the compound CLXXXVIII to provide the corresponding compounds of formula I for which R₆ can be

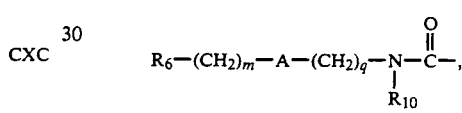

To make a compound of formula I wherein Y is —CH₂—, X is

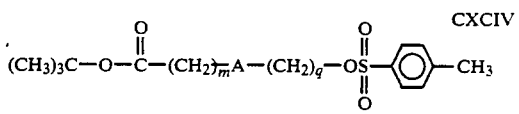

a compound of the formula CXCI is converted to the corresponding tosylate of the formula

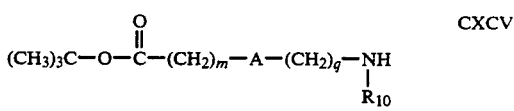

by treatment with p-toluenesulfonyl chloride in pyridine. The compound of formula CXCIV is next reacted with an amine of formula CXI to provide a compound of the formula

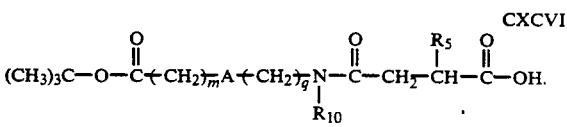

which is acylated with the acid of formula CXVIII using dicyclohexylcarbodiimide and hydroxybenzotriazole in a solvent such as dimethylformamide, which, after removal of the benzyl ester group by saponification, provides the compound $$(CH_3)_3C-O-\overset{O}{\overset{\|}{C}}(CH_2)_m-A-(CH_2)_q-\overset{}{\underset{R_{10}}{N}}-\overset{O}{\overset{\|}{C}}-CH_2-\overset{R_5}{\underset{}{CH}}-\overset{O}{\overset{\|}{C}}-OH.$$ CXCVI The compound of formula CXCVI is coupled an amine of formula III in the manner described above for the compound of formula CLXXXVII to provide the compound of the formula

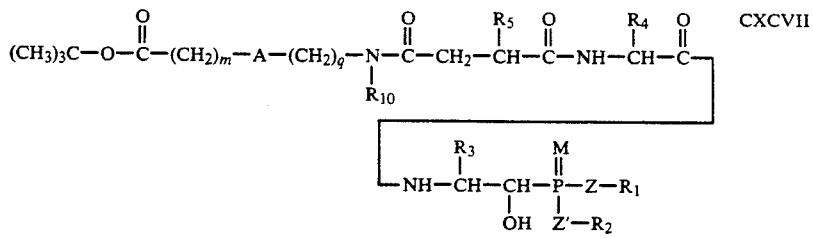

The compound of formula CXCVII is treated as decribed above for the compound CLXXXVIII to provide the corresponding compounds of formula I for which R₆ can be

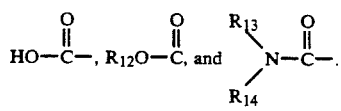

To make compounds of formula I wherein Y is —CH₂—, X is R₆—(CH₂)ₘ—A—(CH₂)_q—S—, R₆—(CH₂)ₘ—A—(CH₂)_q—SO— and R₆—(CH₂)ₘ—A—(CH₂)_q—SO₂—, the tosylate of formula CXCIV is converted to the acid of formula

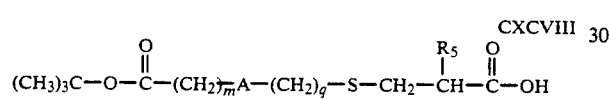

as described for the similar conversion of tosylate CX to acid CXXIII. The acid CXCVIII is coupled to the amine III to give The preparation of analogous examples of compound I for which X is R₆—(CH₂)ₘ—A—(CH₂)_q—SO— and R₆—(CH₂)ₘ—A—(CH₂)_q—SO₂ can be accomplished using the acid of formula CXCVIII in the manner described for the acid of formula CXXIII, that is prior oxidation to the sulfoxide or sulfone intermediates prior to coupling to the amine of formula III. Subsequent conversion to compounds of formula I would proceed as described above.

To make compounds of formula I wherein Y is —CH₂—, X is

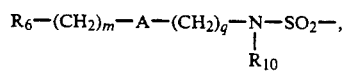

the earlier described compound of formula CXLVII is treated with the amine of formula CXCV in the presence of a base such as triethylamine and in a solvent, such as dimethylformamide, to provide

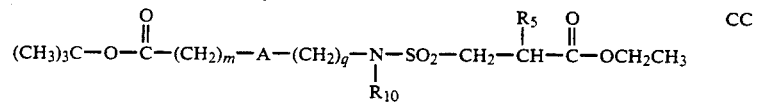

which is saponified with aqueous sodium hydroxide to provide, after acidification, the acid

CCI

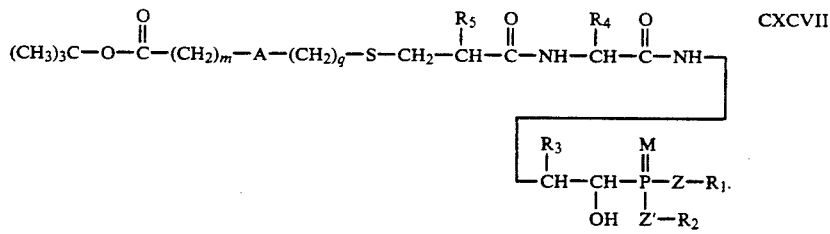

The compound of formula CXCIX is treated as described above for the compound CLXXXVIII to provide the corresponding compounds of formula I for which R₆ can be

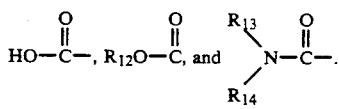

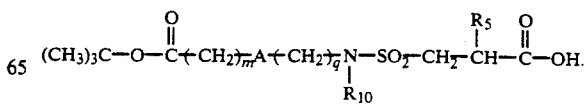

The acid of formula CCI is coupled to the amine of formula III to give

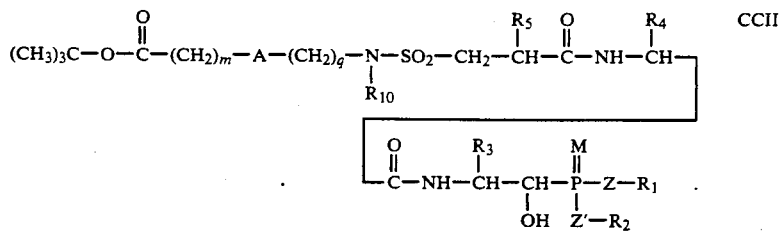

The compound of formula CCII is treated as described above for the compound CLXXXVIII to provide the corresponding compounds of formula I for which $R_6$ can be

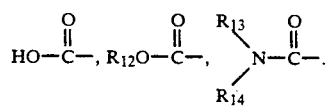

To make compounds of formula I wherein Y is $-CH_2-$, X is

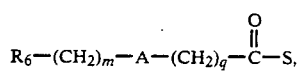

the previously described compound of formula CXXI is treated with mercaptoacetic acid to give

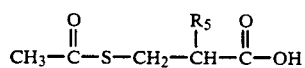

which is coupled to the amine of formula III to provide a compound of the formula

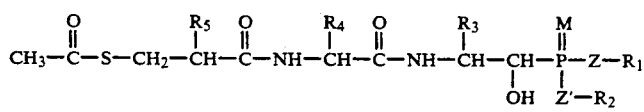

The compound of formula CCIV is then treated with aqueous ammonium hydroxide in a solvent, such as methanol, or with mercuric trifluoroacetate in tetrahydrofuran followed by treatment with hydrogen sulfide gas, to provide the free sulfhydryl compound

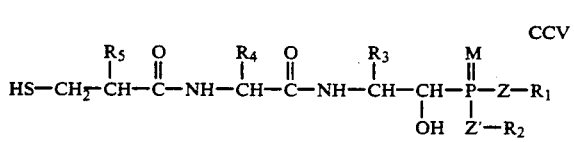

which is reacted with the acid of formula CLXXXIII using dicyclohexylcarbodiimide and dimethylaminopyridine in a solvent, such as dichloromethane, to provide a compound of the formula

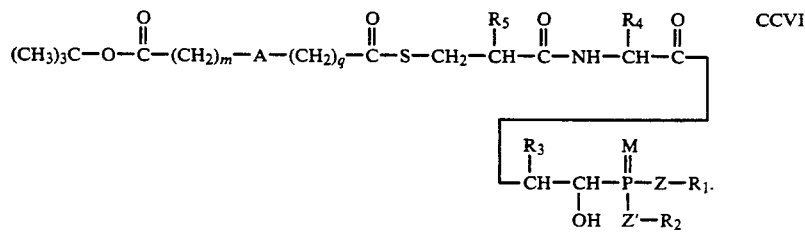

The compound of formula CCVI is treated as described above for the compound III to provide the corresponding compounds of formula I for which $R_6$ can be

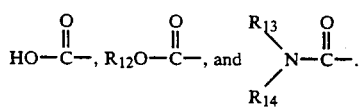

To make compounds of formula I wherein Y is $-CH_2-$ and X is

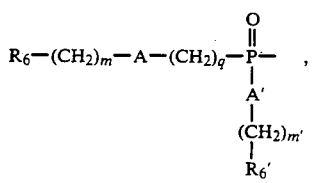

where $R_6$ is

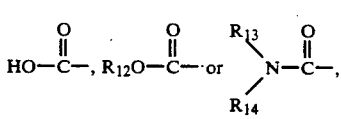

the tosylate of formula CXCIV is treated with sodium bromide in acetone to provide a compound of the formula

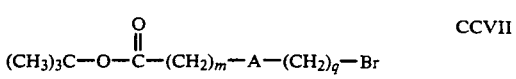

which can be reduced with lithium aluminum hydride in a solvent, such as tetrahydrofuran, to provide the compound HO—CH$_2$—(CH$_2$)$_m$—A—(CH$_2$)$_q$—Br.  CCVIII The alcohol CCVIII can be treated with benzyl bromide and sodium hydride in tetrahydrofuran to afford the protected alochol of the formula

—CH$_2$—O—CH$_2$—(CH$_2$)$_m$—A—(CH$_2$)$_q$—Br  CCIX which is converted to its corresponding Grignard reagent and reacted with dimethylchlorophosphite to provide

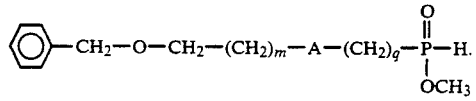 CCX

The compound of formula CCX is treated with a Grignard reagent of formula CXXXVII to provide a compound of the formula

CCXI

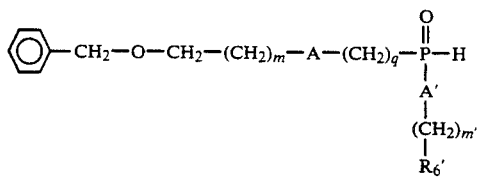

which is reacted with the acrylic acid of formula CXXI in dichloromethane in the presence of bis(trimethylsilyl)trifluoroacetamide to provide a compound of the formula

CCXII

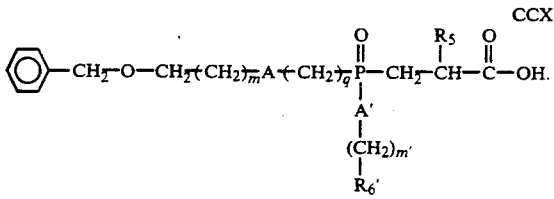

The compound of formula CCXII is esterified using methyl iodide and sodium bicarbonate in dimethylformamide, then reduced using hydrogen and a palladium catalyst to provide the alcohol of the formula

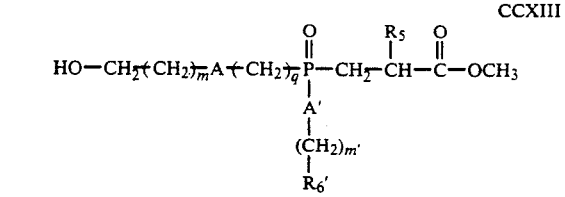 CCXIII which is oxidized to a carboxylic acid using a reagent, such as ruthenium trichloride and sodium meta-periodate in a solvent mixture consisting of carbon tetrachloride, acetonitrile and water. The resulting acid is converted to the corresponding t-butyl ester using t-butanol and dicyclohexylcarbodiimide and dimethylaminopyridine to give a compound of formula

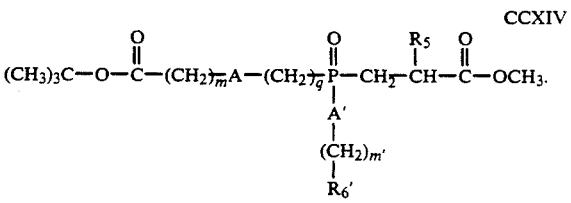 CCXIV

The compound of formula CCXIV is saponified using aqueous sodium hydroxide followed by acidification to yield the corresponding acid which is coupled to the amine of formula III to provide

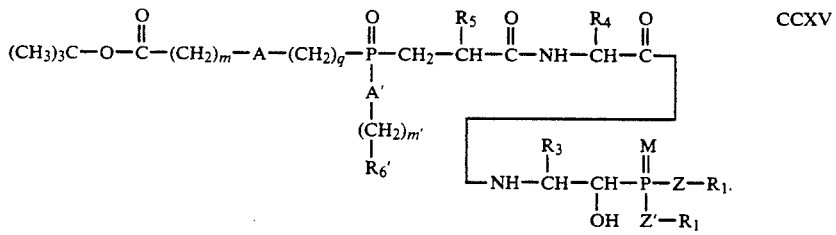 CCXV

The compound of formula CCXV is treated as described above for the compound CLXXXVIII to provide the corresponding compounds of formula I for which R$_6$ can be

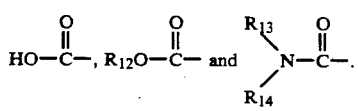

To make compounds of formula I wherein Y is —CH$_2$— and X is

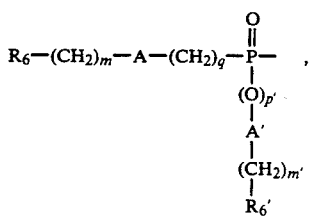

and p' is one and R$_6$ can be

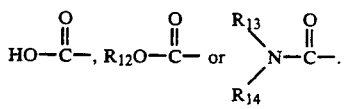

the compound of formula CCX is hydrolyzed with aqueous sodium hydroxide, then coupled to an alcohol of formula CXXVIII using dicyclohexylcarbodiimide and dimethylaminopyridine in a solvent, such as dichloromethane, to provide a compound of the formula

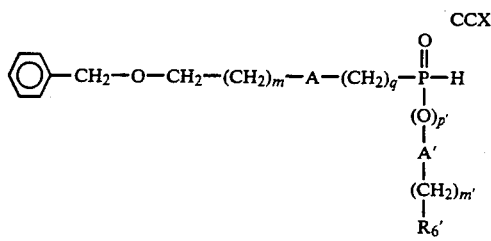

which can be converted to the corresponding compounds of formula I in the manner described previously for compounds of formula CCXI.

To make compounds of formula I wherein Y is —CH$_2$— and X is

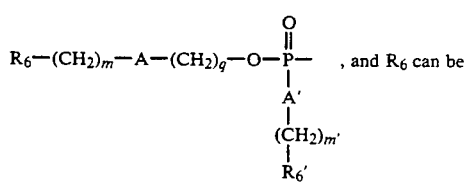

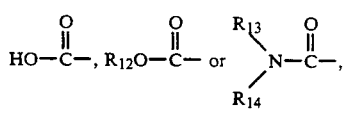

the compound of formula CXLII is hydrolyzed with aqueous sodium hydroxide, then coupled to the alcohol of the formula

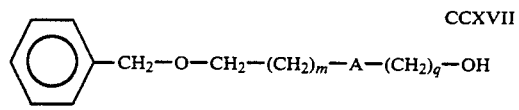

using dicyclohexylcarbodiimide and dimethylaminopyridine in a solvent, such as dichloromethane, to provide a compound of the formula

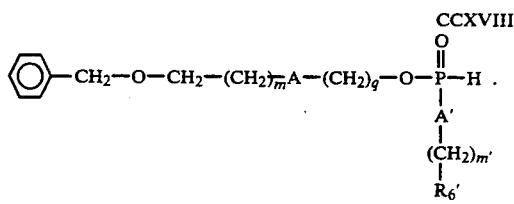

The alcohol of formula CCXVII may be prepared by treating the alcohol of formula CXCI with acetic anhydride in pyridine to provide the compound of the formula

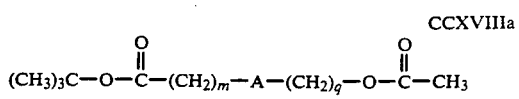

which is treated with trifluoroacetic acid to remove the t-butyl ester and the resulting acid group is selectively reduced using diborane to the alcohol of the formula

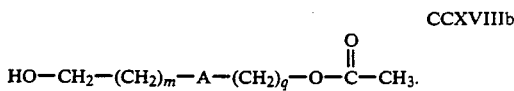

The compound of formula CCXVIIIb is treated with benzyl bromide and sodium hydride in a solvent such as tetrahydrofuran, followed by subsequent reduction of the acetate ester group with a reagent, such as lithium aluminium hydride in tetrahydrofuran. Compounds of formula CCXVIII can be converted to the corresponding compounds of formula I in the manner described previously for compounds of formula CCXI.

To make compounds of formula I wherein Y is —CH$_2$— and X is

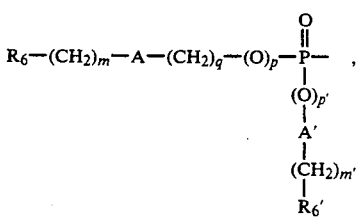

and p' is one and R$_6$ can be

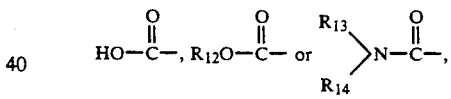

the alcohol of formula CCXVII is reacted with phosphorous trichloride, in the presence of triethylamine to provide, after hydrolytic workup, a compound of the formula

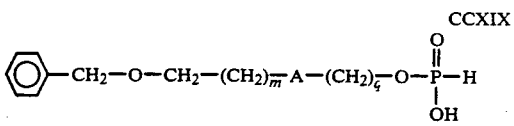

which is coupled to an alcohol of formula CXXVIII using dicyclohexylcarbodiimide and dimethylaminopyridine in a solvent, such as dichloromethane, to provide a compound of the formula

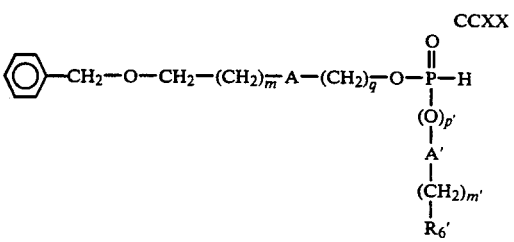

which can be converted to the corresponding compounds of formula I in the manner described previously for compounds of formula CCXI.

To make a compound of formula I wherein Y is —NH— and X is

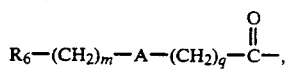

and $R_6$ can be

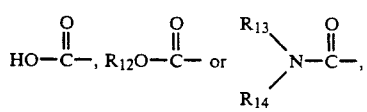

the acid of formula CLXXXIII is coupled with the previously described amine of formula CLIV using dicyclohexylcarbodiimide and hydroxybenzotriazole in a solvent such as dimethylformamide to provide the compound of the formula

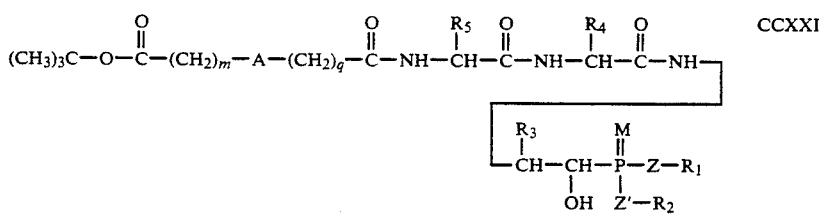

which can be converted to the corresponding compounds of formula I as described for the compound of formula CLXXXVIII.

To make a compound of formula I wherein Y is —NH—, X is

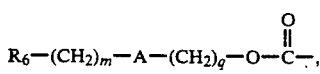

and $R_6$ can be

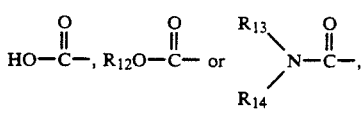

the alcohol of formula CXCI is treated with p-nitrophenylchloroformate to provide the intermediate compound of the formula

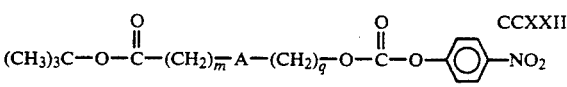

which is acylated with the amine of formula CLIV in a solvent, such as dimethylformamide, using a base, such as triethylamine, providing the compound of the formula

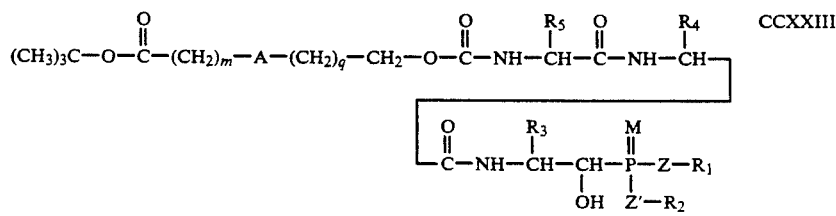

which can be converted to the corresponding compounds of formula I as described for the compound of formula CLXXXVIII.

To make a compound of formula I wherein Y is —NH—, X is

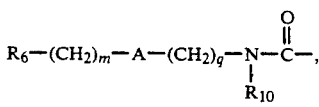

and $R_6$ can be $HO-\overset{O}{\underset{\|}{C}}-$, $R_{12}O-\overset{O}{\underset{\|}{C}}-$ or $\overset{R_{13}}{\underset{R_{14}}{\diagup}}N-\overset{O}{\underset{\|}{C}}-$, the amine of the formula CXCV is treated with pnitrophenylchloroformate to provide the compound of formula

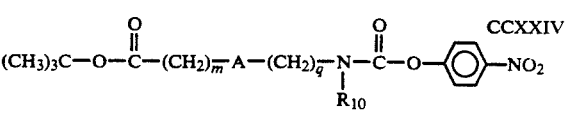

which is acylated with the amine of formula CLIV in a solvent, such as dimethylformamide, using a base, such as triethylamine, providing the compound of the formula

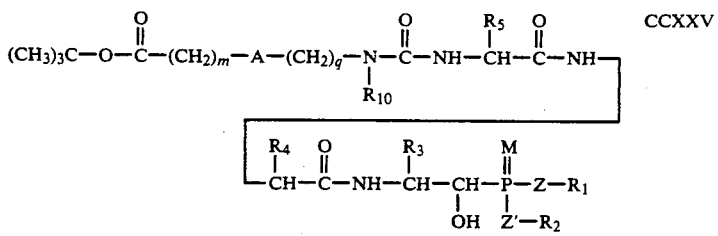

CCXXV which can be converted to the corresponding compounds of formula I as described for the compound of formula CLXXXVIII.

To make compounds of formula I wherein Y is —NH—, X is $R_6$—$(CH_2)_m$—A—$(CH_2)_q$—$SO_2$—, and $R_6$ can be

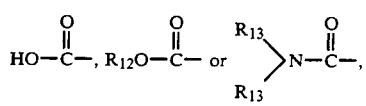

the tosylate of formula CXCIV is treated with mercaptoacetic acid in the presence of a base, such as triethylamine, to form the compound of the formula

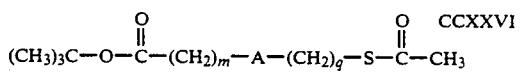

CCXXVI which is treated with aqueous ammonium hydroxide to yield the compound of the formula

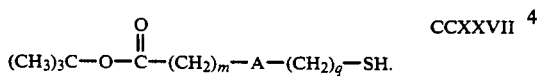

CCXXVII

The compound of formula CCXXVII is treated with chlorine gas in a solvent, such as aqueous acetic acid, to give the compound of the formula

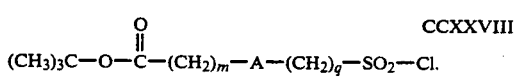

CCXXVIII

Treatment of the amine CLIV with compound CCXXVIII in dimethylformamide in the presence of a base, such as triethylamine, provides the compound of the formula

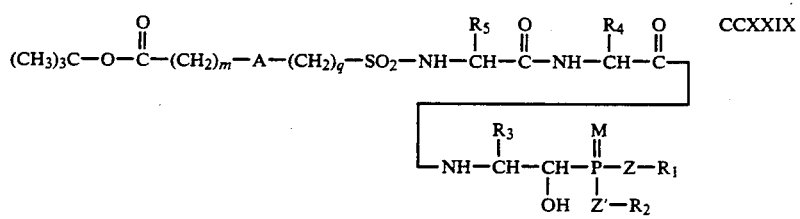

CCXXIX which can be converted to the corresponding compounds of formula I as described for the compound of formula CLXXXVIII.

To make a compound of formula I wherein Y is —O— and X is

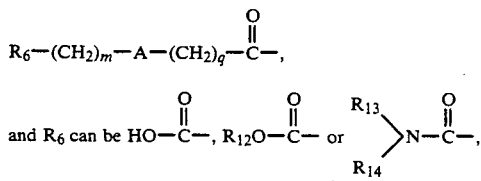

the alcohol of formula CLXII is coupled with the previously described acid of formula CLXXXIII using dicyclohexylcarbodiimide and dimethylaminopyridine in a solvent, such as dichloromethane, to provide a compound of the formula

CCXXX

When the protecting group (Prot') is benzyl, the compound of formula CCXXX is reduced by treatment with hydrogen in the presence of a palladium catalyst in a solvent, such as methanol to provide the corresponding free acid which is coupled to an amine of formula III using dicyclohexylcarbodiimide and hydroxybenzotriazole in a solvent, such as dimethylformamide, to provide the compound of the formula

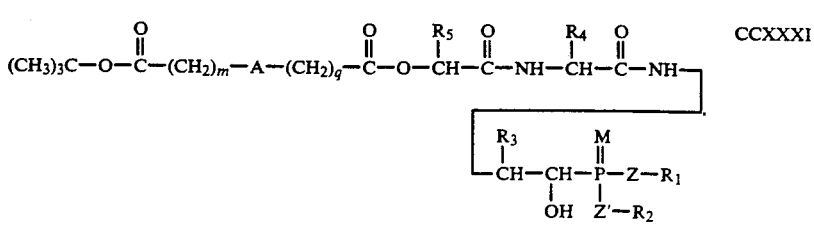

CCXXXI which can be converted to the corresponding compounds of formula I as described for the compound of formula CLXXXVIII.

To make a compound of formula I wherein Y is —O— and X is

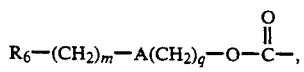

the previously describedc compound of formula CLXVI is treated with the alcohol of formula CXCI in a solvent, such as dimethylformamide using a base, such as triethylamine, and dimethylaminopyridine as a catalyst, to provide the compound

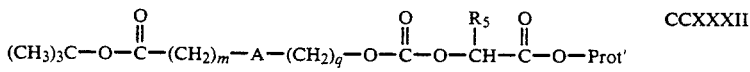

which can be converted to the corresponding compounds of formula I as described for the compound of formula CCXXX.

To make a compound of formula I wherein Y is —O— and X is

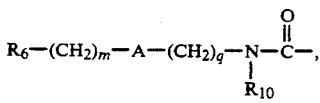

and $R_6$ can be

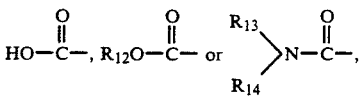

the amine of formula CXCV is reacted with the compound of formula CLXVI to provide the compound

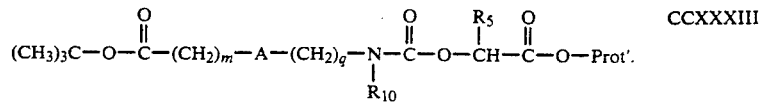

When the protecting group (Prot') is benzyl, the compound of formula CCXXXIII is reduced with hydrogen in the presence of palladium catalyst in a solvent such as methanol to provide the corresponding free acid, which is coupled to an amine of formula III using dicyclohexylcarbodiimide and hydroxybenzotriazole in a solvent, such as dimethylformamide, to provide the compound of the formula

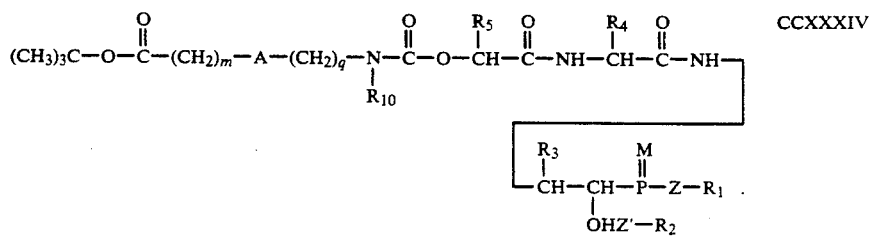

The compound of formula CCXXXIV can be converted to the corresponding compounds of formula I in the manner described for compounds of the formula CLXXXVIII.

To make a compound of formula I wherein Y is —O— and X is $R_6$—$(CH_2)_m$—A—$(CH_2)_q$—, and $R_6$ can be

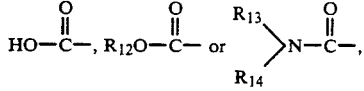

the alcohol of formula CLXII is treated with sodium hydride in a solvent, such as tetrahydrofuran, to form an intermediate alkoxide which is directly reacted with the alkyl bromide of the formula CCIX to provide the compound of the formula

CCXXXV

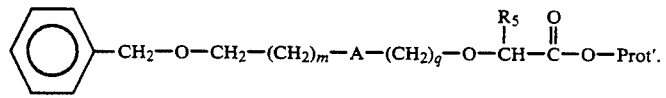

The benzyl group is reduced using hydrogen and palladium catalyst and the resulting alcohol is oxidized using ruthenium trichloride as described above to provide the acid of the formula

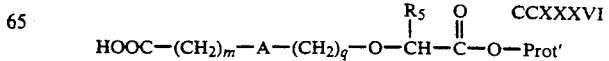

which is converted to an ester of the formula

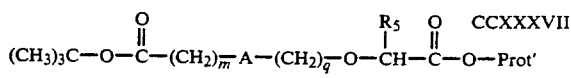

using t-butanol and dicyclohexylcarbodiimide in the presence of hydroxybenzotriazole.

The compound of formula CCXXXVII can be converted to the corresponding compounds of formula I in the manner described for compounds of formula CCXXXIII, except that the protecting group, Prot', should be a methyl ester that is removed by saponification.

To make compounds of formula I where Y is —O— and X is

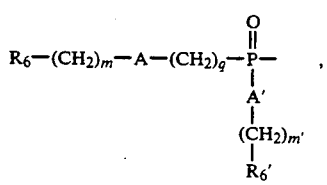

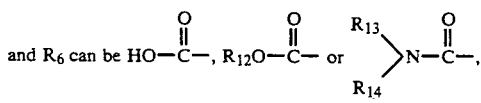

compounds of formula CCXI are treated with phosphorous pentachloride to provide the phosphinyl chloride of the formula

CCXXXVIII

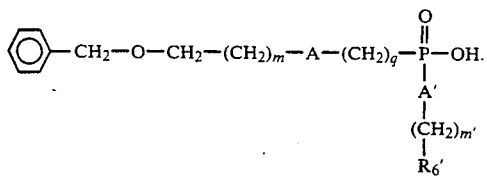

The compound of the formula CCXXXVIII is then coupled to the alcohol of formula CLXII in a solvent, such as dichloromethane, using dicylcohexylcarbodiimide and dimethylaminopyridine to give a compound of the formula

CCXXXIX

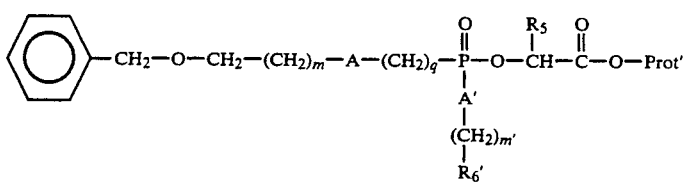

which is saponified to the corresponding acid

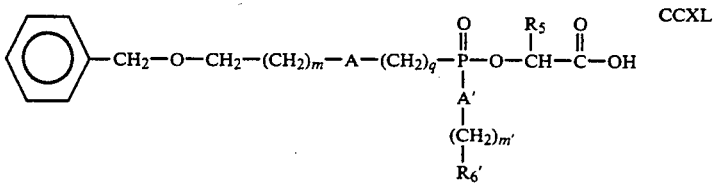

which can be converted to the corresponding compounds of formula I in the manner described above for compounds of the formula CCXII.

To make compounds of formula I where Y is —O— and X is

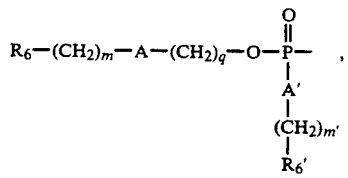

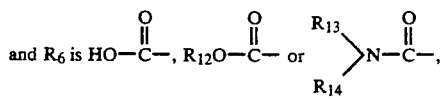

the compound of formula CLXXIV is reacted with the alcohol of formula CCXVII in a solvent, such as dichloromethane using dicyclohexylcarbodiimide and dimethylaminopyridine to form the compound of the formula

CCXLI

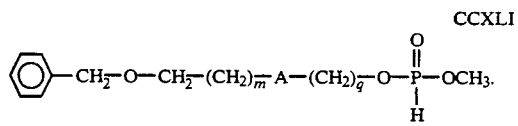

The compound of formula CCXLI is reacted with a Grignard reagent of formula CXXXVII to provide a compound of the formula

CCXLII

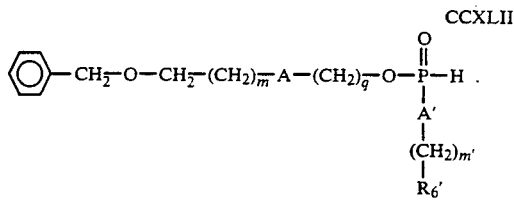

The compound of formula CCXLII is treated with thionyl chloride to provide an intermediate phosphonyl chloride which is coupled to an alcohol of formula CLXII in a solvent such as methylene choride in the presence of triethylamine and dimethylaminopyridine to provide a compound of the formula

CCXL

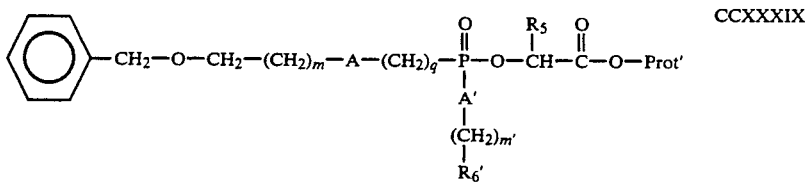

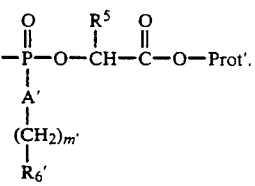  CCXLIII

The compound of formula CCXLIII is converted to the corresponding compounds of formula I in the manner as described above for compounds of formula CCXXXIX.

To make compounds of formula I where Y is —O— and X is

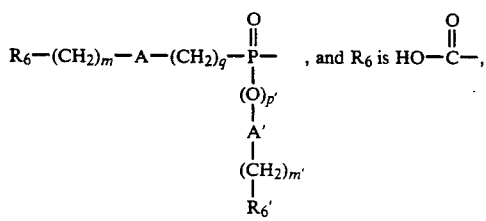, and $R_6$ is HO—C—,

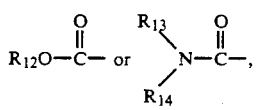

the compound of formula CLXXVIII is reacted with the Grignard reagent derived from the previously described alkyl halide of formula CCIX to give the compound of the formula

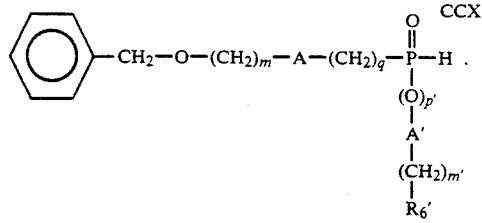  CCXLIV

The compound of formula CCXLIV is converted to the corresponding compounds of formula I in the manner as described above for compounds of formula CCXLII.

In the above reactions, if any of $R_3$, $R_4$ and $R_5$ are —$(CH_2)_n$—aryl wherein aryl is phenyl, 1-naphthyl, 2-naphthyl substituted with one or more hydroxy or amino groups, —$(CH_2)_n$—heterocyclo wherein heterocyclo is an imidazolyl,

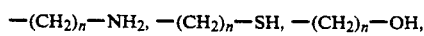

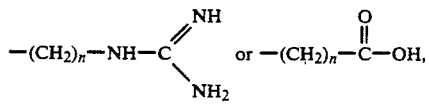

then the hydroxyl, amino, imidazolyl, mercaptan, carboxyl, or guanidinyl function should be protected during the reaction. Suitable protecting groups include benzyloxycarbonyl, t-butoxycarbonyl, benzyl, benzhydryl, trityl, tosyl, etc., and nitro in the case of guanidinyl. The protecting group is removed by hydrogenation, treatment with acid, or by other known means following completion of the reaction.

The various peptide intermediates employed in above procedures are known in the literature or can be readily prepared by known methods. See for example, the Peptides, Volume 1, "Major Methods of Peptide Bond Formation", Academic Press (1979).

Preferred compounds of this invention are those of formula I wherein $R_3$ is straight or branched chain lower alkyl of 3 to 5 carbons, —$(CH_2)_n$—cyclopentyl, —$(CH_2)_n$—cyclohexyl, or

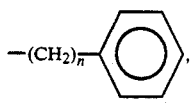

wherein n is an integer from 1 to 3;

$R_4$ is hydrogen, straight or branched chain lower alkyl of up to 5 carbons, —$(CH_2)_4$—$NH_2$,

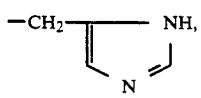

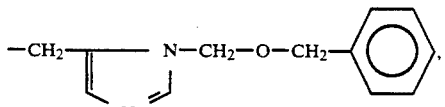

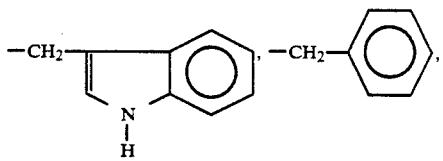

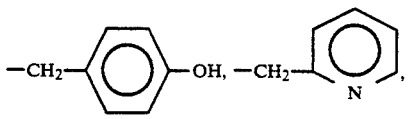

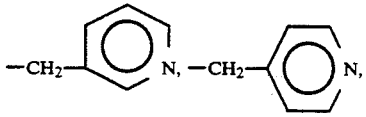

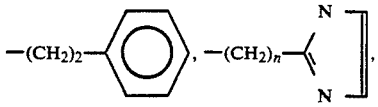

-continued
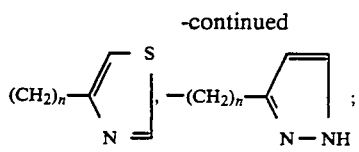
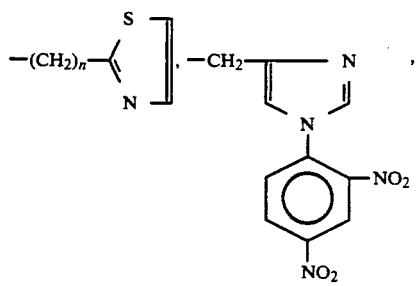
—CH₂—CH(CH₃)₂, —CH₂—CH₂—CH₂—CH₃,
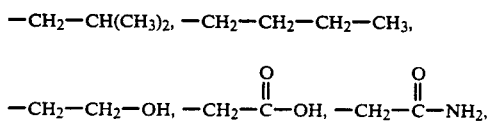
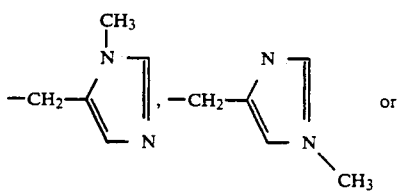 or
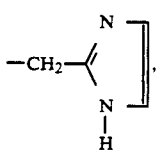
wherein
n is an integer from 1 to 3;
R₅ is straight or branched chain lower alkyl of up to 5 carbons,
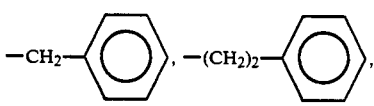
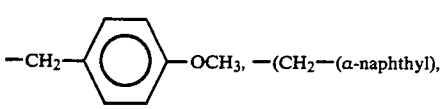
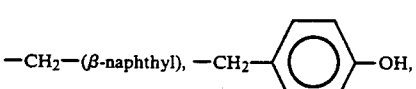
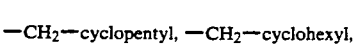
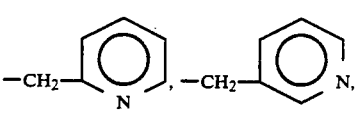
-continued
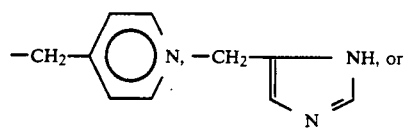
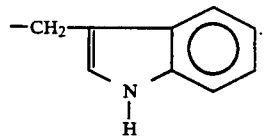
Most preferred are those compounds of formula I wherein
when r is one,
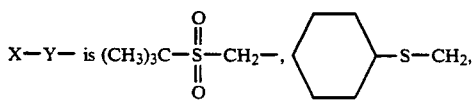
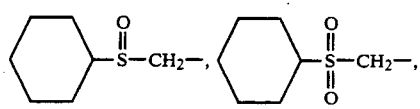
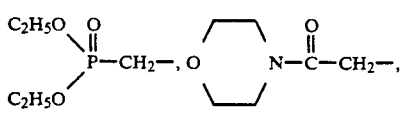
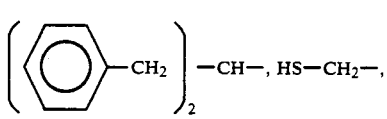
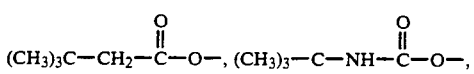
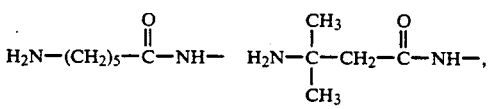
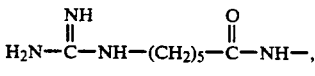
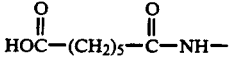
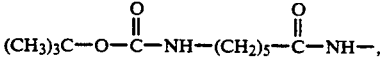
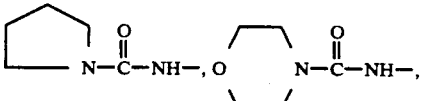
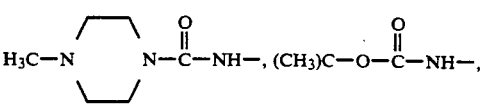

-continued

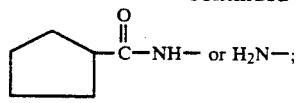

when r is zero, X—Y— is (CH$_3$)$_3$C—O—C(=O)—NH—,

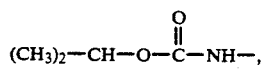

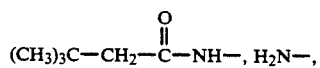

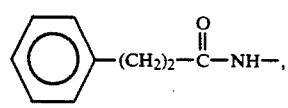

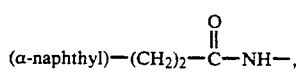

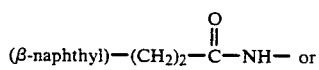

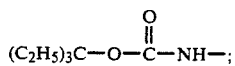

R$_1$ and R$_2$ are independently selected from hydrogen, —CH$_3$, —CH$_2$CH$_3$, —CH(CH$_3$)$_2$, —CH$_2$—CH(CH$_3$)$_2$, —CH$_2$—C(CH$_3$)$_3$,

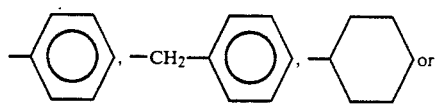

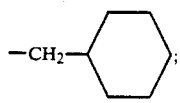

R$_3$ is 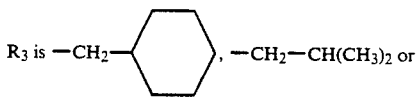

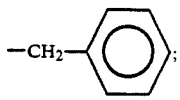

R$_4$ is 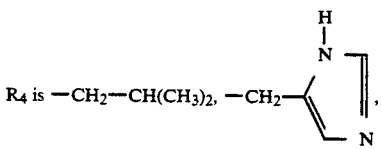

—CH$_2$—CH$_2$—CH$_2$—CH$_3$, —CH$_2$—CH$_2$—OH,

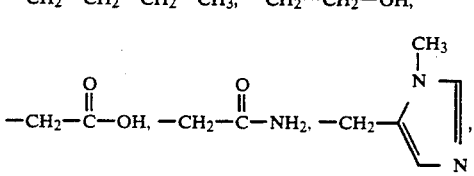

-continued

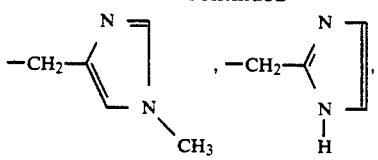

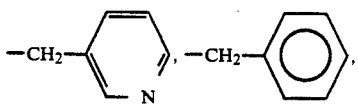

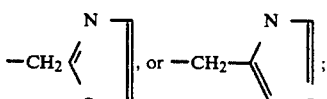

R$_5$ is 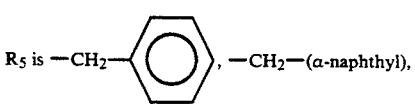

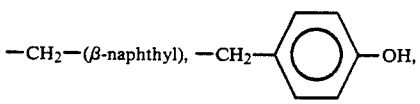

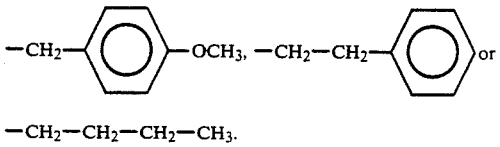

—CH$_2$—CH$_2$—CH$_2$—CH$_3$.

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

It should be understood that the present invention is meant to include ester, ether, ketal or acetal derivatives of the alcohol of formula I. Such derivatives for compounds containing an hydroxyl group have been documented in *Design of Prodrugs*, edited by H. Bundgard, (Elsevier, 1985) and *Methods in Enzymology*, Vol. 42, p. 309–396, edited by K. Widder et al., (Academic Press, 1985). Thus, the ester, ether, ketal or acetal derivatives of the alcohols of formula I are useful, for example, as prodrugs. Additionally, the corresponding alcohol intermediates throughout the above methodology may also be ester, ether, ketal or acetal derivatives. The preparation of such compounds is accomplished by methods common in the art.

The compounds of formula I contain asymmetric centers when any or all of R$_3$, R$_4$ and R$_5$ are other than hydrogen and at the carbon to which the —OH group is attached. Thus, the compounds of formula I can exist in diastereoisomeric forms or in mixtures thereof. The above-described processes can utilize racemates, enantiomers or diastereomers as starting materials. When diastereomeric products are prepared, they can be separated by conventional chromatographic or fractional crystallization methods.

The compounds of this invention including pharmaceutically acceptable salts thereof are useful cardiovascular agents. They inhibit the conversion of angiotensinogen to angiotensin I and therefore are useful in reducing or relieving disorders characterized by excessive angiotensin activity. The action of the enzyme renin on angiotensinogen produces angiotensin I which in turn is converted by the angiotensin converting enzyme (ACE) to angiotensin II. The latter is an active pressor substance which has been implicated as the causative agent in several forms of hypertension and other cardiovascular disorders in mammalian species, e.g. humans. The compounds of this invention intervene in the angiotensinogen→(renin)→angiotensin I→ (ACE)→angiotensin II sequence by inhibiting renin and reducing or eliminating the formation of the pressor substance angiotensin II.

As a result of this action, the compounds of this invention possess useful antihypertensive activity and are useful in any situation where the reduction of the levels of active renin, angiotensin I or angiotensin II would be beneficial. For example, the compounds of this invention are also useful in the treatment of congestive heart failure, renin dependent hypoaldosteronism, myocardial infarction, and renal disorders such as diabetic nephropathy. These compounds may also be useful as adjuncts in the treatment of other disorders such as glaucoma and scleroderma and as a diagnostic agent in determining the presence of renin related disorders such as hypertension.

Thus, the administration of a composition containing one (or a combination) of the compounds of this invention is useful in treating the angiotensin related disorders described above. For example, the daily administration of from about 0.5 to about 100 mg/kg of body weight in a single dose or divided into two to four doses is useful in reducing blood pressure in humans. Of course, the exact dose employed will vary according to the compound selected and the method of administration, i.e. the preferred intravenous dose is below about 1 mg/kg/day and the preferred oral dose is from about 10 to about 50 mg/kg/day. In addition to oral and intravenous forms of administration, the compounds of this invention can be formulated in compositions suitable for subcutaneous, transdermal, intramuscular, or intranasal administration. Suitable oral compositions include tablets, capsules, and elixirs and suitable parenteral compositions include sterile solutions or suspensions. From about 10 to about 100 mg of a compound of this invention is formulated with one or more physiologically acceptable vehicles, carriers, excipients, binders, preservatives, stabilizers, flavoring agents, etc. in a unit dose form as called for by accepted pharmaceutical practice.

The compounds of this invention are additionally useful when employed in combination with one or more other pharmaceutically active cardiovascular agents. Such combination may be employed as a fixed dose combination or as separate doses administered concomitantly. Examples of suitable cardiovascular agents include diuretics such as the thiazide diuretics, e.g., chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, delapril, pentopril, quinapril, ramipril, lisinopril, and salts of such compounds, a thromboxane synthetase inhibitor, a thromboxane receptor antagonist, a calcium channel blocking agent such as diltiazem, nifedipine, etc., a potassium channel activator, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), α- and β-adrenergic receptor blocking agents such as propanolol, nadolol, metoprolol, etc., antifibrillatory agents, neutral endopeptidase inhibitors, cardiotonic agents, etc. Such combination products if formulated as a fixed dose employ the compounds of this invention within the dose range described above and the other pharmaceutically active agent within its approved dose range.

In addition to the above described renin inhibition activity, the compounds of this invention are also inhibitors of viral proteases. It has been shown that, for example, retroviral protease activity is essential to the infectivity of the AIDS virus. Thus, the inhibition of such protease may provide a means of inhibiting the ability of the virus to replicate and may be useful in treating diseases caused by retroviruses which are dependent on one or more proteases for their virulence. This would include HTLV-I and HTLV-III. A suitable dose for this purpose would be from about 1 to about 500 mg/kg/day.

The present invention will now be described by the following examples, however, the invention should not be limited to the details therein.

EXAMPLE 1

[(1,1-Dimethylethoxy)carbonyl]-N-[1-(cyclohexylmethyl)-2-(dimethoxyphosphinyl)-2-hydroxyethyl]-L-leucinamide, Isomer A

A.

(S)-α-[[(1,1-Dimethylethoxy)carbonyl]amino]-cyclohexanepropanoic acid

Platinum oxide catalyst (5 g) is added to a solution of N-[(1,1-dimethylethoxy)carbonyl]-L-phenylalanine (120 g, 0.452 mole) in absolute ethanol (1 l). The mixture is placed on a Parr reduction apparatus at 50 lb pressure. The absorption of hydrogen is rapid and the hydrogen reservoir needs continued refilling. The reduction proceeds overnight and after 20 hours is completed. The mixture is filtered through Celite and concentrated in vacuo to give 124.4 g of the title A compound as a glassy solid colorless residue; $[α]_D = -9.5°$ (c=1, methanol). TLC (silica gel; toluene:acetic acid, 4:1) $R_f = 0.62$.

B. (S)-α-8 [(1,1-Dimethylethoxy)]carbonyl]amino]-N-methoxy-N-methylcyclohexanepropanamide The title A compound (22.6 g, 83.3 mmole) is dissolved in tetrahydrofuran (250 ml) under a blanket of argon at 26°. Carbonyldiimidazole solid (16 g, 98.7 mmole) is added in portions over one minute. Moderate gas evolution begins shortly after the addition is completed. The mixture remains colorless throughout. The mixture is stirred for 30 minutes at 25° during which time it remains clear and colorless. O,N-Dimethylhydroxylamine hydrochloride (11.5 g, 118 mmole) is then added in a single portion followed immediately by triethylamine (17.5 ml, 125 mmole) in a single portion.

Following the triethylamine addition a white precipitate forms. The mixture is stirred for 3 hours at 25°, after which it is poured into 1N hydrochloric acid (400 ml) and extracted with ether (3×200 ml). The colorless extracts are combined and washed with saturated sodium bicarbonate solution (2×200 ml), dried over anhydrous magnesium sulfate, and concentrated to give 24.2 g of the title B compound; $[\alpha]_D = -11.1°$ (c=7, methanol).

C. (S)-(2-Cyclohexyl-1-formylethyl)carbamic acid, 1,1-dimethylethyl ester

A 1M tetrahydrofuran solution of lithium aluminum hydride (85.4 ml, 85.4 mmol) was added dropwise over a period of 20 minutes to a solution of the title B compound (17.88 g, 56.94 mmol) in 350 ml ether at 0°. After an additional 30 minutes at 0°-2°, the reaction mixture was quenched with 250 ml 5% potassium hydrogen sulfate warmed to room temperature and the aqueous and organic layers were separated. The aqueous layer was diluted with 250 ml water and reextracted with ether (2×150 ml). The combined organic extracts were washed sequentially with 5% hydrochloric acid (150 ml), saturated aqueous sodium hydrogen carbonate (150 ml) and saturated aqueous sodium chloride (2×150 ml). After drying over anhydrous magnesium sulfate for 30 minutes, the ethereal solution was filtered through Celite and concentrated in vacuo to give 12.56 g of the title C compound. TLC, $R_f=0.63$ (silica gel, 1:1 hexane/ethyl acetate). $[\alpha]_D = -37.2°$ (c=5.59, $CH_3OH$).

D.
[(1S)-1-(Cyclohexylmethyl)-2-(dimethoxyphosphinyl)-2-hydroxyethyl]carbamic acid, 1,1-dimethyl-ethyl ester, diastereomeric mixture (12.7:1.0)

Dimethyl phosphite (4.383 ml, 47.8 mmol) and anhydrous potassium fluoride (6.109 g, 105.2 mmol) were added sequentially to a solution of the title C compound (12.2 g, 47.8 mmol) in dimethylformamide (120 ml). After vigorous stirring for 16 hours at room temperature, the reaction mixture was filtered and the filtrate concentrated in vacuo to afford 21.92 g of oily residue. Flash chromatographic purification afforded 13.12 g of the title D compound as a light yellow-colored solid whose diastereomer ratio was 12.7:1.0 as determined by a $^{31}p$ NMR. The product was suspended in hexane and filtered to give 8.683 g white solid, m.p. 77°-83°. $[\alpha]_D = -38.4°$ (c=1.14, $CH_3OH$).

E.
[(2S)-2-Amino-3-cyclohexyl-1-hydroxypropyl]phosphonic acid, dimethyl ester, monohydrochloride The title D compound (6.16 g, 16.9 mmol), was dissolved in a 1.2N solution of hydrochloric acid in ethyl acetate, reacted for 1 hour, concentrated and triturated with hexane, yielding 4.47 g of the title E compound.

F.
[(1,1-Dimethylethoxy)carbonyl]-N-[1-(cyclohexylmethyl)-2-(dimethoxvphosphinyl)-2-hydroxyethyl]-L-leucinamide, Isomer A A solution of Boc-L-leucine hydrate (3.18 g, 12.7 mmol) in dimethylformamide (25 mL) was added to a solution of the title E compound (3.50 g, 11.6 mmol) in dimethylformamide (25 mL) and cooled to 0° C. Hydroxybenzotriazole hydrate (1.95 g, 12.7 mmol), triethylamine (3.55 mL, 25.5 mmol) and 1-(3-dimethylaminopropyl)-3-ethylcarbodiimide hydrochloride (2.44 g, 12.7 mmol) were added sequentially. After 16 hours at 25° C. the reaction was quenched with pH 4.01 buffer solution and stirred for an additional 10 minutes. The reaction mixture was then extracted with ethyl acetate (2×200 mL) and the combined organic extracts were washed sequentially with saturated aqueous sodium hydrogen carbonate (2×150 mL), saturated aqueous sodium chloride (100 mL), dried and concentrated. Purification of the crude product (6.68 g) by flash chromatography and crystallized from hexane/ethyl acetate, yielded 2.90 g of the title compound, which is the major diastereomer A, m.p. 157° C.

Elemental analysis calc'd for $C_{22}H_{43}N_2O_7P$: C, 55.21; H, 9.06; N, 5.86; P, 6.47; Found: C, 55.34; H, 9 04; N, 5.78; P, 6.28.

EXAMPLE 2

[(1,1-Dimethylethoxy)carbonyl]-L-phenylalanyl-N-[(1S)-1-(cyclohexylmethyl)-2-(diethoxyphosphinyl)-2-hydroxyethyl]-L-leucinamide A.
[(1S)-1-(Cyclohexylmethyl)-2-(diethoxyphosphinyl)-2-hydroxyethyl]carbamic acid, 1,1-dimethylethyl ester A mixture of the aldehyde from Example 1, part C (2.55 g, 10 mmol), diethyl phosphonate (1.381 g, 10 mmol) and potassium fluoride (0.581 g, 10 mmol) in methylene chloride (40 ml) was stirred overnight at room temperature. A chromatography check after 14 hours revealed incomplete reaction and hence additional amounts of potassium fluoride (1.162 g, 20 mmol) and diethyl phosphonate (276 mg, 2 mmol) were added at this state. After another 4 hours stirring, the reaction mixture was filtered through celite, the filtrate diluted with methylene chloride (60 ml) and washed sequentially with water (2×25 ml), saturated sodium hydrogen carbonate (2×20 ml) and saturated sodium chloride (20 ml). Drying over sodium sulfate and concentration gave a residue which upon flash chromatographic purification yielded 3.04 g of the title A compound.

B.
[(2S)-2-Amino-3-cyclohexyl-1-hydroxypropyl]phosphonic acid, diethyl ester, monohydrochloride The title A compound (905 mg, 2.3 mmol) was dissolved in ethyl acetate (10 ml), the solution cooled to 0° and hydrochoric acid bubbled through it for ~15 minutes after which a chromatographic check revealed complete disappearance of starting material. The solution was concentrated, the residue redissolved in ~1:1 petroleum ether:ethyl acetate and reconcentrated to give a white solid which was dried overnight in vacuo.

C. t-Butyloxycarbonylphe nylalanyl leucine, methyl ester

To a mixture of t-butyloxycarbonyl-L-phenylalanine (13.265 g, 50 mmol), L-leucine methyl ester (9.085 g, 50 mmol) and hydroxybenzotriazole hydrate (7.65 g, 50 mmol) in 100 ml tetrahydrofuran at 0° was added dropwise a solution of diisopropylethylamine (8.7 ml, 50 mmol) in 50 ml tetrahydrofuran. This was followed by addition of dicyclohexylcarbodiimide (10.315 g, 50 mmol). The reaction was stirred at 0° for 2 hours and then left for overnight stirring at room temperature. The precipitated urea was filtered off, solvents stripped down and the residue diluted with ethyl acetate (200 ml). The organic solution was washed sequentially with saturated aqueous sodium hydrogen carbonate (2×100 ml), saturated aqueous sodium chloride (2×100 ml), dried over sodium sulfate, filtered and concentrated to give crude product which on crystallization from ethyl ether gave 7.05 g pure product. Concentration of the mother liquor solution followed by crystallization afforded 4.57 g crystalline product. An additional 1.35 g product was obtained by chromatographic purification of the crude product obtained from the left over mother liquors (40 g silica gel, 4:1 hexane/ethyl acetate). Thus, a total of 12.96 g of the title C compound was obtained, m.p. 104°-105°, $[\alpha]_D = -17.5°$ (c=1.2, MeOH).

Elemental analysis calc'd for $C_{24}H_{32}N_2O_5$: C, 64.30; H, 8.15; N, 7.14; Found: C, 64.12; H, 8.16; N, 7.02.

D. t-Butyloxycarbonylphenylalanyl leucine

Sodium hydroxide (1N, 12 ml, 12 mmol) was added to a 40 ml methanol solution of the title C compound ester (3.92 g, 10 mmol) and a chromatography check after one hour revealed total disappearance of starting material. The solvents were removed on rotary evaporator. The resulting white solid was suspended in 10 ml of water and 50 ml of ethyl acetate, acidified to pH 3.5 using 1N hydrochloric acid and the two layers separated. The aqueous layer was reextracted with ethyl acetate (3×30 ml), combined organic extracts dried over sodium sulfate and concentrated to give 3.54 g of the title D compound.

E.
[(1,1-Dimethylethoxy)carbonyl]-L-phenylalanyl-N-[(1S)-1-(cyclohexylmethyl)-2-(diethoxyphosphinyl)-2-hydroxyethyl]-L-leucinamide, The title D compound (2.04 g, 5.4 mmol) and the title B compound (1.786 g, 5.4 mmol) were dissolved in 20 ml dimethylformamide at 0° and hydroxybenzotriazole hydrate (826 mg, 5.4 mmol) was added to the solution. After 5 minutes, N,N-diisopropylethylamine (939 µl, 5.4 mmol) was added and this was followed immediately by addition of dicyclohexylcarbodiimide (1.112 g, 5.4 mmol). The reaction mixture was stirred at 0° for 2 hours and at room temperature overnight after which the precipitated urea was filtered off, the reaction mixture diluted with ethyl acetate (50 ml) and was sequentially with water (2×25 ml), 10% citric acid (25 ml), saturated sodium hydrogen carbonate (2×25 ml) and saturated sodium chloride (25 ml). Direct concentration wihtout drying afforded 3.585 g white solid which after flash chromatographic purification with 3:3:3:0.1 hexane/ether/ethyl acetate/acetic acid afforded the title compound as the following 116 mg minor diastereomer, m.p. 173°-175°, $[\alpha]_p = +10.0°$ (c=0.14, CH$_3$OH), 2.07 g ; mixed fractions and 1.11 g major diastereomer, which was recrystallized from isopropyl ether m.p. 136°-138° C., $[\alpha]_D = -48.0°$ (c=1.18, CH$_3$OH).

EXAMPLE 3

(Cyclopentylcarbonyl)-L-phenylalanyl-N-[1-cyclohexylmethyl)-2-(diethoxyphosphinyl)-2-hydroxyethyl]-L-leucinamide, acetate salt

A.
L-Phenylalanyl-N-[(1S)-1-(cyclohexylmethyl)-2-diethoxyphosphinyl)-2-hydroxyethyl]-L-leucinamide, monohydrochloride The major diastereomer A of Example 2, part E, (915.3 mg, 1.4 mmol) was dissolved in a solution of hydrochoric acid/acetic acid (7 mL), reacted for 0.5 hour at 25° C. and concentrated to dryness, yielding 815.9 mg of the title A compound.

B.
(Cyclopentylcarbonyl)-L-phenylalanyl-N-[1-cyclohexylmethyl)-2-(diethoxyphosphinyl)-2-hydroxyethyl]-L-leucinamide, isomer A, acetate salt Cyclopentane carboxylic acid (148 µl, 1.37 mmol) was added to a solution of the title A compound (809 mg, 1.37 mmol) in tetrahydrofuran (5.5 mL) and cooled to 0° C. Hydroxybenzotriazole hydrate (209.6 mg, 1.37 mmol), N,N-diisopropylethylamine (262.5 µl, 1.51 mmol) and dicyclohexylcarbodiimide (282.6 mg, 1.37 mmol) were added sequentially. After 48 hours at 0° C., the reaction mixture was filtered and concentrated to dryness. The residue was dissolved in ethyl acetate (40 mL), washed sequentially with 10% citric acid (15 mL), water (25 mL), saturated aqueous sodium hydrogen carbonate (15 mL), saturated aqueous sodium chloride (15 mL), dried and concentrated yielding 517 mg of crude compound. Purification by flash chromatography afforded 117 mg of impure product. Crystallization yielded 52 mg of the title compound, m.p. 180°-195° C., $[\alpha]_D = -36.7°$ (c 0.46, CH$_3$OH).

Elemental analysis calc'd for $C_{34}H_{56}N_3O_7P.0.5AcOH.1.0H_2O$: C, 60.24; H, 8.67; N, 6.02; Found: C, 60.25; H, 8.27; N, 6.05.

EXAMPLE 4

(1,1-Dimethylethoxy)carbonyl]-L-phenylalanyl-N-[(1S)-1-(cyclohexylmethyl)-2-hydroxy-2-(dimethoxyphosphinyl)ethyl]-L-leucinamide, isomer A The title E compound of Example 1 (810 mg, 2.7 mmol) was added to a solution of the title D compound of Example 2 (1.02 g, 2.7 mmol) in tetrahydrofuran (12 ml) and cooled to 0° C. Hydroxybenzotriazole hydrate (412 mg, 2.7 mmol), N,N-diisopropylethylamine (515 µL, 2.9 mmol) and dicyclohexylcarbodiimide (555 mg, 2.7 mmol) were added sequentially. After 18 hours at 0° C., the reaction mixture was filtered and concentrated. The residue was dissolved in methylene chloride (50 mL) and washed with 10% citric acid (2×30 mL), saturated aqueous sodium hydrogen carbonate (2×30 mL), saturated aqueous sodium chloride (30 mL), dried over sodium sulfate and concentrated, yielding 1.34 g of crude product. Purification by flash chromatography afforded 1.01 g of the title compound. Crystallization from hexane/ethyl acetate gave 440 mg of the pure title compound, Isomer A, m.p. 129°-130° C., $[\alpha]_D = 45.3°$ (c=0.44, CH$_3$OH).

Elemental analysis calc'd for $C_{31}H_{52}N_3O_8P.0.29H_2O$: C, 59.01; H, 8.40; N, 6.66; P, 4.91; Found: C, 59.01; H, 8.35; N, 6.79; P. 4.69.

EXAMPLE 5

(Cyclopentylcarbonyl)-L-phenylalanyl-N-[(1S)-1-(cyclohexylmethyl)-2-(dimethoxyphosphinyl)-2-hydroxyethyl]-L-leucinamide, Isomer A

A.
N-[(1S)-1-(Cyclohexylmethyl)-2-(dimethoxyphosphinyl)-2-hydroxyethyl]-L-leucinamide, monohydrochloride The title compound of Example 1 (2.29 g, 4.8 mmol) was dissolved in a 1.2N solution of hydrochloric acid in ethyl acetate (25 mL). After 1 hour, the reaction mixture was concentrated yielding 2.2 g of the title A compound.

Elemental analysis calc'd for $C_{17}H_{34}N_2O_5PCl \cdot 1.56\text{-}H_2O$: C, 46.70; H, 8.50; N, 6.32; P, 7.04; Found: C, 46.56; H, 8.45; N, 6.32; P, 6.83.

B. N-cyclopentylcarbonyl)-L-phenylalanine, methyl ester

To a solution of L-phenylalanine methyl ester hydrochloride (21.5 g, 100 mmol), 1-hydroxybenzotriazole hydrate (15.3 g, 100 mmol), and cyclopentanecarboxylic acid (18.8 mL, 100 mmol) in tetrahydrofuran (200 mL) at 0° C. were added triethylamine (14.0 mL, 100 mmol) and dicyclohexylcarbodiimide (20.6 g, 100 mmol). The resulting mixture was stirred for 18 hours at 25° C. and was then filtered. The filtrate was diluted with ethyl acetate and washed sequentially with 10% potassium hydrogen sulfate solution, saturated sodium bicarbonate solution, and brine, dried over anhydrous magnesium sulfate and concentrated to dryness. The residue was crystallized from ethyl acetate/hexane to give the title B compound (17.5 g), m.p. 72°-73° C., $[\alpha]_D = +1.0°$ (c=1.0, $CH_3OH$) Flash chromatography of the mother liquors gave an additional 4.15 g of pure material. Total yield: 21.6 g.

C. N-(Cyclopentylcarbonyl)-L-phenylalanine

To a solution of the title B compound (18.0 g, 65 mmol) in methanol (135 mL) was added 1.0 N sodium hydroxide solution (72 mL, 72 mmol). The mixture was stirred for 2 hours at 25° C., after which it was made acidic by addition of 1N hydrochloric acid. The mixture was partially concentrated in vacuo, after which the remaining aqueous mixture was extracted with ethyl acetate. The extract was dried over anhydrous magnesium sulfate and concentrated. The residue (17.4 g) was crystallized from ethyl acetate:hexane to give the title C compound (14.4 g), m.p. 102°-104° C., $[\alpha]_D = +25.6°$ (c=2, $CH_3OH$).

D. (Cyclopentylcarbonyl)-L-phenylalanyl-N-[(1S)-1-(cyclohexylmethyl)-2-(dimethoxyphosphinyl)-2-hydroxyethyl]-L-leucinamide, Isomer A The title A compound (1.7 g, 4.1 mmol) was added to a solution of the title C compound (1.07 g, 4.1 mmol) in dimethylformamide (16 mL) and cooled to 0° C. Hydroxybenzotriazole hydrate (627.3 mg, 4.1 mmol), triethylamine (628.5 μl, 4.5 mmol) and 1-(3-dimethylaminopropyl)-3-ethylcarbodiimide hydrochloride (785.9 mg, 4.1 mmol) were added sequentially. After 18 hours at room temperature, pH 4.01 buffer solution was added and the reaction mixture was stirred for 10 minutes. The resulting precipitate was filtered and washed sequentially with pH 4.01 buffer solution (3×60 mL), water (4×60 mL), saturated aqueous sodium hydrogen carbonate (4×60 mL) and dried in vacuo yielding 3.0 g of crude product. Purification by flash chromatography afforded 1.27 g of the pure title compound, m.p. 145°-147° C., $[\alpha]_D = -51.7°$ (c=0.97, $CH_3OH$).

Elemental analysis calc'd for $C_{32}H_{52}N_3O_7P \cdot 0.6H_2O$: C, 60.76; H, 8.48; N, 6.65; P, 4.90; Found: C, 60.93; H, 8.28; N, 6.62; P. 4.51.

EXAMPLE 6

(4-Morpholinylcarbonyl)-L-phenylalanyl-N-[(1S)-1-(cyclohexylmethyl)-2-(dimethoxyphosphinyl)-2-hydroxyethyl]-L-leucinamide, isomer A

A. N-[(4-Nitrophenoxy)carbonyl]-L-phenylalanine, methyl ester

To a suspension of phenylalanine methyl ester hydrochloride (2.15 g, 10.0 mmols) in methylene chloride (40 mL) at −30° C. was added N-methylmorpholine (2.2 mL, 20 mmols) followed by p-nitrophenyl chloroformate (2.01 g, 10 mmols). The resulting mixture was stirred at −30° C. for 15 minutes, then for 15 minutes at 25° C., after which it was washed sequentially with 1N hydrochloric acid and saturated aqueous sodium bicarbonate solution, dried, and concentrated. The residue (2.96 g) was crystallized from acetonitrile to give the title A compound (1.22 g), m.p. 130°-131° C., $[\alpha]_D + 88°$ (c=1.5, $CHCl_3$). The mother liquor was chromatographed on silica gel (90 g), eluting with benzene:ethyl acetate (9:1) to give an additional 760 mg of the title A compound (total yield 1.98 g).

B. N-(4-Morpholinylcarbonyl)-L-phenylalanine, methyl ester

To a solution of the title A compound (3.44 g, 10 mmols) in toluene (40 mL) at 25° C. was added morpholine (1.1 mL, 12.5 mmol). The resulting mixture was stirred for 2 hours at 25° C., then at 100° C. for 5 hours, after which it was concentrated in vacuo. The residue was dissolved in ethyl acetate and the solution was washed with saturated potassium carbonate solution until the washes were colorless. The organic extract was dried over anhydrous mangesium sulfate and concentrated in vacuo. The residue was crystallized from ethyl acetate/hexane to give the title B compound (2.3 g), m.p 88°-91° C., $[\alpha]_D = -30.8°$ (c=0.6, $CH_3OH$)

C. N-(4-Morpholinylcarbonyl)-L-phenylalanine

A mixture of the title B compound (2.3 g, 7.8 mmols) and aqueous 1N sodium hydroxide solution (8.6 mL, 8.6 mmols) in methanol (12 mL) was stirred for 5 hours at 25° C., after which it was concentrated in vacuo. The residue was dissolved in water and washed with ethyl acetate. The aqueous layer was made acidic by addition of 1N hydrochloric acid solution and extracted with ethyl acetate. The extract was dried over anhydrous magnesium sulfate and concentrated to give the title C compound (2.2 g), $[\alpha]_D -23.8°$ (c=2, $CH_3OH$).

D. (4-Morpholinylcarbonyl)-L-phenylalanyl-N-[(1S)-1-(cyclohexylmethyl)-2-(dimethoxyphosphinyl)-2-hydroxyethyl]-L-leucinamide, isomer A The title C compound (993.5 mg, 3.42 mmol) was added to a solution of the title A compound of Example 5 (1.42 g, 3.42 mmol) in 17 ml of solvent and cooled to 0° C. Hydroxybenzotriazole hydrate (523.3 mg, 3.42 mmol), triethylamine (572.2 μl, 4.10 mmol), and 1-(3-dimethylaminopropyl)-3-ethylcarbodiimide hydrochloride (655.6 mg, 3.42 mmol) were added sequentially. After 20 hours at 25° C., a pH 4.01 buffer solution was added and the reaction mixture was allowed to stir for 10 minutes. The aqueous layer was extracted with ethyl ether (3×75 mL) and the combined organic portions were washed with saturated aqueous sodium hydrogen carbonate (75 mL), dried over sodium sulfate and concentrated yielding 1.8 g of crude product. Repeated purifications by flash chromatography finally afforded 674 mg of the pure title compound, m.p. 99°–105° C., $[\alpha]_D = -60°$ (c = 1.07, CH$_3$OH).

Elemental analysis calc'd for $C_{31}H_{51}N_4O_8P$: C, 58.29; H, 8.05; N, 8.77; P, 4.85; Found: C, 58.63; H, 8.18; N, 8.82; P, 4.63.

EXAMPLE 7

[(6-Amino-1-oxohexyl)-L-phenylalanyl]-N-[(1S)]-1-cyclohexylmethyl)-2-(dimethoxyphosphinyl)-2-hydroxyethyl]-L-leucinamide, isomer A, monohydrochloride

A. 6-[[(Phenylmethoxy)carbonyl]amino]hexanoic acid

To a solution of 6-aminocaproic acid (15 g, 0.114 mole) in a 5% aqueous solution of sodium hydroge carbonate (500 ml) and tetrahydrofuran (100 ml), was added benzylchloroformate (19.52 ml, 0.137 mole) dropwise over a 10 minute period. The reaction was allowed to stir at room temperature until carbon dioxide had ceased to eliminate (~24 hours). The reaction was concentrated in vacuo to remove tetrahydrofuran and the aqueous layer was extracted with ethyl acetate and concentrated again to remove organic residue and then acidified to pH 3 and extracted with ethyl acetate (4×), dried over anhydrous magnesium sulfate and concentrated to yield a clear oil. The product was crystallized from ethyl acetate:hexane (1:1). The white solid was recrystallized twice to yield 22.5 g of the title A compound.

B.
N-[6-[[(Phenylmethoxy)carbonyl]amino]-1-oxohexyl]-L-phenylalanine, methyl ester To a mixture of Z-aminocaproic acid (i.e. the title A compound) (18.6 g, 0.07), L-phenylalanine methyl ester hydrochloride (16.6 g, 0.077 mol), hydroxybenzotriazole hydrate (10.7 g, 0.07 mol) in 350 mL of dry tetrahydrofuran cooled in an ice bath was added N-methylmorpholine (7.1 g, 0.07 mol) followed by water soluble carbodiimide reagent, 1-(3-dimethylaminopropyl)-3-ethylcarbodiimide (13.5 g, 0.07 mol). After stirring cold for 4 hours, the reaction was allowed to warm to ambient temperature overnight. The reaction mixture was then concentrated in vacuo and next treated with ethyl acetate (400 mL) and pH 4 phosphate buffer (200 mL). The organic phase was rinsed with saturated aqueous sodium hydrogen carbonate solution until thin layer chromatography showed the absence of Z-aminocaproic acid, then with brine and dried over anhydrous magnesium sulfate hydrate. Removal of solvents gave 28 g of crude product. This crude product was absorbed onto Baker silica gel (50 g), then flash chromatographed on Merck silica gel (400 g) eluting with 1:1 ethyl acetate:hexane. Collection of the product, eluted in yellow colored fractions, gave 23.3 g of the title B compound as a solid, m.p. 83°–85° C.

Microanalysis calc'd for $C_{24}H_{30}N_2O_5$: C, 67.90; H, 7.09; N, 6.57; Found: C, 67.72; H, 6.92; N, 6.58.

C.
N-[6-[[(Phenylmethoxy)carbonyl]amino]-1-oxohexyl]-L-phenylalanine

To a solution containing the title B compound (23 g, 54 mmol) dissolved in 175 mL of methanol was added 1N aqueous sodium hydroxide solution (68 mL, 68 mmol). After stirring at room temperature for 2.5 hours, the reaction was concentrated in vacuo, then redissolved in 1500 mL of water, cooled in an ice bath and acidified to pH 3 by the addition of 1N hydrochloric acid. The filtered product was dried to finally yield 17.8 g of the title C compound as a solid, m.p. 119°–120° C.

Microanalysis calc'd for $C_{23}H_{28}N_2O_5 \cdot 0.6H_2O$: C, 65.26; H. 6.95; N, 6.62; Found: C, 65.16; H, 6.57; N, 6.61.

D.
[6-[[(Phenylmethoxy)carbonyl]amino]-1-oxohexyl]-L-phenylalanyl-N-[(1S)-1-(cyclohexylmethyl)-2-(dimethoxyphosphinyl)-2-hydroxyethyl]-L-leucinamide The title A compound of Example 5 (1.24 g, 3 mmol) was added to a solution of the title C compound (1.27 g, 3 mmol) in dimethylformamide (15 mL) and cooled to 0° C. Hydroxybenzotriazole hydrate 459 mg, 3 mmol), triethylamine (501.9 ml, 3.6 mmol) and 1-(3-dimethylaminopropyl)-3-ethylcarbodiimide hydrochloride (575.1 mg, 3 mmol) were added sequentially. After 16 hours at 25° C., pH 4.01 buffer solution was added and the reaction mixture was stirred for 10 minutes. The resulting precipitate was filtered and washed sequentially with pH 4.01 buffer (3×50 mL), water (3×50 mL), saturated aqueous sodium hydrogen carbonate (50 mL) and dried over sodium sulfate yielding 1.6 g of crude material. Purification by flash chromatography afforded 770 mg of slightly impure product and 566.1 mg of pure title D compound, which was characterized by $^{13}$MS and $^{13}$NMR.

E.
[(6-Amino-1-oxohexyl)-L-phenylalanyl]-N-[(1S)-1-(cyclohexylmethyl)-2-(dimethoxyphosphinyl)-2-hydroxyethyl]-L-leucinamide, isomer A, monohydrochloride A mixture of the title D compound (537 g, 0.69 mmol), palladium on carbon (209 mg) and 1N hydrochloric acid (759 ml, 0.75 mmol) in methanol (7 mL) was stirred under a hydrogen atmosphere for 16 hours, after which the reaction mixture was filtered and concentrated. Purification by flash chromatography and lyophilization gave give 390.5 mg of the title compound as a fluffy white solid, m.p. 99°–124° C., $[\alpha]_D = -41.6°$ (c=0.65, CH$_3$OH).

Elemental analysis calc'd for $C_{32}H_{56}N_4O_7PCl \cdot 1.3HCl$, $0.47H_2O$: C, 55.34; H, 8.30; N, 8.06; Cl, 6.63; P, 4.45 Found: C, 55.33; H, 8.18; N, 8.14; Cl, 6.67; P, 4.56.

EXAMPLE 8

(Cyclopentylcarbonyl)-L-phenylalanyl-N-[(1S)-1-(cyclohexylmethyl)-2-(dimethoxyphosphinyl)-2-hydroxyethyl]-L-histidinamide, isomer A monohydrochloride

A. L-Histidine, methyl ester, dihydrochloride

To a stirred solution (ice-bath) of L-histidine (38.75 g, 240 mmol) in methanol (500 ml), thionyl chloride (27.2 ml, 375 mmol) was added dropwise. After fifteen minutes the ice bath was removed and the reaction mixture was stirred at room temperature for one hour. Then after refluxing for 48 hours, it was concentrated in vacuo. The separated crystals were filtered using methanol for washing (48.93 g). The methanolic solution on dilution with ether afforded additional 10 g of the title A compound, m.p. 208°–209°, $[\alpha]_D = +10.1°$ (c=1.8, H$_2$O).

B. N,1-Bis[(1,1-dimethylethoxy)carbonyl]-L-histidine, methyl ester

To a suspension of the title A compound (24.2 g, 100 mmol) in methanol (80 ml) were added triethyl amine (28 ml, 200 mmol) and di-tert-butyl dicarbonate (48 g, 220 mmol). After 3.5 hours, it was filtered and the methanolic solution concentrated in vacuo. The residue was taken into chloroform and washed with 10% citric acid. The crude product on crystallization from isopropyl ether afforded 23.1 g of the title B compound, m.p. 88°-95° C., $[\alpha]_D = +25.4°$ (c=1.1, CCl$_4$). After evaporation and redissolution of the mother liquor (15.75 g) in methanol (50 ml) di-tert-butyl dicarbonate (10 g, 45.9 mmol) was added. After stirring the reaction mixture overnight it was evaporated, taken into chloroform and washed with 10% citric acid. The residue after chromatography over silica gel yielded 6.4 g of homogeneous title B compound.

C. N-[(1,1-Dimethylethoxy)carbonyl]-3-[(phenylmethoxy)methyl]L-histidine, methyl ester, monohydrochloride To a solution of the title B compound (24.7 g, 66.9 mmol) in dry methylene chloride (156 ml), benzylchloromethyl ether (11.6 ml, 88.6 mmol) was added and the reaction mixture stirred at room temperature for 5 hours. After concentration in vacuo and on dissolution in ethyl acetate (100 ml), the title C compound crystallized out (17.85 g, 65%), m.p. 152°-153° C., $[\alpha]_D -19.5°$ (c 1.8, CH$_3$OH).

D. 3-[(Phenylmethoxy)methyl]-L-histidine, methyl ester, monohydrochloride

The title C compound (11.4 g, 27.7 mmol) was dissolved in anhydrous hydrchloric acid in acetic aCid (60 ml, 1.5N) and kept at room temperature for 15 minutes. It was then evaporated in vacuo and the residue dissolved in hot isopropanol. After cooling, the separated crystals were filtered. Yield: 7.08 g (71 1), m.p. 173°-174°. An additional crop of 0.78 g was obtaied from mother liquor, m.p. 169°-170°.

E. N-[N-(Cyclopentylcarbonyl)-L-phenylalanyl]-3-[(phenylmethoxy)methyl]-L-histidine, methyl ester To a solution of the title D compound (12.7 g, 35 mmol), 1-hydroxybenzotriazole hydrate (5.36 g, 35 mmol), and the title C compound of Example 5 (9.15 g, 35 mmol) in tetrahydrofuran (140 mL) at 0° C. were added triethylamine (9.8 mL, 70 mmol) and dicyclohexylcarbodiimide (7.2 g, 35 mmol). The resulting mixture was stirred for 18 hours at 25° C., resulting in a non-stirrable solid mass. The mixture was diluted with ethyl acetate and filtered to give a white solid (26 g). The filtrate was washed with saturated sodium bicarbonate solution, dried over anhydrous magnesium sulfate, and concentrated to give a solid residue (8.42 g). Chromatography analysis of the solid removed by filtration indicated that it contained substantial amounts of the desired product. The solid was thus suspended in hot tetrahydrofuran (150 mL) and was filtered to give a white solid consisting of only dicyclohexyl urea. The filtrate (which contained the desired product) was concentrated and combined with the solid to give a total of 18.4 g crude product, which was further purified by flash chromatography on silica gel (1000 g), eluting with 200:20:6:11 ethyl acetate:pyridine:acetic acid:water. Fractions containing the desired product were combined and concentrated. The residue was crystallized from acetonitrile to give 12.4 g of the title E compound, m.p. 164°-165° C.

F. N-[N-(Cyclopentylcarbonyl)-L-phenylalanyl]-3-[(phenylmethoxy)methyl)-L-histidine To a solution of the title E compound (12.2 g, 23 mmol) in methanol (81 mL) at 25° C. was added 1.0N sodium hydroxide solution (25 mL, 25 mmol). The resulting mixture was stirred at 25° C. for 90 minutes, after which it was partially concentrated in vacuo. The remaining aqueous mixture was diluted with water (to 600 mL) and the pH was adjusted to 4.4 by addition of 1N hydrochloric acid (26 mL). The resulting white precipitate was collected by filtration, washed with water, and dried in vacuo to give 9.74 g of the title F compound, m.p. 195°-197° C., $[\alpha]_D = +25.6°$.

G. (Cyclopentylcarbonyl)-L-phenylalanyl-N-[(1S)-1-(cyclohexylmethyl)-2-(dimethoxyphosphinyl)-2-hydroxyethyl]-3-[(phenylmethoxy)methyl]-L-histidinamide The title F compound (1.73 g, 3.32 mmol) was added to a solution of the title E compound of Example 1 (1.20 g, 3.98 mmol) in dimethylformamide (15 mL) and cooled to 0° C. Hydroxybenzotriazole hydrate (558.7 mg, 3.65 mmol), triethylamine (696.5 µl, 4.98 mmol) and 1-(3-dimethylaminopropyl)-3-ethyl carbodiimide hydrochloride (699.8 mg, 3.65 mmol) were all added sequentially. After 16 hours at 25° C., pH 4.01 buffer solution was added and the reaction mixture was stirred for an additional 10 minutes. The aqueous portion was extracted with ethyl acetate (2×75 mL) and the combined organic portions were washed with saturated aqueous sodium hydrogen carbonate, dried over sodium sulfate and concentrated. Purification of the crude product 2.4 g) by flash chromatography yielded 1.32 g of the pure title G compound, which was characterized by MS and $^{13}$NMR.

H. (Cyclopentylcarbonyl)-L-phenylalanyl-N-[(1S)-1-(cyclohexylmethyl)-2-(dimethoxyphosphinyl)-2-hydroxyethyl]-L-histidinamide, isomer A monohydrochloride A mixture of the title G compound (1.24 g, 1.6 mmol), 20% palladium hydroxide on carbon (480 mg) and 1N hydrochloric acid (1.6 mL, 1.6 mmol) in methanol (11 ml) was stirred under hydrogen for 20 hours after which it was filtered and concentrated. Purification of the crude (1.17 g) by flash chromatography yielded a residue which was dissolved in water containing 1.1 mL of 1N hydrochloric acid, millipore filtered and lyophilized to give the title compound (541 mg) as a white fluffy solid, m.p. 110°-130° C., $[\alpha]_D = -14.5°$ (c=0.85, CH$_3$OH).

Analysis calc'd for $C_{32}H_{48}N_5O_7P \cdot 1.2HCl$, $0.68H_2O$: C, 54.86; H, 7.27; N, 10.00; Cl, 5.90; P, 4.42; Found: C, 55.05; H, 7.28; N, 9.89; Cl, 5.95; P. 4.56.

EXAMPLE 9

[(1,1-Dimethylethoxy)carbonyl]-N-[(1S)-1-(cyclohexylmethyl)-2-(dimethoxyphosphinyl)-2-hydroxyethyl]-L-histidinamide, isomer A, monohydrochloride

A.
N-[(1,1-Dimethylethoxy)carbonyl]-3-[(phenylmethoxy)methyl]-L-histidine The title C compound of Example 8 (18.66 g, 43.8 mmol) was dissolved in methanol (50 ml). Aqueous sodium hydroxide (1N, 92 ml) was added followed by water 83 ml). After keeping the reaction mixture at room temperature for 90 minutes it was further diluted by the addition of water (650 ml) and acidified to pH 4.5 using aqueous hydrochloric acid. The aqueous solution was extracted with chloroform. The chloroform solution was evaporated and the residue was crystallized from ethyl acetate (15.13 g, 92%), m.p. 155°–157° C.

B.
[(1,1-Dimethylethoxy)carbonyl]-N-[(1S)-1-(cyclohexylmethyl)-2-(dimethoxyphosphinyl)-2-hydroxyethyl]-3-[(phenylmethoxy)methyl]-L-histidinamide The title A compound (9.29 g, 23.06 mmol) was added to a solution of the title E compound of Example 1 (8.34 g, 27.6 mmol) in dimethylformamide 115 mL) and cooled to 0° C. Hydroxybenzotriazole hydrate (3.87 g, 25.4 mmol), triethylamine (4.82 mL, 34.6 mmol) and 1-(3-dimethylaminopropyl)-3-ethylcarbodiimide hydrochloride (4.86 g, 25.4 mmol) were added sequentially. After 16 hours at 25° C., a pH 4.01 buffer solution was added and the reaction mixture was stirred for an additional 10 minutes. The aqueous layer was extracted with ethyl acetate 2×500 mL) and the combined organic extracts were dried over sodium sulfate and concentrated. Purification of the crude product by flash chromatography yielded 9.37 g of the title B compound, which was characterized by MS and $^{13}$NMR.

C.
[(1,1-Dimethylelthoxy)carbonyl]-N-[(1S)-1-(cyclohexylmethyl)-2-(dimethoxyphosphinyl)-2-hydroxyethyl]-L-histidinamide, isomer A, monohydrochloride A mixture of the title B compound (1.24 g, 2 mmol), 20% palladium hydroxide on carbon (600 mg) and 1N hydrochloric acid (1.6 mL, 1.6 mmol) in methanol (10 ml) was stirred under hydrogen for 16 hours, after which it was filtered and concentrated. Repeated purifications of the crude (1.15 g) by flash chromatography yielded a residue which was dissolved in water containing 781 µl of 1N hydrochloric acid, millipore filtered and lyophilized to give the title compound (471.4 mg) as a pure white solid, m.p. 86°, $[\alpha]_D = -39.8°$ (c=0.65, CH$_3$OH).

Analysis calc'd for $C_{22}H_{39}N_4O_7P \cdot 1.25HCl$, $0.75H_2O$: C, 47.16; H, 7.51; N, 10.00; P, 5.53; Cl, 7.69; Found: C, 47.31; H, 7.15; N, 9.93; P, 5.58; Cl, 7.72.

EXAMPLE 10

(4-Morpholinylcarbonyl)-L-phenylalanyl-N-[(1S)-1-(cyclohexylmethyl)-2-[dimethoxyphosphinyl]-2-hydroxyethyl]-L-histidinamide, trifluoroacetate (1:1) salt

A.
N-(1S)-1-(Cyclohexylmethyl)-2-(dimethoxyphosphinyl)-2-hydroxyethyl]-3-[(phenylmethoxy)methyl]-L-histidinamide, monohydrochloride The title compound of Example 9 (7.14 g, 1.48 mmol) was dissolved in a solution of hydrochloric acid/ethyl acetate (1.4N, 55 mL), reacted for 1 hour and concentrated yielding 7.1 g of the title A compound as a white solid which was used directly for subsequent reactions, satisfactory MS and $^{13}$NMR data were obtained.

B.
(4-Morpholinylcarbonyl)-L-phenylalanyl-N-[(1S)-1-(cyclohexylmethyl)-2-[dimethoxyphosphinyl]-2-hydroxyethyl]-3-[(phenylmethoxy)methyl]-L-histidinamide The title A compound (3.4 g, 6 mmol) was added to a solution of the title C compound of Example 6 (1.45 g, 5 mmol) in dimethylformamide (25 mL) and cooled to 0° C. Hydroxybenzotriazole hydrate (840 mg, 5.5 mmol), triethylamine (1.04 mL, 7.5 mmol) and 1-(3-dimethylaminopropyl)-3-ethylcarbodiimide hydrochloride were added sequentially. After 16 hours at 25° C., a pH 4.01 buffer solution was added and the reaction mixture was stirred for 10 minutes. The aqueous layer was extracted with ethyl acetate (3×75 mL) and the combined extracts were dried and concentrated yielding 4.0 g of crude product. Chromatographic purification afforded 1.35 g of pure title B compound, which was characterized by MS and $^{13}$NMR.

Elemental analysis for $C_{39}H_{55}N_6O_9P \cdot 1.2H_2O$: C, 59.34 H, 7.34; N, 10.64; P, 3.92; Found: C, 59.34; H, 7.32; N, 10.44; P, 3.84.

C.
(4-Morpholinylcarbonyl)-L-phenylalanyl-N-[(1S)-1-(cyclohexylmethyl)-2-[dimethoxyphosphinyl]-2-hydroxyethyl]-L-histidinamide, trifluoroacetate (1:1) salt A mixture of the title B compound (1.22 g, 1.56 mmol), 20% palladium hydroxide on carbon (552 mg) and 1N hydrochloric acid (2.02 mL, 2.02 mmol) in methanol (18 mL) was stiarred under hydrogen for 16 hours, after which it was filtered over celite and concentrated. Purification of the crude (1.28 g) by flash chromatography yielded a residue which was dissolved in water containing 1.2 mL of 1N hydrochloric acid, millipore filtered and lyophilized to give the title compound (767.3 mg) as a white solid. This was subsequently repurified by preparative HPLC, eluting with 70% aqueous methanol containing 1% trifluoroacetic acid, to give 319 mg of the title compound, m.p. 85°–96° C., $[\alpha]_D = -15.6°$ (c=0.50, CH$_3$OH).

Elemental analysis calc'd for $C_{31}H_{47}N_6O_8P \cdot 1.00TFA$, $1.2H_2O$: C, 49,65; H, 6.36; N, 10.53; P, 3.88; F, 7.14; Found: C, 49,30; H, 6.00; N, 11.17; P, 3.69; F, 7.04.

EXAMPLE 11

[(Phenylmethoxy)carbonyl]-N-[(1S)-1-(cyclohexylmethyl)-2-(dimethoxyphosphinyl)-2-hydroxyethyl]-L-leucinamide, isomer A The title E compound of Example 1 (749.3 mg, 2.5 mmol) was added to a solution of N-α-CBZ-L-Leucine (548.5 mg, 2.07 mmol) in dimethylformamide (10 mL) and cooled to 0° C. Hydroxybenzotriazole hydrate (348.3 mg, 2.27 mmol), triethylamine (432.7 µl, 3.1 mmol) and 1-(3-dimethylaminopropyl)-3-ethylcarbodiimide hydrochloride (436.4 mg, 2.27 mmol) were added sequentially. After 16 hours at 25° C., pH 4.01 buffer solution was added and the reaction mixture was stirred for 10 minutes. The resulting precipitate was filtered, washed sequentially with pH 4.01 buffer (3×50 mL) and water (3×50 mL) and dried over sodium sulfate yielding 804 mg of crude material. Flash chromatographic purification afforded 546.4 mg of the title compound as a white solid, m.p. 151° C., $[\alpha]_D$ −56.2° (c=1.04, CH$_3$OH).

Elemental analysis calc'd for $C_{25}H_{41}N_2O_7P$: C, 58.58; H, 8.06; N, 5.47; P, 6.04; Found: C, 58.47; H, 7.88; N, 5.41; P, 5.89.

EXAMPLE 12

(1-Oxo-3-phenylpropyl)-N-[(1S,2R)-1-(cyclohexylmethyl)-2-(dimethoxyphosphinyl)-2-hydroxyethyl]-L-leucinamide The title A compound of Example 5 (622.2 mg, 1.5 mmol) was added to a solution of hydrocinnamic acid (225.3 mg, 1.5 mmol) in acetonitrile (7.5 mL) and cooled to 0° C. Hydroxybenzotriazole hydrate (229.5 mg, 1.5 mmol), N,N-diisopropylethylamine (287 μl, 1.65 mmol) and 1-(3-dimethylaminopropyl)-3-ethylcarbodiimide hydrochloride were added sequentially. After 64 hours at 0° C., additional N,N-diisopropylethylamine (52 μl, 0.3 mmol) was added and the reaction was allowed to proceed for 24 hours at 25° C. The reaction mixture was then concentrated and stirred with pH 4.01 buffer solution for 10 minutes. The resulting precipitate was filtered, washed sequentially with pH 4.01 buffer (3×50 mL) and water (3×50 mL), and dried in vacuo yielding 476.9 mg of crude product. Purification by flash chromatography afforded 253.6 mg of product, which was crystallized from hexane/ethyl acetate yielding 230.6 mg of the title compound, m.p. 157° C., $[\alpha]_D$= −74.6° (c=0.50, CH$_3$OH).

Elemental analysis for $C_{20}H_{43}N_2O_6P$: C, 61.06; H, 8.49; N, 5.48; P, 6.06; Found: C, 61.11; H, 8.63; N, 5.43; P, 5.40.

EXAMPLE 13

(1-Oxo-3-phenylpropyl)-N-[(1S,2R)-1-(cyclohexylmethyl)-2-(dimethoxyphosphinyl)-2-hydroxyethyl]-L-histidinamide, hydrochloride (2:3)

A.

(1-Oxo-3-phenylpropyl)-N-[(1S)-1-(cyclohexylmethyl)-2-(dimethoxyphosphinyl)-2-hydroxyethyl]-3-[(phenylmethoxy)methyl]-L-histidinamide The title A compound of Example 10 (1.67 g, 3 mmol) was added to a solution of hydrocinnamic acid (450.6 mg, 3 mmol) in dimethylformamide (15 mL) and cooled. Hydroxybenzotriazole hydrate (459 mg, 3 mmol), triethylamine (543.6 μl, 3.9 mmol) and 1-(3-dimethylaminopropyl)-3-ethylcarbodiimide hydrochloride were added sequentially. After 16 hours, additional triethylamine (83 μl, 0.6 mmol) was added and the reaction was allowed to.proceed for 20 hours at 25° C. The reaction mixture was then concentrated and stirred with pH 4.01 buffer solution for 10 minutes. The aqueous layer was extracted with ethyl acetate (2×75 mL) and the combined organics were washed with saturated aqueous sodium hydrogen carbonate (2×50 mL), dried over sodium sulfate and concentrated yielding 1.01 g of crude compound. Purification by flash chromatography afforded 645 mg of the pure title A compound, which was characterized by MS and $^{13}$NMR.

B.

(1-Oxo-3-phenylpropyl)-N-[(1S,2R)-1-(cyclohexylmethyl)-2-(dimethoxyphosphinyl)-2-hydroxyethyl]-L-histidinamide, hydrochloride (2:3)

A solution of the title A compound (645 mg, 0.98 mmol), palladium on carbon (300 mg) and 1N hydrochloric acid (1.1 mL, 1.1 mmol) in methanol (4 mL) was stirred under hydrogen for 16 hours, after which the reaction mixture was filtered and concentrated yielding 548 mg of crude product. Repeated purifications by flash chromatography afforded a residue which was dissolved in water containing 82 μl of 1N hydrochloric acid, millipore filtered and lyophilized to give 41.2 mg of the title compound as a fluffy white solid, m.p. 110°–125° C.

Elemental analysis calc'd for $C_{26}H_{39}N_4O_6P \cdot 1.5HCl \cdot 0.83H_2O$: C, 51.81; H, 7.05; N, 9.30; Cl, 5.14; P, 8.58 Found: C, 51.81; H, 7.09; N, 9.30; Cl, 5.33; P, 8.69.

EXAMPLE 14

(Cyclopentylcarbonyl)-L-phenylalanyl-N-[(1S)-1-(cyclophenylmethyl)-2-hydroxy-2-(hydroxymethoxyphosphinyl)ethyl]-L-leucinamide, isomer A, A solution of the title compound of Example 5 (125 mg, 0.2 mmol) in 25 ml acetone was saturated with trimethylamine and heated for 16 hours at 80° in a sealed tube. The solvents were removed on rotary evaporator and the residue was dissolved in ethyl acetate (30 ml), washed with 10% hydrochloric acid (2×15 ml), dried over sodium sulfate and concentrated to afford 102 mg crude product. Chromatographic purification yielded 65 mg of the title compound, m.p. 218°–227°.

Analysis calc'd for $C_{31}H_{50}N_3PO_7 \cdot 0.5CH_3CO_2H0.7-H_2O$: C, 59.14; H, 8.05; N, 6.47; Found: C, 59.10; H, 8.28; N, 6.46.

EXAMPLE 15

(Cyclopentylcarbonyl)-L-phenylalanyl-N-[(1S)-1-(cyclohexylmethyl)-2-(diethylphosphinyl)-2-hydroxyethyl]-L-leucinamide

A.

[(1S)-1-(Cyclohexylmethyl)-2-(diethylphosphinyl)-2-hydroxyethyl]carbamic acid, 1,1-dimethylethyl ester A tetrahydrofuran solution (8.3 ml) of diethyl phosphite (2.29 g, 16.6 mmol) was added dropwise over a period of 10 minutes to a flask containing 3M ethereal solution of ethyl magnesium bromide (16.6 ml 3M solution, 49.8 mmol) and tetrahydrofuran (8.3 ml) at 0°. The reaction mixture was warmed to room temperature and refluxed for 1 hour to ensure complete formation of the reagent, after which it was cooled to 0° and treated with a 10 ml tetrahydrofuran solution of the title C compound of Example 1 (2.2078 g, 8.3 mmol) The reaction mixture was refluxed for 30 minutes, cooled to 0° and quenched with 75 ml aqueous 10% hydrochloric acid. The aqueous solution was extracted with ethyl acetate (3×50 ml) and the combined organic extracts were dried over sodium sulfate and concentrated to yield 3.191 g residue. Flash chromatograhic purification afforded 2.452 g of the title A compound.

B.

(βS)-β-Amino-α-(diethylphosphinyl)cyclohexanepropanol, monohydrochloride

The title A compound (860 mg, 2.38 mmol) was treated with a solution of hydrochloric acid/ethyl acetate at 0° for 2 hours and at room temperature for 1.5 hours. Concentration afforded an oily residue which was redissolved in 1:1 hexane/ethyl acetate and concentrated again to afford the title B compound as a white solid (741 mg).

C. N-(L-Phenylalanyl)-L-leucine, methyl ester, monohydrochloride

The title C compound of Example 2 (12.01 g, 31 mmol) was dissolved in hydrochloric acid/acetic acid solution (62 mL), reacted for 1 hour and concentrated to give an oily residue. It was triturated with toluene (3×60 mL), and concentrated yielding 10 g of the title C compound.

D. N-[N-(Cyclopentylcarbonyl)-L-phenylalanyl]-L-leucine, methyl ester

Cyclopentane carboxylic acid (1.65 mL, 15.2 mmol) was added to a solution of the title C compound (5.0 g, 15.2 mmol) in dimethylformamide (60 mL) and cooled to 0° C. Hydroxybenzotriazole hydrate (2.33 g, 15.2 mmol), N,N-diisopropylethylamine (2.93 mL, 17 mmol) and dicyclohexylcarbodiimide (3.14 g, 15.2 mmol) were added sequentially. After 16 hours at 0° C., the reaction mixture was filtered and concentrated. The residue was taken in ethyl acetate (250 mL), washed with water (3×150 mL), saturated sodium bicarbonate (150 mL), saturated sodium chloride (150 mL), dried and concentrated, yielding 6.0 g of crude product. Purification by flash chromatography afforded 3.40 g of the title D compound, m.p. 170°–171° C., $[\alpha]_D = -23.9°$ (c 1.18, CH$_3$OH).

Elemental Analysis calc'd for $C_{22}H_{32}N_2O_4 \cdot 0.013 H_2O$: C, 67.60; H, 8.32; N, 7.17; Found: C, 67.57; H, 8.31; N, 7.20.

E. N-[N-(Cyclopentylcarbonyl]-L-phenylalanyl]-L-leucine

1N Sodium hydroxide (12.36 mL, 12 mmol) was added to a solution of the title D compound (2.04 g, 5.3 mmol) in methanol (20 mL). After 5 hours, the reaction mixture was concentrated and the residue was taken up in a mixture of water (20 mL) and ethyl acetate (50 mL) and acidified to pH 1.8. The layers were separated and aqueous layer was reextracted with ethyl acetate (3×75 mL). The combined organic extracts were dried and concentrated yielding 1.84 g of the title E compound, m.p. 148°–151° C., $[\alpha]_D = -12.9°$ (c=1.19, CH$_3$OH).

Elemental analysis calc'd for $C_{21}H_{30}N_2O_4 \cdot 1.34 H_2O$: C, 63.28; H, 8.26; N, 7.03; Found: C, 63.32; H, 7.77; N, 7.01.

F. (Cyclopentylcarbonyl)-L-phenylalanyl-N-[(1S)-1-(cyclohexylmethyl)-2-(diethylphosphinyl)-2-hydroxyethyl]-L-leucinamide Hydroxybenzotriazole hydrate (364.1 mg, 2.38 mmol), triethylamine (364.9 ml, 2.618 mmol) and 1-(3-dimethylaminopropyl)-3-ethylcarbodiimide hydrochloride (456 mg, 2.38 mmol) were sequentially added to a dimethylformamide solution (10 ml) of the title B compound and the title E compound at 0°. After stirring for 2 hours at 0°, the reaction mixture was left for overnight stirring at room tempertaure. The resulting solid mass was treated with 25 ml pH 4.00 buffer for 5 minutes and filtered. The precipitates were washed sequentially with buffer solution (2×10 ml), water (10×10 ml) and dried in vacuo (1.038 g). Flash chromatograhic purification afforded the title compound as 395 mg pure fast-moving isomer A, 197 mg diastereomeric mixture and 217 mg pure slow-moving isomer B.

The 395 mg fraction containing fast-moving isomer A was rechromatographed to remove minor amounts of the other diastereomer, m.p. 206°–209°, $[\alpha]_D = -29.8°$ (c=0.51, CH$_3$OH).

The 217 mg fraction containing slow-moving isomer B was also rechromatographed, m.p. 170°–175°, $[\alpha]_D = -32.0°$ (c=0.53, CH$_3$OH).

Elemental analysis calc'd for $C_{39}H_{56}N_3PO_5 \cdot 0.2H_2O$: C, 65.72; M, 9.15: N, 6.76: P. 4.98; Found: (A) C, 65.74; H, 8.81; N, 6.81; P, 4.97; (B) C, 65.68; H, 8.89; N, 6.68; P, 4.98.

EXAMPLE 16

(Cyclopentylcarbonyl)-L-phenylalanyl-N-[(1S)-1-(cyclohexylmethyl)-2-(ethylmethoxyphosphinyl)-2-hydroxyethyl]-L-leucinamide

A. Ethylphosphinic acid, methyl ester

A 60 ml ethereal solution of methanol (10.82 ml, 267 mmol) and triethylamine (16.92 ml, 121.4 mmol) was added dropwise to a solution of ethyl dichlorophosphine (15.9 g, 121.4 mmol) in 120 ml ether at 0°. After the addition was complete, the resulting slurry was refluxed for 1 hour, cooled to 0° and filtered. The precipitated solid was washed with an additional 100 ml ether. Most of the ethyl ether was removed on rotary evaporator and the residue vacuum distilled (18 mm Hg) to afford the title A compound (11.2 g), m.p. 105°–114°.

B. [(1S)-1-(Cyclohexylmethyl)-2-(ethylmethoxyphosphinyl)-2-[(trimethylsilyl)oxy]ethyl]-carbamic acid, 1,1-dimethylethyl ester The title A compound (1.05 ml, 10.4 mmol) was added to a solution of the title C compound of Example 1 (2.66 g, 10.4 mmol) in tetrahydrofuran (40 ml). Diisopropylethylamine (3.62 ml, 20.8 mmol) and trimethylsilylchloride (2.64 ml, 20.4 mmol) were added sequentially and the reaction left for overnight stirring at room temperature. After 17 hours, the reaction was quenched with water and tetrahydrofuran was removed on the rotary evaporator. The residue was dissolved in ethyl acetate (125 ml), washed sequentially with water (2×30 ml), saturated sodium chloride (30 ml), dried over sodium sulfate and concentrated to give 4.174 g crude product. Chromatographic purification yielded the title B compound as 678 mg pure fast moving diastereomer pair A, 719 mg mixture of A and B and 1.348 g pure slow moving diastereomer pair B.

C. [(2S)-2-Amino-3-cyclohexyl-1-hydroxypropyl]-ethylphosphinic acid, methyl ester, monohydrochloride The slow moving isomer pair B of part B of this Example (500 mg, 1.144 mmol) was treated with a solution of hydrochloric acid/ethyl acetate at room temperature for 2 hours. Concentration followed by trituration with ether afforded the title C compound as a white solid (296 mg).

D. (Cyclopentylcarbonyl)-L-phenylalanyl-N-[(1S)-1-(cyclohexylmethyl)-2-(ethylmethoxyphosphinyl)-2-hydroxyethyl]-L-leucinamide Hydroxybenzotriazole hydrate (153 mg, 1.0 mmol), triethylamine (167.3 μl, 1.2 mmol) and 1-(3-Dimethylaminopropyl)-3-ethylcarbodiimide hydrochloride (191.7 mg, 1.0 mmol) were sequentially added to a 6 ml dimethylformamide solution of the title C compound (296 mg, 0.988 mmol) and the title E compound of Example 15 (374.4 mg, 1.0 mmol). After 2 hours at 0° and 60 hours at room temperature, the reaction mixture was treated with 25 ml pH 4.01 buffer for 5 minutes and filtered. The solid was washed sequentially with the buffer solution (2×25 ml), water (5×20 ml) and then dried in vacuo to afford 495 mg crude product. Flash chromatographic purification afforded the title D compound as 90 mg fast moving isomer $B_1$, 186 mg diastereomeric mixture and 136 mg pure slow moving isomer $B_2$, m.p. 170°–174°.

Fast moving isomer $B_1$:

Analysis calc'd for $C_{33}H_{54}N_3O_6P \cdot 0.5H_2O$: C, 63.04; H, 8.82; N, 6.68; Found: C, 62.92; H, 8.41; N, 6.61.

Slow moving isomer $B_2$:

Analysis calc'd for $C_{33}H_{54}N_3O_6P \cdot 0.22H_2O$: C, 63.55; H, 8.80; N, 6.74; P, 4.97; Found: C, 63.54; H, 8.65; N, 6.59; P, 5.06.

E.
(Cyclopentylcarbonyl)-L-phenylalanyl-N-[(1S)-1-(cyclohexylmethyl)-2-(ethylmethoxyphosphinyl)-2-hydroxyethyl]-L-leucinamide In a similar manner, the fastmoving isomer pair A of part B of this Example was deprotected with hydrochloric acid/ethyl acetate and coupled with the title E compound of Example 15 to provide $A_1$ and $A_2$ mixture of diastereomers, m.p. 155°–165°.

Analysis calc'd for $C_{33}H_{54}N_3O_6P \cdot 0.5H_2O$: C, 63.04; H, 8.82; N, 6.68; Found: C, 63.09; H, 8.64; N, 6.56.

EXAMPLE 17

(1-Oxo-3-phenylpropyl)-N-[1-(cyclohexylmethyl)-2-(ethylmethoxyphosphinyl)-2-hydroxyethyl]-L-leucinamide, Isomer pair B

A.
(2S)-(2-Amino-3-cyclohexyl-1-hydroxypropyl)-ethylphosphinic acid, methyl ester, isomer pair B, monohydrochloride Compound B from Example 16 (529.5 mg, 1.2 mmol) was dissolved in a solution of HCl/EtOAc (25 mL). After 2.5 hours, the reaction mixture was concentrated yielding 358 mg of the title A compound which was characterized by $^{13}C$ NMR and $^{31}P$ NMR.

B. (S)-N-(1-Oxo-3-phenylpropyl)-L-leucine

L-Leucine (7.87 g, 60 mmol) was dissolved in a solution of sodium hydroxide (4.8 g, 120 mmol) in water (40 ml, 1.5M). Diethyl ether (40 ml) was added. The mixture was cooled in an ice bath and while stirring rapidly, hydrocinnamoyl chloride (10.1 g, 8.92 ml, 60 mmol) was added dropwise over a period of 30 minutes. The ice bath was removed and the mixture was stirred at room temperature 2 hours, maintaining a slightly basic pH by periodic addition of small amounts of 1N sodium hydroxide solution. The layers were separated. The ether layer was reextracted with 1N sodium hydroxide solution. The combined aqueous layers were washed once with ether and then acidified with concentrated hydrochloric acid. The product was extracted into chloroform, dried over magnesium sulfate, and freed of solvent in vacuo leaving a white solid (13.36 g). This material was recrystallized from ethyl acetate (65 ml) to give 8.37 g of the title B compound (53%), m.p. 129°–130° C. $[\alpha]_D = -41.3°$ (c=1.3, MeOH).

C.
(1-Oxo-3-phenylpropyl)-N-[1-(cyclohexylmethyl)-2-(ethylmethoxyphosphinyl)-2-hydroxyethyl]-L-leucinamide, Isomer pair B The title A compound (359 mg, 1.2 mmol) was added to a solution of the title B compound (379 mg, 1.44 mmol) in dimethylformamide (10 mL) and cooled to 0° C. 1-Hydroxybenzotriazole hydrate (257.0 mg, 1.68 mmol), N,N-diisopropylethylamine (271.6 μl, 1.56 mmol) and 1-(3-dimethylaminopropyl)-3-ethylcarbodiimide hydrochloride (321.9 mg, 1.68 mmol) were added sequentially. After 16 hours the reaction mixture was concentrated and stirred with pH 4.01 buffer solution (30 mL) for 10 minutes. The aqueous layer was extracted with ethyl acetate (3×30 mL) and the combined organics were dried concentrated yielding 400 mg of crude compound. Purification by flash chromatography (19:1 $CHCl_3/CH_3OH$, 50 g silica gel) afforded 320 mg 52.4%) of compound which was crystallized from ethyl acetate yielding 112.7 mg of pure title compound, m.p. 170°–175° C. $[\alpha]_D = -72.3°$ (c=0.77, $CH_3OH$).

EXAMPLE 18

(2S)-3-Cyclohexyl-1-hydroxy-2-[[N-(1-oxo-3-phenylpropyl)-L-leucyl]amino]propyl]methylphosphinic acid, methyl ester, isomer A

A.
(4S)-4-(Cyclohexylmethyl)-5-(dimethoxyphosphinyl)-2,2-dimethyl-3-oxazolidinecarboxylic acid, 1,1-dimethylethyl ester p-Toluenesulfonic acid (28.5 mg, 0.15 mmol) and 2,2-dimethoxypropane (3.075 ml, 25 mmol) were added to a solution of compound D from Example 1 (3.65 g, 10 mmol) in 30 ml benzene. The solution was refluxed for 30 minutes after which benzene was slowly distilled over a period of 1 hour by which time the volume in the reaction flask had reduced to 10 ml. Fresh portions of p-toluene solfonic acid (28.5 mg, 0.15 mmol), 2,2-dimethoxypropane (6.16 ml, 50 mmol) and benzene (25 ml) and the slow distillation was repeated. The addition and distillation sequence was repeated five more times after which the reaction was judged almost complete by TLC. The reaction mixture was concentrated and the residue (4.5 g) chromatographed (150 g silica gel, 1:1 hexane/ethyl acetate to 2:8:0.1 hexane/ethyl acetate/acetic acid) to yield 3.524 g (87%) pure title A compound and 0.314 g (8.6%) of unreacted starting material, $[\alpha]_D = -5.8°$ (c=0.89 $CH_3OH$) which was characterized by MS, $^1H$ NMR, $^{13}C$ NMR and $^{31}P$ NMR [23.3 and 20.2 ppm 9:1) w.r.t. $H_3PO_4=0$, external standard 36.5 MHz].

The above reaction, when repeated on a 100 mmol scale, qave 28.944 g (82.3%) of the title A compound.

B.
(4S)-4-(Cyclohexylmethyl)-5-(hydroxymethoxyphosphinyl)-2,2-dimethyl-3-oxazolidinecarboxylic acid, 1,1-dimethylethyl este Sodium iodide (9 g, 60 mmol) was added to a solution of the title A compound (4.05 g, 10 mmol) in 50 ml acetone and refluxed for 3.5 hours. The reaction mixture was concentrated, the residue dissolved in ethyl acetate (50 ml) and washed sequentially with 1N HCl (1×50 ml), 10% sodium thiosulfate (1×75 ml) dried and concentrated to give 4.23 g crude product. Chromatograhic purification (silica gel, 9:1:0.1

CHCl₃/MeOH/AcOH) yielded 3.85 g (98.4%) pure title B compound, which was characterized by MS, $^1$H NMR and $^{13}$C NMR.

C.
(4S)-4-(Cyclohexylmethyl)-5-(methoxymethylphosphinyl)-2,2-dimethyl-3-oxazolidinecarboxylic acid, 1,1-dimethylethyl ester Sodium methoxide (65 mg, 1.2 mmol) was added to a solution of the title B compound (391 mg, 1.0 mmol) in 3 ml methanol. After 4 hours at room temperature, the solution was concentrated, triturated with toluene and concentrated in vacuo. The resulting sodium salt was dissolved in 4 ml dichloromethane and treated with oxalyl chloride (131 μl, 1.5 mmol) and dimethylformamide (2 drops, catalytic amount) at 0°. The reaction mixture was warmed to room temperature and after 2 hours, the solvents were removed under vacuo and the crude chloride was dissolved in 4 ml tetrahydrofuran, cooled to −78° and treated with methyl magnesium bromide (3M, 300 μl, 0.9 mmol). The reaction was left for overnight stirring with gradual warming to room temperature. Next day, it was quenched with saturated NH₄Cl, extracted with ethyl acetate (3×20 ml) and the combined organic extracts were dried and concentrated. Chromatographic purification (25 g silica gel, 1:1 hexane/ethyl acetate) of the residue gave 133 mg (38%) of pure title C compound which was characterized by MS, $^1$H NMR and $^{13}$C NMR. The yield was reproducible when the reaction was repeated on a 5 mmol scale. After repeated chromatographic purifications, 726 mg of the title C compound gave 310 mg of the fast moving isomer A and 218 mg of the slow moving diastereomer B.

D.
(2S)-(2-Amino-3-cyclohexyl-1-hydroxypropyl)-methylphosphinic acid, methyl ester, isomer A, monohydrochloride The fast moving diastereomer A of the title C compound (155 mg, 0.4 mmol) was treated with anhydrous hydrochloric acid in dioxane (4.5N) and the progress of reaction monitored by TLC. After 1.5 hours at room temperature, the reaction mixture was concentrated, under vacuo and the crude product directly utilized for the next reaction.

E.
(2S)-[3-Cyclohexyl-1-hydroxy-2-[[N-(1-oxo-3-phenylpropyl)-L-leucyl]amino]propyl]methylphosphinic acid, methyl ester, isomer A Hydroxybenzotriazole 85.7 mg, 0.56 mmol), diisopropylethylamine (90.6 μl, 0.52 mmol) and 1-(3-dimethylaminopropyl)-3-ethyl carbodiimide hydrochloride (107.3 mg, 0.56 mmol) were sequentially added to a solution of the title D compound (114.2 mg, 0.4 mmol) and compound B from Example 17 (126.2 mg, 0.48 mmol) in 2 ml dimethylformamide at 0°. The reaction mixture was warmed and stirred at room temperature for 60 hours after which it was concentrated, then treated with 15 ml pH=4.01 buffer and extracted with ethyl acetate (3×25 ml). Drying and concentration gave 425 mg crude product which after flash chromatographic purification (20 g silica gel, 19:1 CHCl₃/MeOH) gave 146 mg (74%) of the title compound Isomer A which was characterized by MS, IR, $^1$H NMR and $^{13}$C NMR. After repeated chromatography and finally, crystallization from hexane/ethyl acetate, the title compound Isomer A (56 mg) was obtained, m.p. 165°–170° C. [α]_D= −67.1° (c=0.66, CH₃OH).

Elemental analysis for C₂₆H₄₃N₂O₅P.0.4H₂O: Calc'd: C, 62.23; H, 8.80; N, 5.58; P, 6.17; Found: C, 62.24; H, 8.80; N, 5.83; P, 6.46.

EXAMPLE 19
(2S)-[3-Cyclohexyl-1-hydroxy-2-[[N-(1-oxo-3-phenylpropyl)-L-leucyl]amino]propyl]methylphosphinic acid, methyl ester, isomer B

A.
(2S)-(2-Amino-3-cyclohexyl-1-hydroxypropyl)methylphosphinic acid, methyl ester, isomer B, monohydrochloride The slow moving diastereomer B of compound C from Example 18 (218 mg, 0.56 mmol) was treated with anhydrous HCl in dioxane (4.5N) for 4 hours at 0° after which the reaction mixture was concentrated under vacuo and the crude product directly utilized for the next reaction.

B.
(2S)-[3-Cyclohexyl-1-hydroxy-2-[[N-(1-oxo-3-phenylpropyl)-L-leucyl]amino]propyl]methylphosphinic acid, methyl ester, isomer B Hydroxybenzotriazole (120 mg, 0.784 mmol), diisopropylethylamine (127 μl, 0.728 mmol) and 1-(3-dimethylaminopropyl)-3-ethyl carbodiimide hydrochloride (150 mg, 0.784 mmol) were sequentially added to a solution of the title A compound obtained from the previous reaction and the title B compound from Example 17 (176.7 mg, 0.672 mmol) in 3 ml dimethylformamide at 0°. The reaction mixture was warmed and stirred at room temperature for 72 hours after which it was concentrated, then treated with 20 ml pH=4.01 buffer and extracted with ethyl acetate (3×30 ml). Drying and concentration followed by chromatographic purification of the crude product gave 146 mg 52.7%) pure title compound Isomer B, m.p. 188°–207°, [α]_D= −71.7° (c=0.545, CH₃OH) which was characterized by MS, IR, $^1$H NMR, $^{13}$C NMR and $^{31}$P NMR [56.0 ppm w.r.t H₃PO₄ as external reference, CDCl₃, 36.4 MHz].

Elemental analysis for C₂₆H₄₃N₂O₅P.0.28H₂O: Calc'd: C, 62.51; H, 8.79; N, 5.61; P, 6.20; Found: C, 62.61; H, 8.76; N, 5.51; P, 6.20.

EXAMPLE 20
(2S)-[3-Cyclohexyl-1-hydroxy-2-[[N-(1-oxo-3-phenylpropyl)-L-leucyl]amino]propyl]-N-methyl phosphonamidic acid, methyl ester (3:2)

A.
(4S)-4-(Cyclohexylmethyl)-5-[methoxy(methylamino)-phosphinyl]-2,2-dimethyl-3-oxazolidinecarboxylic acid, 1,1-dimethylethyl ester, 3:2 mixture of isomers Sodium methoxide (120 mg, 2.2 mmol) was added to a solution of compound B from Example 18 (782 mg, 2.0 mmol) in 4 ml methanol. After 4 hours at room temperature, freshly distilled toluene (10 ml) was added and the solution concentrated and left overnight under vacuo. Next day, the sodium salt was dissolved in 6 ml dichloromethane, treated with oxalyl chloride (524 μl, 6 mmol) and dimethylformamide (2 drops, catalytic amount). After refluxing for 30 minutes, solvents were removed and the crude chloridate left under vacuo for 3 hours. The chloridate was then redissolved in a 4 ml dichloromethane and treated with 2 ml 4.5M methylamine (9 mmol) in dichloromethane. After 2 hours at room temperature, the reaction mixture was quenched with water (15 ml) and extracted with dichloromethane (2×20 ml). The combined organic extracts were washed with 5% HCl (1×15 ml), dried (NO$_2$SO$_4$) and concentrated to give the crude product which, after chromatographic purification afforded 385 mg (48%) of the title A compound as a 1.5:1.0 mixture of diastereomers. It was characterized by MS, $^1$H NMR, $^{13}$C NMR and $^{31}$P NMR [28.6 and 27.4 ppm (1:1.5) w.r.t. H$_3$PO$_4$ as external reference, CDCl$_3$, 36.4 MHz].

B.
(2S)-(2-Amino-3-cyclohexyl-1-hydroxypropyl)-N-methylphosphonamidic acid, methyl ester The title A compound (405 mg, 1.05 mmol) was dissolved in 10 ml dichloromethane and heated with 0.1M trimethylsilyl trifluoromethane sulfonate (203 μl, 1.05 mmol) in dichloromethane. After 5 hours at room temperature, additional reagent (40 μl, 0.2 mmol) was added and the reaction was stirred for an additional 2 hours. Concentration and trituration with ethyl acetate followed by drying under vacuo gave the crude title B compound which was directly utilized for the next reaction.

C.
(2S)-[3-Cyclohexyl-1-hydroxy-2-[[N-(1-oxo-3-phenylpropyl)-L-leucyl]amino]propyl]-N-methyl phosphonamidic acid, methyl ester (3:2)

1-Hydroxybenzotriazole hydrate (225 mg, 1.47 mmol), N,N-diisopropylethylamine (237.8 μl, 1.365 mmol) and 1-(3-dimethylaminopropyl)-3-ethyl carbodiimide hydrochloride (281.8 mg, 1.47 mmol) were sequentially added to a solution of the title B compound obtained from the previous reaction and the title B compound from Example 17 (276 mg, 1.26 mmol) in 5 ml dimethylformamide of 0°. The reaction mixture was warmed and stirred at room temperature for 24 hours after which it was concentrated, then treated with 30 ml pH=4.01 buffer and extracted with ethyl acetate (3×25 ml). The combined organic extracts were washed sequentially with saturated NaHCO$_3$ (2×20 ml). Saturated NaCl (1×15 ml), dried and concentrated to give 398 mg crude product. Chromatographic purification (40 g silica gel, 1:1 hexane/ethyl acetate followed by 30:1 CHCl$_3$/MeOH) yielded 320 mg (60%) pure title compound. It was crystallized from ethyl acetate, m.p.=175°-177° C., [α]$_D$=−74° (c=0.64, CH$_3$OH) and characterized by MS, IR, $^1$H NMR, $^{13}$C NMR and $^{31}$P NMR [30.8 and 30.65 ppm (1.5:1.0) w.r.t. H$_3$PO$_4$ as external reference, CDCl$_3$, 36.5 MHz].

Elemental analysis for C$_{26}$H$_{44}$N$_3$O$_5$P: Calc'd: C, 61,27; , 8.70; N, 8.25; P, 6.08; Found: C, 61.53; H, 8.59; N, 8.30; P, 6.51.

EXAMPLE 21
(1S)-(1-Oxo-3-phenylpropyl)-N-[1-(cyclohexylmethyl)-2-hydroxy-2-[methoxy(1-methylethoxy)phosphinyl]ethyl]-L-leucinamide

A.
(4S)-4-(Cyclohexylmethyl)-5-[methoxy(1-methylethoxy)phosphinyl]-2,2-dimethyl-3-oxazolidinecarboxylic acid, 1,1-dimethylethyl ester A solution of the title B compound from Examle 18 (1.56 g, 4 mmol), 2-bromopropane (4.84 ml, 52 mmol) and potassium carbonate (2.76 g, 20 mmol) in 16 ml dimethylformamide was stirred for 15 hours at 45°. 2-Bromopropane (0.187 ml, 2 mmol) was added and stirring at 45° continued for 48 hours. After treating with an additional 0.56 ml (6 mmol) of 2-bromopropane and stirring at 45° for 15 hours, the reaction mixture was concentrated in vacuo. The residue was taken in ethyl acetate (100 ml) and washed with 5% HCl (2×30 ml). Drying and concentration gave 1.5 g crude product. Chromatographic purification yielded 1.12 g (65.8%) pure title A compound, which was characterized by MS, $^1$H NMR, $^{13}$C NMR and $^{31}$P NMR.

B.
(2S)-(2-Amino-3-cyclohexyl-1-hydroxypropyl)phosphonic acid, methyl 1-methylethyl ester, monohydrochloride The title A compound (433.4 mg, 1 mmol) was refluxed for 2 hours in a 6 ml solution of 3:2:1 tetrahydrofuran/aqueous 10% HCl/acetic acid. Concentration under vacuo yielded 343.3 mg crude title B compound which was directly utilized for the next reaction.

C.
(1S)-(1-Oxo-3-phenylpropyl)-N-[1-(cyclohexylmethyl)-2-hydroxy-2-[methoxy(1-methylethoxy)phosphinyl]ethyl]-L-leucinamide The title B compound from Example 17 (316.4 mg, 1.2 mmol) was added to a cooled solution of the title B compound (313.7 mg, 1 mmol) in dimethylformamide (4 mL). 1-Hydroxybenzotriazole hydrate (214 mg, 1.4 mmol), N,N-diisopropylethylamine (226.4 μl, 1.3 mmol) and 1-(3-dimethylaminopropyl)-3-ethylcarbodiimide (268.3 mg, 1.4 mmol) were added sequentially. After 16 hours at 25° C., the reaction mixture was concentrated and stirred with a pH 4.01 buffer solution (30 mL) for 10 minutes. The aqueous portion was extracted with ethyl acetate (2×20 mL), and the combined organic extracts were washed sequentially with saturated aqueous sodium hydrogen carbonate (20 mL), saturated aqueous sodium chloride (20 mL , dried and concentrated yielding 830 mg of crude compound. Purification by flash chromatography (19:1:0.05 CHCl$_3$/CH$_3$OH/NH$_4$OH, 66 g silica gel) afforded 386.5 mg (72%) of pure title compound, m.p. 148°-155° C., [α]$_D$=−57.7° (c=0.54, CH$_3$OH)) which was characterized by MS, $^1$H NMR, $^{13}$C NMR and $^{31}$P NMR [22.9 and 22.8 ppm (1:1) w.r.t. H$_3$PO$_4$=0 ppm as external reference].

Elemental analysis for C$_{28}$H$_{47}$N$_2$O$_6$P.0.2H$_2$O: Calc'd: C, 62.31; H, 8.80; N, 5.19; P, 5.74; Found: C, 62.26; H, 8.87; N, 5.24; P, 5.94.

EXAMPLE 22
(1S)-(1-Oxo-3-phenylpropyl)-N-[1-(cyclohexylmethyl)-2-hydroxy-2-[methoxy(2-methylpropoxy)phosphinyl]ethyl]-L-leucinamide

A.
(4S)-4-(Cyclohexylmethyl)-5-methoxy(2-methylpropoxy)phosphinyl]-2,2-dimethyl-3-oxazolidinecarboxylic acid, 1,1-dimethylethyl ester 1-Bromo-2-methylpropane (6.23 mL, 57.5 mmol) was added to a solution containing the title B compound from Example 18 (977.5 mg, 2.5 mmol) and K$_2$CO$_3$ (1.73 g, 12.5 mmol) in dimethylformamide (10 mL). After 64 hours at 45° C. the reaction mixture was concentrated and the residue was dissolved in ethyl acetate (90 mL)

and washed with 5% aqueous HCl (50 mL). The aqueous layer was reextracted with ethyl acetate (60 mL) and the combined organic portions were dried (Na$_2$SO$_4$) and concentrated yielding 1.1 g of crude compound. Purification by flash chromatography (1:1 Hexane/ethyl acetate, 60 g of silica gel) afforded 565 mg (52%) of pure title A compound. Mass spectrum, $^{13}$C NMR, $^{1}$H NMR and $^{31}$P NMR characterizations were consistent with the desired product.

B.
(2S)-(2-Amino-3-cyclohexyl-1-hydroxypropyl)phosphonic acid, methyl 2-methylpropyl ester, monohydrochloride The title A compound (267.5 mg, 0.59 mmol) was dissolved and stirred in a solution of THF/10% HCl/AcOH, 3:2:1 (6 mL) at 45° C. After 4 hours the reaction mixture was concentrated and dried (Na$_2$SO$_4$). Purification by flash chromatography (90/10/0.1 CHCl$_3$:MeOH:AcOH, 20 g silica gel) afforded 181.5 mg (89.5%) of pure title B compound. Mass spectrum, $^{13}$C NMR, $^{1}$H NMR and $^{31}$P NMR characterizations were consistent with the desired product.

C. (1S)-(1-Oxo-3-phenylpropyl)-N-[1-(cyclo hexylmethyl)-2-hydroxy-2-[methoxy(2-methylpropoxy)phosphinyl]ethyl]-L-leucinamide A solution of the title B compound (185.5 mg, 0.54 mmol) and N,N-diisopropylethylamine (122.3 μl, 0.702 mmol) in dimethylformamide (2 mL) was added to a cooled solution of the title B compound from Example 17 (170.6 mg, 0.65 mmol), 1-hydroxybenzotriazole hydrate (115.6 mg, 0.76 mmol) and 1-(3-dimethylaminopropyl)-3-ethylcarbodiimide (144.5 mg, 0.76 mmol) in dimethylformamide (2 mL). After 16 hours at 25° C. the reaction mixture was concentrated and stirred with a pH 4.01 buffer solution (20 mL) for 10 minutes. The aqueous portion was extracted using ethyl acetate (3×20 mL) and the combined organic layers were washed with saturated aqueous sodium hydrogen carbonate (20 mL), saturated aqueous sodium chloride (20 mL) dried over sodium sulfate and concentrated yielding 207 mg of crude product. Purification by flash chromatography (27 g silica gel, 2:8:0.1 HCl/EtOAc/AcOH, then 11 g silica gel, 19:1:0.05 CHCl$_3$/CH$_3$OH/NH$_4$OH) yielded 84 mg (28.2%) of the title compound, m.p. 150° C., $[\alpha]_D = -58.7°$ (c=0.46, CH$_3$OH, MS, $^1$H NMR, $^{13}$C NMR and $^{31}$P NMR. Characterizations were consistent with the desired product.

Elemental analysis for C$_{29}$H$_{49}$N$_2$O$_6$P.0.25H$_2$O: Calc'd: C, 62.52; H, 8 95; N, 5.03; P, 5.56; Found: C, 62.65; H, 8.84; N, 5.18; P, 5.78.

EXAMPLE 23

(1S)-[(1,1-Dimethylethoxy)carbonyl]-N-[1-(cyclohexylmethyl)-2-(diethoxyphosphinyl)-2-hydroxyethyl]-L-histidinamide, monohydrochloride A.
(1S)-[(1,1-Dimethylethoxy)carbonyl]-N-[1-(cyclohexylmethyl)-2-(diethoxyphosphinyl)-2-hydroxyethyl]-3-[(phenylmethoxy)methyl]-L-histidinamide Compound B from Example 2 (1.47 g, 4.46 mmol) was added to a solution of [(1,1-dimethylethoxy)carbonyl]-3-[(phenylmethoxy)methyl]-L-histidine (T. Brown and J. H. Jones, Journal of Chemical Society, Chemical Communications (1981), 648) in tetrahydrofuran (22 mL) and cooled to 0° C. 1-Hydroxybenzotriazole hydrate (682 mg, 4.46 mmol), N,N-diisopropylethylamine (854.5 μl, 4.9 mmol) and dicyclohexylcarbodiimide (920 mg, 4.46 mmol) were added sequentially. After 16 hours at 25° C., the reaction mixture was filtered and concentrated. The residue was dissolved in ethyl acetate (60 mL), washed sequentially with saturated aqueous sodium hydrogen carbonate (2×40 mL), saturated aqueous sodium chloride (40 mL), dried (Na$_2$HSO$_4$) and concentrated. Repeated purifications by column chromatography of the crude product (2.9 g) yielded 2.03 g (70.2%) of pure title A compound.

Elemental analysis for C$_{32}$H$_{51}$N$_4$O$_8$P.0.73H$_2$O: Calc'd: C, 57.90 H, 7.96; N, 8.44; P, 4.67; Found: C, 57.95; H, 7.73; N, 8.39; P, 5.01.

B.
(1S)-[(1,1-Dimethylethoxy)carbonyl]-N-[1-(cyclohexylmethyl)-2-(diethoxyphosphinyl)-2-hydroxyethyl]-L-histidinamide, monohydrochloride A solution of the title A compound (780.7 mg, 1.2 mmol), palladium hydroxide on carbon (360 mg) and 1.0N hydrochloric acid (960 μl, 0.96 mmol) in methanol (10 mL) was stirred under hydrogen for 16 hours, after which the reaction mixture was filtered and concentrated yielding 564.6 mg of crude product. Repeated purifications by column chromatography yielded 456 mg (66%) of isomerically impure product of which 170 mg (25%) of the pure major isomer was isolated, dissolved in water containing 219 μl of 1N HCl, millipore filtered and lyophilized to give the title compound as a pure white solid, m.p. 110°-119° C. decomposition, $[\alpha]_D = -30.6°$ (c=0.5, CH$_3$OH).

Elemental analysis for C$_{24}$H$_{43}$N$_4$O$_7$P.1.0HCl, 1.5H$_2$O: Calc'd: C, 48.54; H, 7.97; N, 9.44; P, 5.22; Cl, 5.97; Found: C, 48.23; H, 7.47; N, 9.47; P, 5.13; Cl, 5.68.

EXAMPLE 24

(3,3-Dimethyl-1-oxobutyl)-N-[(1S)-1-(cyclohexylmethyl)-2-(dimethoxyphosphinyl)-2-hydroxyethyl]-L-histidinamide, monohydrochloride A.
(1S)-[(1,1-Dimethylethoxy)carbonyl]-N-[1-(cyclohexylmethyl)-2-(dimethoxyphosphinyl)-2-hydroxyethyl]-3-(3,5-dinitrophenyl)-L-histidinamide The title D compound from Example 1 (995.6 mg, 3.3 mmol) was added to a solution of t-Boc-im-DNP-L-Histidine (1.45 g, 3.3 mmol) and cooled to 0° C. 1-Hydroxybenzotriazole hydrate (504.9 mg, 3.3 mmol), N,N-diisopropylethylamine (632.3 μl, 3.63 mmol) and dicyclohexylcarbodiimide (679.8 mg, 3.3 mmol) were added sequentially. After 16 hours at 25° C., the reaction mixture was concentrated and the residue was dissolved in CH$_2$Cl$_2$ (75 ml), washed sequentially with water (2×50 mL), 1:1 water/saturated aqueous sodium hydrogen carbonate (50 mL), dried (Na$_2$SO$_4$) and concentrated. Purification of the crude product (2.02 g) by flash chromatography (120 g of Merck silica gel, 1:1 Hexane/ethyl acetate, 19:1:0.05 CHCl$_3$CH$_3$OH/NH$_4$OH) yielded 1.23 g 54.5%) of pure title A compound. Satisfactory $^{13}$C NMR and $^{31}$P NMR were obtained.

B.
(1S)-N-[1-(Cyclohexylmethyl)-2-dimethoxyphosphinyl)-2-hydroxyethyl]-3-(3,5-dinitrophenyl)-L-histidinamide, monohydrochloride The title A compound (1.08 mg, 1.61 mmol) was dissolved in a solution of hydrochloric acid/ethyl acetate (1.4N, 8 mL) and stirred at room temperature for 1 hour before concentrating and drying in vacuo overnight. A quantitative amount of the title B compound (1.01 g) was obtained and characterized by mass spectrum, $^{13}$C NMR and $^{31}$P NMR. The crude product was directly used for the next reaction.

C.
(1S)-(3,3-Dimethyl-1-oxobutyl)-N-[1-(cyclohexylmethyl)-2-(dimethoxyphosphinyl)-2-hydroxyethyl]-3-(3,5-dinitrophenyl)-L-histidinamide The title B compound (967.8 mg, 1.6 mmol) was added to a solution of tert-butylacetic acid (264.2 μl, 3.7 mmol) in dimethylformamide (8 mL) and cooled to 0° C. 1-Hydroxybenzotriazole hydrate (367.2 mg, 2.4 mmol), N,N-diisopropylethylamine (362.3 μl, 2.08 mmol) and 1-(3-dimethylaminopropyl)-3-ethylcarbodiimide hydrochloride (460.1 mg, 2.4 mmol) were added sequentially. After 40 hours at 25° C., the reaction mixture was concentrated and the residue was stirred for 10 minutes in pH 4.01 buffer solution (25 mL). The aqueous layer was extracted with ethyl acetate (3×80 mL) and the combined organics were washed with saturated aqueous sodium hydrogen carbonate (60 mL), dried and concentrated. Purification of the crude (1.25 g) product (150 g Merck silica gel, 19:1 CHCl$_3$/CH$_3$OH) yielded 586 mg (55.2%) of pure title C compound. Mass spectrum, $^{13}$C NMR and $^{31}$P NMR characterizations were consistent with the desired compound.

D.
(3,3-Dimethyl-1-oxobutyl)-N-[(1S)-1-(cyclohexylmethyl)-2-(dimethoxyphosphinyl)-2-hydroxyethyl]-L-histidinamide, monohydrochloride Mercaptoacetic acid (166.8 μl, 2.4 mmol) was added to a solution of the title C compound (310 mg. 0.48 mmol) in dimethylformamide (2.5 mL) and cooled to 0° C. After 4 hours, the reaction mixture was concentrated and the residue was dissolved in ethyl acetate (20 mL), washed with 1:1 water saturated aqueous sodium hydrogen carbonate (10 mL), dried (Na$_2$SO$_4$) and concentrated yielding 267 mg of crude product. Purification by flash chromatography (32 g Merck silica gel, 90:10:1:0.1 CHCl$_3$/CH$_3$OH/H$_2$O/AcOH, 42 g Merck silica gel, 9:1 CHCl$_3$/CH$_3$OH) afforded 140 mg (52.2%) of pure product which was dissolved in water containing 250 μl of 1N hydrochloric acid, millipore filtered and lyophilized to give the title compound as a white solid. m.p. 108°–135° C. (slow decomposition), $[\alpha]_D = -45.5°$ (c=0.55, CH$_3$OH).

Analysis calc'd for C$_{23}$H$_{41}$N$_4$O$_6$P.1.15HCl, 0.45 H$_2$O: C, 50.16; H, 7.88; N, 10.18; P, 5.62; Cl, 7.40;
Found: C, 50.03; H, 8.13; N, 10.31; P, 5.52; Cl, 7.49.

EXAMPLE 25
[(1-Methylethoxy)carbonyl]-N-[(1S)-1-(cyclohexylmethyl)-2-(dimethoxyphosphinyl)-2-hydroxyethyl]-L-histidinamide, sesquihydrochloride

A.
(1S)-[(I-Methylethoxy)carbonyl]-N-[1-(cyclohexylmethyl)-2-(dimethoxyphosphinyl)-2-hydroxyethyl]-3-(3,5-dinitrophenyl)-L-histidinamide Isopropyl chloroformate (121.5 μl, 1.06 mmol) and N,N-diisopropylethylamine (573.6 μl, 3.2 mmol) were sequentially added to a solution of the title B compound from Example 24 (538.2 mg, 0.89 mmol) in dimethylformamide (5 ml). After 96 hours, the reaction mixture was concentrated and the residue was dissolved in ethyl acetate (40 mL), washed with saturated aqueous sodium hydrogen carbonate (25 mL, dried (Na$_2$SO$_4$), and concentrated yielding 510 mg of crude product. Purification by flash chromatography (19:1 CHCl$_3$/CH$_3$OH, 51 g silica gel) afforded 370.8 mg (63.7% yield) of the title A compound.

B.
[(1-Methylethoxy)carbonyl]-N-(1S)-1-(cyclohexylmethyl)-2-(dimethoxyphosphinyl)-2-hydroxyethyl]-L-histidinamide, sesquihydrochloride Mercaptoacetic acid (48.5 μl, 0.7 mmol) was added to an ice cooled solution of the title A compound (89 mg, 0.14 mmol) in dimethylformamide (700 μl). After 4 hours at 0° C. the reaction mixture was concentrated yielding 212 mg of crude product. Purification by flash chromatography (50 g of silica gel, 9:1 CHCl$_3$/CH$_3$OH) yielded 65 mg (52%) of pure product which was dissolved in water containing 111 μl of 1N HCl, millipore filtered, and lyophilized to give 45.4 mg of the title compound, m.p. 81°–105° C. (decomposition), $[\alpha]_D = -35.1°$ (0.31, CH$_3$OH). Satisfactory MS, $^1$H NMR, $^{13}$C NMR and $^{31}$P NMR (28.9 ppm w.r t. H$_3$PO$_4$=0 ppm as external reference were obtained.

Elemental analysis for C$_{21}$H$_{37}$N$_4$O$_7$P.1.5HCl: Calc'd: C, 46.43; H, 7.14; N, 10.32; P, 5.70; Cl, 9.79; Found: C, 46.84; H, 7.14; N, 10.26; P. 5.97; Cl, 9.58.

EXAMPLES 26 to 69

Following the procedure of Examples 1 to 25 outlined above, the following additional compounds of formoula I within the scope of the present invention can be prepared.

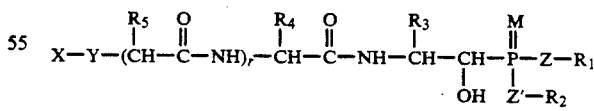

| Ex. No. | X | Y | r | R₅ | R₄ | R₃ | $M=\overset{\|}{P}-Z-R_1$ $Z'-R_2$ |
|---|---|---|---|---|---|---|---|
| 26 | H₂N—(CH₂)₅—C(=O)— | —NH— | 1 | benzyl (—CH₂—C₆H₅) | (CH₃)₂CH—CH₂— | cyclohexylmethyl | $\overset{O}{\|}$ —P(OCH₂CH₃)₂ |
| 27 | H₂N—(CH₂)₅—C(=O)— | " | " | 4-methoxybenzyl (H₃CO—C₆H₄—CH₂—) | " | " | $\overset{O}{\|}$ —P(OCH₃)₂ |
| 28 | H₂N—(CH₂)₅—C(=O)— | " | " | benzyl | imidazol-4-ylmethyl | " | $\overset{O}{\|}$ —P(OCH₃)₂ |
| 29 | " | " | " | 1-naphthylmethyl | (CH₃)₂CH—CH₂— | " | " |
| 30 | HO₂C—(CH₂)₅—C(=O)— | —NH— | 1 | benzyl | (CH₃)₂CH—CH₂— | cyclohexylmethyl | $\overset{O}{\|}$ —P(OCH₃)₂ |
| 31 | (CH₃)₃CO—C(=O)—NH—C(=O)—⌐ └—(CH₂)₅—C(=O)— | " | " | " | " | " | " |

-continued

| Ex. No. | X | Y | R₅ | R₄ | R₃ | $\overset{M}{\underset{\|}{=}}P-Z-R_1$ / $Z'-R_2$ |
|---|---|---|---|---|---|---|
| 32 | H₃C—C(CH₃)(NH₂)—CH₂—C(=O)— | " | " | " | " | " |
| 33 | H₂N—C(=NH)—HN—(CH₂)₅—C(=O)— | " | " | " | " | " |
| 34 | H₂N—C(=O)—HN—(CH₂)₅—C(=O)— | —NH— | —CH₂—C₆H₅ | (CH₃)₂CH—CH₂— | —CH₂—cyclohexyl | —P(=O)(OCH₃)₂ |
| 35 | pyrrolidin-1-yl—C(=O)— | " | " | " | " | " |
| 36 | morpholin-4-yl—C(=O)— | " | —CH₂—C₆H₄—OCH₃ (p) | " | " | " |
| 37 | 4-methylpiperazin-1-yl—C(=O)— | " | —CH₂—C₆H₅ | CH₃CH₂CH₂CH₂— | " | " |
| 38 | (CH₃)₃C—O—C(=O)— | —NH— | —CH₂—(1-naphthyl) | (CH₃)₂CH—CH₂— | —CH₂—cyclohexyl | —P(=O)(OCH₃)₂ |

-continued

| Ex. No. | X | Y | r | R$_5$ | R$_4$ | R$_3$ | M=P-Z-R$_1$ / Z'-R$_2$ |
|---|---|---|---|---|---|---|---|
| 39 | cyclopentyl-C(=O)- | " | " | benzyl | CH$_3$-N(CH$_2$-)-CH=N- (imidazole-CH$_2$-) | " | " |
| 40 | H- | " | " | " | (CH$_3$)$_2$CH-CH$_2$- | " | " |
| 41 | H$_2$N-(CH$_2$)$_5$-C(=O)- | " | " | " | S-CH=N- (thiazole-CH$_2$-) | " | " |
| 42 | (CH$_3$)$_2$CH-O-C(=O)- | -NH- | 0 | — | HN-CH=N- (imidazole-CH$_2$-) | cyclohexyl-CH$_2$- | -P(=O)(OCH$_3$)$_2$ |
| 43 | (CH$_3$)$_3$C-CH$_2$-C(=O)- | " | " | — | " | " | " |
| 44 | H$_3$C-C(=O)- | " | " | — | " | " | " |
| 45 | H- | " | " | — | " | " | " |
| 46 | naphthyl-(CH$_2$)$_2$-C(=O)- | " | " | — | (CH$_3$)$_2$CH-CH$_2$- | " | " |

-continued

| Ex. No. | X | Y | r | R$_5$ | R$_4$ | R$_3$ | $\overset{M}{\underset{Z'-R_2}{-P-Z-R_1}}$ |
|---|---|---|---|---|---|---|---|
| 47 | (CH$_3$)$_3$C—S(=O)$_2$— | —CH$_2$— | 1 | C$_6$H$_5$CH$_2$— | (CH$_3$)$_2$CH—CH$_2$— | cyclohexyl-CH$_2$— | O=P(OCH$_3$)$_2$ |
| 48 | " | " | " | " | imidazolyl-CH$_2$— | " | " |
| 49 | (C$_2$H$_5$O)$_2$P(=O)— | " | " | " | (CH$_3$)$_2$CH—CH$_2$— | " | " |
| 50 | " | " | " | " | " | " | " |
| 51 | HS— | " | " | " | " | " | " |
| 52 | (CH$_3$)$_3$C—C(=O)— | " | " | " | " | " | " |
| 53 | (C$_6$H$_5$CH$_2$)$_2$— | —CH$_2$— | 1 | C$_6$H$_5$CH$_2$— | (CH$_3$)$_2$CH—CH$_2$— | cyclohexyl-CH$_2$— | O=P(OCH$_3$)$_2$ |
| 54 | (CH$_3$)$_3$C—C(=O)— | O | " | " | " | " | " |
| 55 | H$_3$C-N(piperazinyl)-C(=O)— | —NH— | " | 1-naphthyl-CH$_2$— | | | O=P(OCH$_3$)(CH$_3$) |

-continued

| Ex. No. | X | Y | r | R$_5$ | R$_4$ | R$_3$ | $\underset{Z'-R_2}{\overset{M}{\underset{\|}{P}}}-Z-R_1$ |
|---|---|---|---|---|---|---|---|
| 56 | H$_2$N—(CH$_2$)$_5$—C(=O)— | " | " | —CH$_2$—C$_6$H$_5$ | " | " | " |
| 57 | C$_6$H$_5$—CH$_2$—CH$_2$—C(=O)— | " | 0 | — | " | —CH$_2$—C$_6$H$_{11}$ | O=P(—O—CH(CH$_3$)$_2$)(—OCH$_3$) |
| 58 | (CH$_3$)$_3$C—O—C(=O)— | —NH— | 0 | — | H—N-imidazolyl-CH$_2$— | " | O=P(—O—CH(CH$_3$)$_2$)(—OCH$_3$) |
| 59 | " | " | " | — | CH$_3$—N-imidazolyl-CH$_2$— | " | O=P(—O—C$_6$H$_5$)(—OCH$_3$) |
| 60 | " | " | " | — | H—N-imidazolyl-CH$_2$— | " | O=P(—NH—CH$_3$)(—OCH$_3$) |
| 61 | C$_6$H$_5$—CH$_2$—CH$_2$—C(=O)— | " | " | — | (CH$_3$)$_2$CH—CH$_2$— | " | O=P(—O—CH$_2$—C$_6$H$_5$)(—OCH$_3$) |

-continued

| Ex. No. | X | Y | r | R$_5$ | R$_4$ | R$_3$ | M=P(—Z—R$_1$)(Z'—R$_2$) |
|---|---|---|---|---|---|---|---|
| 62 | phenyl-CH$_2$—CH$_2$—C(=O)— | —NH— | 0 | — | HO—CH$_2$—CH$_2$— | cyclohexyl-CH$_2$— | O=P(CH$_3$)(OCH$_2$CH(CH$_3$)$_2$) |
| 63 | " | " | " | — | HO$_2$C—CH$_2$— | " | O=P(OCH$_3$)(O-cyclohexyl) |
| 64 | " | " | " | — | H$_2$N—C(=O)—CH$_2$— | " | O=P(OCH$_3$)(O—CH$_2$-cyclohexyl) |
| 65 | (CH$_3$)$_3$C—O—C(=O)— | " | 0 | — | (thiazol-4-yl)-CH$_2$— | " | O=P(CH$_3$)(OCH$_3$) |
| 66 | phenyl-CH$_2$—CH$_2$—C(=O)— | —NH— | 0 | — | (CH$_3$)$_2$CH—CH$_2$— | cyclohexyl-CH$_2$— | O=P(CH$_3$)(OCH$_3$) |
| 67 | HO-phenyl-CH$_2$—CH$_2$—C(=O)— | " | " | — | (imidazol-4-yl)-CH$_2$— | " | O=P(OCH(CH$_3$)$_2$)(NH—CH$_3$) |

-continued

| Ex. No. | X | Y | r | R$_5$ | R$_4$ | R$_3$ | $-\overset{\overset{\displaystyle M}{\|}}{\underset{\underset{\displaystyle Z'-R_2}{\|}}{P}}-Z-R_1$ |
|---|---|---|---|---|---|---|---|
| 68 | C$_6$H$_5$—CH$_2$—CH$_2$—C(=O)— | " | " | — | " | (CH$_3$)$_2$CH—CH$_2$— | $-\overset{\overset{\displaystyle O}{\|}}{\underset{\underset{\displaystyle OCH_3}{\|}}{P}}-NH-CH_2-C_6H_5$ |
| 69 | H— | " | " | — | " | cyclohexyl-CH$_2$— | $-\overset{\overset{\displaystyle O}{\|}}{\underset{\underset{\displaystyle O-CH(CH_3)_2}{\|}}{P}}-NH-CH_3$ |

What is claimed is:
1. A compound of the formula

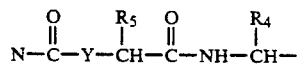

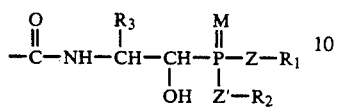

including pharmaceutically acceptable salts thereof; wherein

M is oxygen or sulfur;
Y is —CH$_2$—, —NH— or —O—;

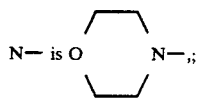 is O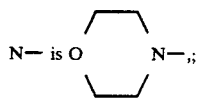N—;

is
$R_1$, $R_1'$, $R_2$, $R_2'$, $R_{12}$, $R_{13}$ and $R_{14}$ are independently selected from hydrogen, alkyl, arylalkyl, aryl, heteroaryl and cycloalkyl;

Z and Z' are independently selected from a single bond

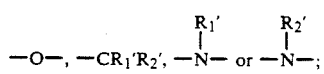

$R_3$ and $R_5$ are independently selected from hydrogen, lower alkyl, halo substituted lower alkyl, —(CH$_2$)$_n$—aryl, —(CH$_2$)$_n$—heterocyclo, —(CH$_2$)$_n$—OH, —(CH$_2$)$_n$—O—lower alkyl,
—(CH$_2$)$_n$—NH$_2$,
—(CH$_2$)$_n$—SH, —(CH$_2$)$_n$—S—lower alkyl,
—(CH$_2$)$_n$—O—(CH$_2$)$_g$—OH,
—(CH$_2$)$_n$—O—(CH$_2$)$_g$—NH$_2$, —(CH$_2$)$_n$—S—(CH$_2$)$_g$—OH, —(CH$_2$)$_n$—$\overset{O}{\overset{\|}{C}}$—OH, —(CH$_2$)$_n$—S—(CH$_2$)$_g$—NH$_2$, —(CH$_2$)$_n$—NH—$\overset{NH}{\underset{NH_2}{C}}$,

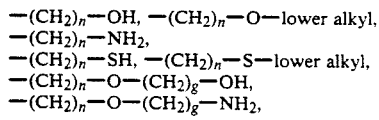

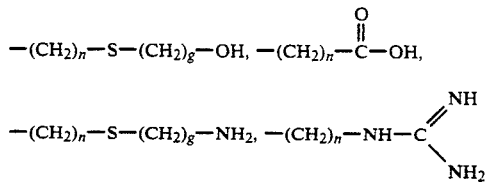

and —(CH$_2$)$_n$—cycloalkyl;

$R_4$ is selected from hydrogen, lower alkyl, halo substituted lower alkyl, —(CH$_2$)$_n$—aryl, —(CH$_2$)$_n$—heterocyclo, —(CH$_2$)$_n$—OH, —(CH$_2$)$_n$—O—lower alkyl, —(CH$_2$)$_n$—NH$_2$, —(CH$_2$)$_n$—SH, —(CH$_2$)$_n$—S—lower alkyl, —(CH$_2$)$_n$—O—(CH$_2$)$_g$—OH, —(CH$_2$)$_n$—O—(CH$_2$)$_g$—NH$_2$, —(CH$_2$)$_n$—S—(CH$_2$)$_g$—OH, —(CH$_2$)$_n$—$\overset{O}{\overset{\|}{C}}$—OH, —(CH$_2$)$_n$—S—(CH$_2$)$_g$—NH$_2$, —(CH$_2$)$_n$—NH—$\overset{NH}{\underset{NH_2}{C}}$,

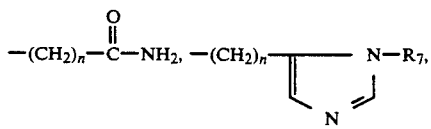

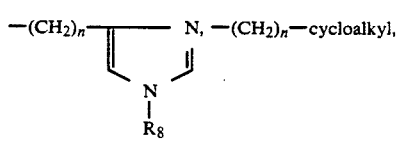

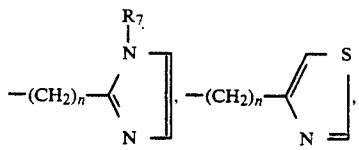

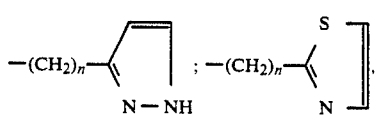

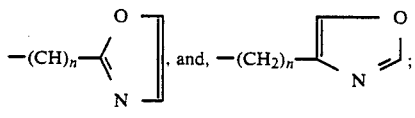

n is an integer from 1 to 5;
g is an integer from 2 to 5;
$R_7$ is

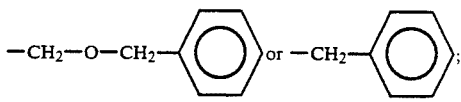

$R_8$ is 2,4-dinitrophenyl,

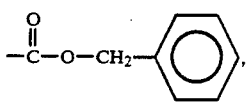

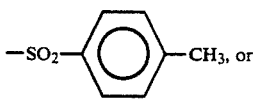

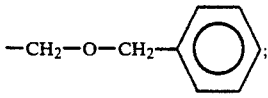

$R_9$ is hydrogen, lower alkyl,

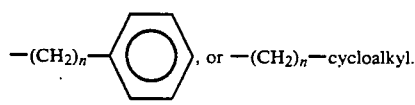

2. A compound in accordance with claim 1 wherein
R$_3$ is straight or branched chain lower alkyl of 3 to 5 carbons, —(CH$_2$)$_n$—cyclopentyl, —(CH$_2$)$_n$—cyclohexyl

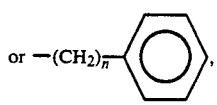

wherein n is an integer from 1 to 3;
R$_4$ is hydrogen, straight or branched chain lower alkyl of up to 5 carbons,

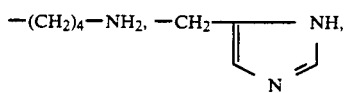

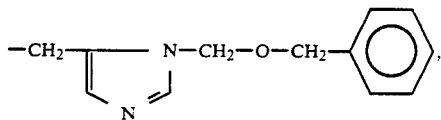

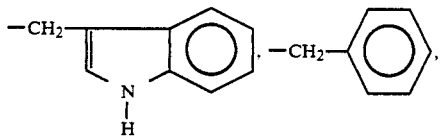

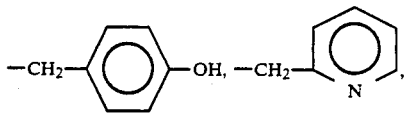

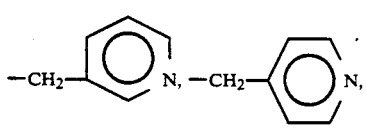

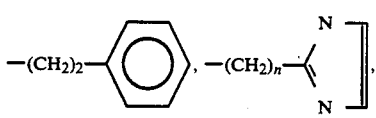

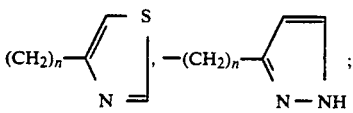

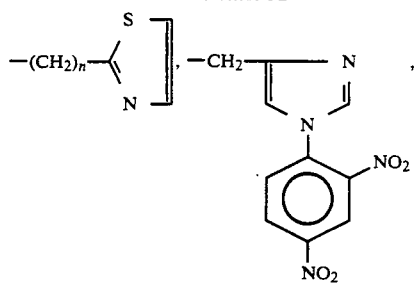

—CH$_2$—CH(CH$_3$)$_2$, —CH$_2$—CH$_2$—CH$_2$—CH$_3$,
—CH$_2$—CH$_2$—OH,

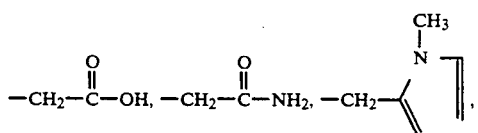

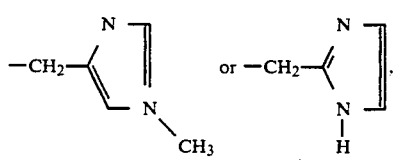

wherein
n is an integer from 1 to 3;
R$_5$ is straight or branched chain lower alkyl of up to 5 carbons,

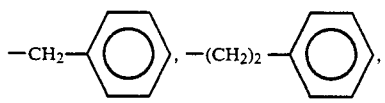

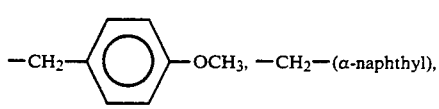

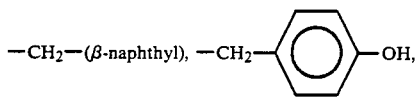

—CH$_2$—cyclopentyl, —CH$_2$—cyclohexyl,

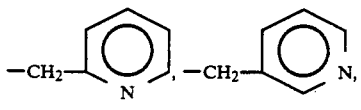

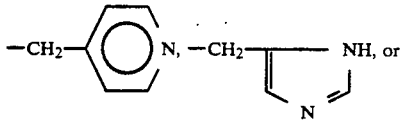

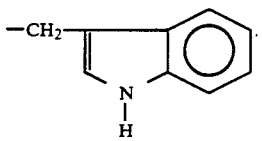

3. A compound in accordance with claim 1 wherein when r is one, X—Y— is
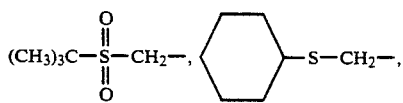
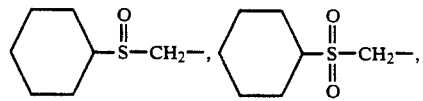
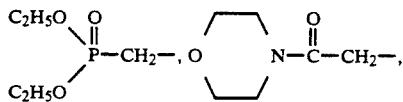
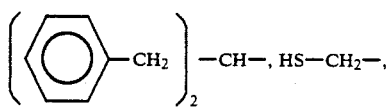
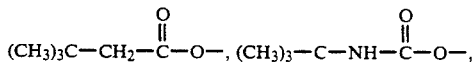
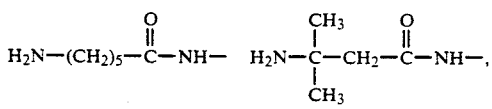
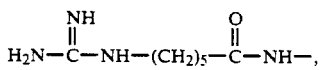
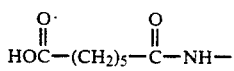
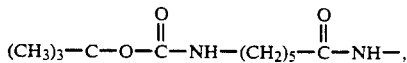
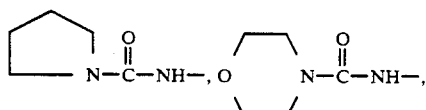
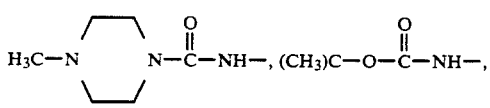
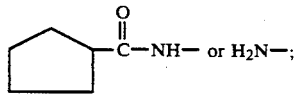
when r is zero, X—Y— is
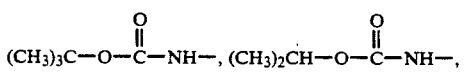
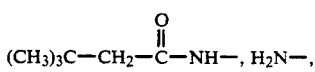
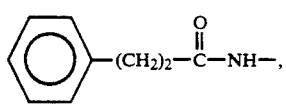
-continued
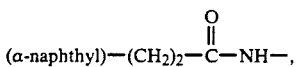
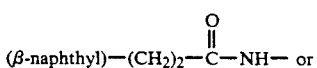
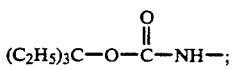
$R_1$ and $R_2$ are independently selected from hydrogen,
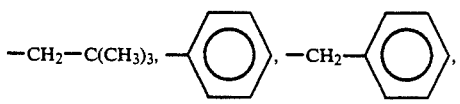
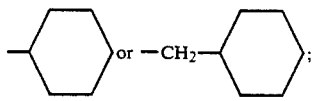
$R_3$ is 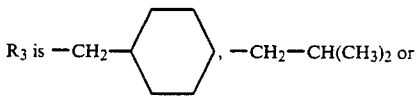
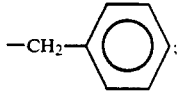
$R_4$ is 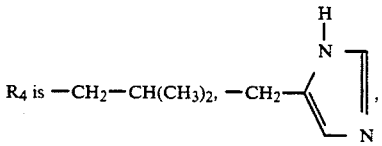
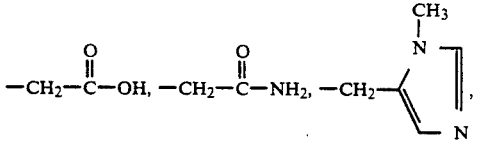
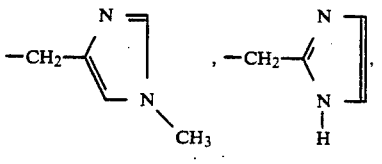
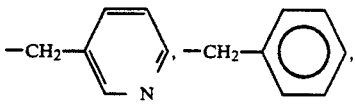
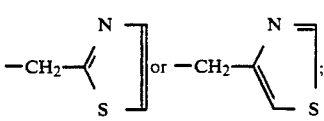

R$_5$ is 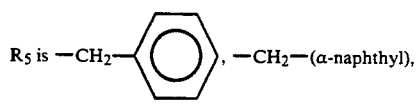, —CH$_2$—(α-naphthyl),

—CH$_2$—(β-naphthyl), 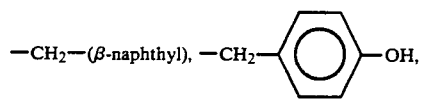

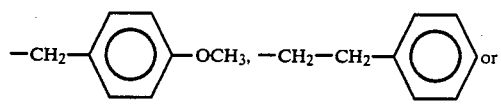

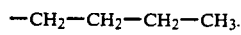

4. A compound of claim 1 wherein

M, Z and Z' are each oxygen;

R$_1$ and R$_2$ are each methyl;

R$_3$ is 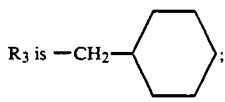;

R$_4$ is 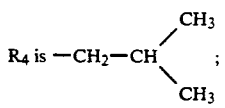;

R$_5$ is benzyl;
r is one;
Y is —NH—; and

X is 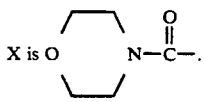.

5. A composition for treating hypertension in a mammalian species comprising a pharmaceutically acceptable carrier and an anti-hypertensively effective amount of a compound of claim 1.

6. A method of treating hypertension in a mammalian species which comprises administering an anti-hypertensively effective amount of the composition of claim 5.

* * * * *